(12) United States Patent
Nishiyama et al.

(10) Patent No.: US 9,079,170 B2
(45) Date of Patent: Jul. 14, 2015

(54) METHOD FOR PRODUCING DIARYL CARBONATE

(75) Inventors: Budianto Nishiyama, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 0 days.

(21) Appl. No.: 13/579,649

(22) PCT Filed: Feb. 23, 2011

(86) PCT No.: PCT/JP2011/054018

§ 371 (c)(1),
(2), (4) Date: Aug. 17, 2012

(87) PCT Pub. No.: WO2011/105442

PCT Pub. Date: Sep. 1, 2011

(65) Prior Publication Data

US 2012/0316357 A1 Dec. 13, 2012

(30) Foreign Application Priority Data

Feb. 23, 2010 (JP) ................................. 2010-037928
Feb. 23, 2010 (JP) ................................. 2010-037930

(51) Int. Cl.
*C07C 68/06* (2006.01)
*B01J 31/02* (2006.01)

(52) U.S. Cl.
CPC .......... *B01J 31/0214* (2013.01); *B01J 31/0252* (2013.01); *C07C 68/06* (2013.01); *B01J 2531/42* (2013.01); *B01J 2531/46* (2013.01)

(58) Field of Classification Search
None
See application file for complete search history.

(56) References Cited

U.S. PATENT DOCUMENTS

| | | | |
|---|---|---|---|
| 2,880,221 | A | 3/1959 | Haslam |
| 5,380,908 | A | 1/1995 | Murata et al. |
| 5,734,004 | A | 3/1998 | Kuhling et al. |
| 5,760,156 | A | 6/1998 | Inoki et al. |
| 5,872,275 | A | 2/1999 | Komiya et al. |
| 6,197,918 | B1 | 3/2001 | Uno et al. |
| 6,262,210 | B1 | 7/2001 | Tojo et al. |
| 2008/0097116 | A1 | 4/2008 | Miyake |
| 2008/0177099 | A1 | 7/2008 | Miyake |

FOREIGN PATENT DOCUMENTS

| | | |
|---|---|---|
| EP | 0780361 A1 | 6/1997 |
| JP | S64-052786 A | 2/1989 |
| JP | H01-129031 A | 5/1989 |
| JP | H04-211038 A | 8/1992 |
| JP | H06-157410 A | 6/1994 |
| JP | H08-259504 A | 10/1996 |
| JP | H08-259505 A | 10/1996 |
| JP | H09-059224 A | 3/1997 |
| JP | H09-110805 A | 4/1997 |
| JP | H09-165357 A | 6/1997 |
| JP | H09-169704 A | 6/1997 |
| JP | H09-194437 A | 7/1997 |
| JP | H10-036299 A | 2/1998 |
| JP | H10-043606 A | 2/1998 |
| JP | H10-045675 A | 2/1998 |
| JP | H11-092429 A | 4/1999 |
| JP | 2000-063332 A | 2/2000 |
| JP | 2000-072721 A | 3/2000 |
| JP | 2000-086769 A | 3/2000 |
| JP | 2000-191596 A | 7/2000 |
| JP | 2003-238487 A | 8/2003 |
| JP | 3528997 B2 | 3/2004 |
| JP | 2004-307400 A | 11/2004 |
| TW | 2006-33974 A | 10/2006 |
| WO | 97/11049 A1 | 3/1997 |
| WO | 2004/069740 A1 | 8/2004 |
| WO | 2006/067982 A1 | 6/2006 |
| WO | 2006/068053 A1 | 6/2006 |

OTHER PUBLICATIONS

Du et al.,"Novel catalytic systems containing n-BuSn(O)OH for the transesterification of dimethyl carbonate and phenol," Journal of Molecular Catalysis A: Chemical 246: 200-205 (2006).

Niu et al., "Transesterification of dimethyl carbonate and phenol to diphenyl carbonate catalyzed by samarium diiodide," Journal of Molecular Catalysis A: Chemical 259: 292-295 (2006).

Niu et al., "Transesterification of dimethyl carbonate and phenol to diphenyl carbonate catalyzed by titanocene complexes," Catalysis Communications, 8: 355-358 (2007).

International Search Report issued in International Application No. PCT/JP2011/054018 dated May 24, 2011.

Office Action issued in related Taiwanese Patent Application No. 100105942 dated Jul. 29, 2013.

Office Action issued in corresponding Taiwanese Patent Application No. 100105940 dated Jun. 24, 2013.

Search Report issued in International Application No. PCT/JP2011/054011 dated Apr. 5, 2011.

*Primary Examiner* — Alicia L Otton

(74) *Attorney, Agent, or Firm* — Morgan, Lewis & Bockius LLP

(57) ABSTRACT

The present invention provides a method for continuously producing a diaryl carbonate stably for a long time with high productivity. The method for producing a diaryl carbonate according to the present invention comprises a step (1) of obtaining an alkylaryl carbonate; a step (2) of obtaining a reaction product from the alkylaryl carbonate; a step (3) of separating the diaryl carbonate and a high boiling component from the reaction product; and a step (4) of recycling the high boiling component into the steps (1) and/or (2), wherein the high boiling component recycled in the step (4) includes a particular compound, and the particular compound satisfies a particular condition.

21 Claims, 3 Drawing Sheets

METHOD FOR PRODUCING DIARYL CARBONATE

The present application is a U.S. National Phase Application of International Application No. PCT/JP2011/054018 filed Feb. 23, 2011, which claims the benefit of priority of Japanese Application Nos. 2010-037928 filed Feb. 23, 2010 and 2010-037930 filed Feb. 23, 2010, the disclosures of which are incorporated herein by reference in their entireties.

TECHNICAL FIELD

The present invention relates to a method for producing diaryl carbonates.

BACKGROUND ART

Diaryl carbonates are useful as raw materials for the industrial production of polycarbonates that are engineering plastics. Therefore, techniques for stably producing diaryl carbonates with high efficiency are important.

A method for subjecting a dialkyl carbonate and an aromatic monohydroxy compound (for example, a phenol) to a transesterification reaction given by the following formula (A) so as to obtain an alkylaryl carbonate, and then performing a disproportionation reaction given by the following formula (B), using this alkylaryl carbonate, so as to obtain a diaryl carbonate is known as a method for producing a diaryl carbonate. The formulas (A) and (B) are as follows:

[Formula 1]

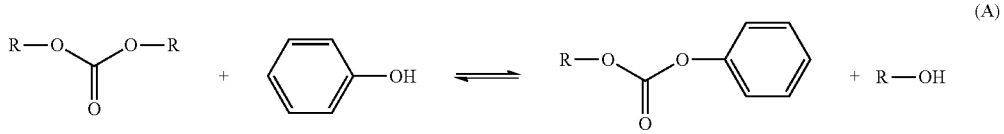

(A)

[Formula 2]

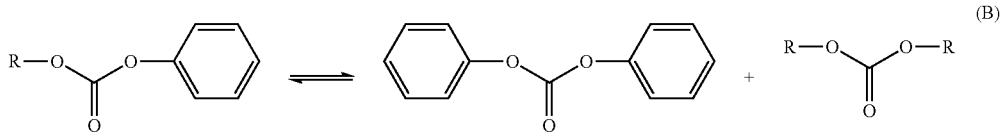

(B)

wherein R represents a linear or branched aliphatic group having 1 to 12 carbon atoms, or an alicyclic aliphatic group having 5 to 12 carbon atoms.

However, the transesterification reaction given by the above formula (A), and the disproportionation reaction given by the above formula (B) are both equilibrium reactions and have a slow reaction rate. Particularly, a problem of the transesterification reaction is that the equilibrium is biased to the original system, and therefore, the reaction efficiency is low.

In view of such problems, studies on catalysts for improving the reaction rate in the transesterification reaction given by the above formula (A), and the disproportionation reaction given by the above formula (B) have been made.

As such catalysts, for example, titanium compounds (for example, see Patent Document 1 and 2, and Non Patent Document 1), organic tin compounds (for example, see Patent Document 3, and Non Patent Document 2), nitrogen-containing basic compounds (for example, see Patent Document 4), and samarium compounds (for example, see Non Patent Document 3) have been proposed.

Further, methods for continuously producing diaryl carbonates have been also proposed. Examples of the methods include a continuous production method for separating a product from a mixture comprising a catalyst and the product by distillation and circulating the distillation residue including the catalyst component into the reaction step in order to effectively use the catalyst component (for example, see Patent Document 5 and 6). In the continuous production method, it is possible to remove part of the distillation residue including the catalyst component circulated and appropriately feed a new catalyst component, as required, for the purpose of preventing the accumulation of the by-product.

It is known that in the transesterification reaction given by the above formula (A), and the disproportionation reaction given by the above formula (B), a side reaction occurs, in addition to the reaction in which the targeted diaryl carbonate is produced. Examples of the side reaction include a Fries rearrangement reaction as given by the following formula (C). In order to separate a salicylate ester produced by the Fries rearrangement reaction, the purification of the final targeted product is essential. The formula (C) is as follows:

[Formula 3]

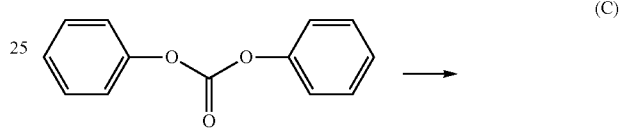

(C)

-continued

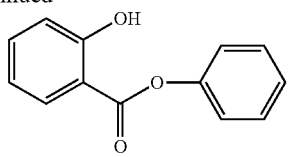

The separation and purification of the by-product and the targeted main product may be difficult, and purification techniques for separating the by-product have been proposed so far (for example, see Patent Document 7).

Further, when the separation and purification of the by-product and the main product is performed under high temperature conditions (for example, 200° C. or more), the catalyst function may be decreased by pyrolysis and the like. Technical proposals for methods for suppressing such a decrease in catalyst function are made (for example, see Patent Document 8).

The catalyst used in the reactions given by the above formulas (A) and (B) is solid or liquid, and there are also reports regarding methods for feeding the catalyst.

Examples of the feed methods include a method for feeding a catalyst having an alkyl moiety similar to an alkyl moiety in a dialkyl carbonate used for a raw material (for example, titanium tetraalkoxide) (for example, see Patent Document 9). According to the feed method, the mixing of the by-product of an alkyl alcohol as by-product from the catalyst can be prevented.

Other examples include a method for continuously feeding a dialkyl carbonate, an aromatic hydroxy compound, and a catalyst to a reactor, continuously removing an alcohol as by-product from a distillation column annexed to the reactor, and further removing aromatic carbonates including an alkylaryl carbonate, an diaryl carbonate, or a mixture thereof from the reactor (for example, see Patent Document 10), and a method for separating the feed position of the dialkyl carbonate and the aromatic hydroxy compound and the feed position of the catalyst (for example, see Patent Document 11). According to these methods, the precipitation of the catalyst due to operation for a long time is suppressed, and clogging can be prevented.

The catalyst used in the reactions given by the above formulas (A) and (B) is usually in a state dissolved in a reaction solution under reaction conditions. The catalyst has a higher boiling point than that of aromatic carbonates, and therefore, in order to obtain a high purity aromatic carbonate from a reaction product solution, it is necessary to first remove a low boiling component from the reaction product solution and then separate a diaryl carbonate of a high boiling component from the catalyst to purify the diaryl carbonate. It is known that at this time, the catalyst may be recovered as a high boiling component and recycled, and part of the deactivated component may be removed (for example, see Patent Document 8). A method for separating a catalyst by using a catalyst having a low boiling point, such as an alkylamine, is also known (for example, see Patent Document 12).

LIST OF PRIOR ART DOCUMENTS

Patent Document

Patent Document 1: Japanese Patent Laid-Open No. 8-259505
Patent Document 2: Japanese Patent Laid-Open No. 2000-191596
Patent Document 3: Japanese Patent Laid-Open No. 8-259504
Patent Document 4: Japanese Patent No. 3528997
Patent Document 5: Japanese Patent Laid-Open No. 9-59224
Patent Document 6: Japanese Patent Laid-Open No. 9-110805
Patent Document 7: Japanese Patent Laid-Open No. 9-194437
Patent Document 8: Japanese Patent Laid-Open No. 9-169704
Patent Document 9: Japanese Patent Laid-Open No. 2000-72721
Patent Document 10: Japanese Patent Laid-Open No. 6-157410
Patent Document 11: Japanese Patent Laid-Open No. 2004-307400
Patent Document 12: Japanese Patent Laid-Open No. 2003-238487

Non Patent Document

Non Patent Document 1: Catalysis Communications, 8 (2007), 355-358

Non Patent Document 2: Journal of Molecular Catalysis A: Chemical, 246 (2006), 200-205
Non Patent Document 3: Journal of Molecular Catalysis A: Chemical, 259 (2006), 292-295

SUMMARY OF INVENTION

Problems to be Solved by the Invention

However, the decrease in catalyst function is only determined by a decrease in product concentration by analyzing the concentration of the alkylaryl carbonate and the diaryl carbonate that are products, with the lapse of a fixed operation time. Therefore, due to fluctuations in operation conditions, and the like, a decrease in productivity may occur, though the cause is unclear.

The effect of the compound produced by the side reaction on the catalyst has not been sufficiently clarified yet.

Further, in the industrial production of diaryl carbonates, the clogging of the reaction apparatus with the catalyst is a very important problem. When the reaction apparatus is clogged with the catalyst, it may be necessary to completely stop the production of the diaryl carbonate, and perform the overhaul of the reactor, the distillation column, the piping, and the like, and a problem is that much time, effort, and cost are required. The methods for feeding the catalyst according to conventional art described above have not led to a sufficient solution of such a problem.

Under such circumstances, the demand for the development of techniques for stably producing diaryl carbonates with high efficiency over a long time has increased.

Accordingly, it is an object of the present invention to clarify the effect of a produced by-product on a catalyst in the production of the diaryl carbonate to provide a method for producing a diaryl carbonate stably and efficiently in which a decrease in catalyst function is suppressed, and a catalyst is stably fed without a reaction apparatus being clogged with the catalyst.

Means for Solving the Problems

In view of the above-described problems, the present inventors have diligently studied methods for producing diaryl carbonates. As a result, it has been clarified that in a state in which a particular amount of a particular by-product coexists with a metal-containing catalyst composition, the productivity of a diaryl carbonate is stable, and it has been further clarified that by using a particular composition in a particular step, the clogging of a reaction apparatus with the catalyst can be suppressed. It has been found that by controlling the ratio of a particular by-product to the metal atoms of a metal-containing catalyst composition, and further by using a particular composition in a particular step, a diaryl carbonate can be stably produced with high efficiency for a long period, leading to the completion of the present invention.

Specifically, the present invention relates to, for example, the following.

[1]

A method for producing a diaryl carbonate, using a metal-containing catalyst composition as a reaction catalyst, comprising:

a step (1) of subjecting a dialkyl carbonate and an aromatic monohydroxy compound to a transesterification reaction so as to obtain an alkylaryl carbonate, and removing an alcohol as by-product from a reaction system;

a step (2) of subjecting the alkylaryl carbonate obtained in the step (1) to a transesterification or disproportionation reaction so as to obtain a reaction product including the diaryl carbonate;

a step (3) of distilling the reaction product obtained in the step (2) to separate the reaction product into a low boiling component including the diaryl carbonate and a high boiling component including the reaction catalyst; and a step (4) of recycling the high boiling component separated in the step (3) into the steps (1) and/or (2), wherein:

the high boiling component separated in the step (3) includes 70% by mass or less of a component having a higher boiling point than that of the diaryl carbonate;

the high boiling component separated in the step (3) includes a compound represented by the formula (1):

[Formula 4]

(1)

wherein $Ar^1$ represents an unsubstituted or substituted arylene group having 6 to 20 carbon atoms, X and Y—O are located at an ortho position to each other, X represents a hydroxy group or a substituent given by the formula (2) or (3), and Y represents hydrogen or a substituent given by the formula (3), the formulas (2) and (3) being as follows:

[Formula 5]

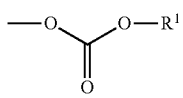

(2)

[Formula 6]

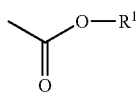

(3)

wherein $R^1$ represents a linear or branched aliphatic group having 1 to 12 carbon atoms, an alicyclic aliphatic group having 5 to 12 carbon atoms, or an unsubstituted or substituted aryl group having 6 to 20 carbon atoms; and the high boiling component recycled in the step (4) includes compounds given by (i) to (iii):

(i) a compound of the formula (1) where X represents the formula (2) or (3), and Y represents the formula (3);

(ii) a compound of the formula (1) where X represents a hydroxy group, and Y represents the formula (3), and/or a compound of the formula (1) where X represents the formula (3), and Y represents hydrogen;

(iii) a compound of the formula (1) where X represents a hydroxy group, and Y represents hydrogen;

the compounds of (i) to (iii) satisfying conditions given by (iv) to (vi), respectively:

(iv) "total moles of the compounds of (i)/moles of metal atoms" is 0.005 to 20;

(v) "total moles of the compounds of (ii)/moles of metal atoms" is 0.005 to 4; and (vi) "moles of the compound of (iii)/moles of metal atoms" is less than 2.

[2]
The method for producing the diaryl carbonate according to [1], wherein the metal-containing catalyst composition is a titanium-containing catalyst composition.

[3]
The method for producing the diaryl carbonate according to [2], wherein the titanium-containing catalyst composition is a titanium-containing composition formed of a diaryl carbonate and an aryloxytitanium composition, and titanium constituting the aryloxytitanium composition has a content of 0.1 to 20% by mass based on 100% by mass of the titanium-containing composition.

[4]
The method for producing the diaryl carbonate according to [3], wherein the titanium constituting the aryloxytitanium composition is tetravalent.

[5]
The method for producing the diaryl carbonate according to [3] or [4], wherein the aryloxytitanium composition has 1 or more and 4 or less aryloxy groups per titanium atom.

[6]
The method for producing the diaryl carbonate according to any of [1] to [5], wherein a reaction solvent is used in the steps (1) and/or (2), and the metal-containing catalyst composition is soluble in the reaction solvent or forms a homogeneous phase with the reaction solvent.

[7]
The method for producing the diaryl carbonate according to any of [1] to [6], wherein the compound represented by the formula (1) is at least one selected from a group of compounds represented by the following formulas (4) to (8):

[Formula 7]

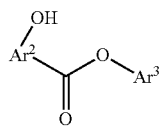

(4)

wherein $Ar^2$ represents an unsubstituted or substituted arylene group having 6 to 20 carbon atoms, $Ar^3$ represents an unsubstituted or substituted aryl group having 6 to 20 carbon atoms, and two substituents on $Ar^2$ are located at an ortho position to each other;

[Formula 8]

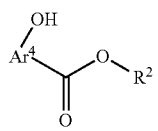

(5)

wherein $Ar^4$ represents an unsubstituted or substituted arylene group having 6 to 20 carbon atoms, $R^2$ represents a linear or branched aliphatic group having 1 to 12 carbon atoms, or an alicyclic aliphatic group having 5 to 12 carbon atoms, and two substituents on $Ar^4$ are located at an ortho position to each other;

[Formula 9]

(6)

wherein $Ar^5$ represents an unsubstituted or substituted arylene group having 6 to 20 carbon atoms, and two hydroxy groups on $Ar^5$ are located at an ortho position to each other;

[Formula 10]

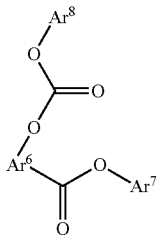

(7)

wherein $Ar^6$ represents an unsubstituted or substituted arylene group having 6 to 20 carbon atoms, $Ar^7$ and $Ar^8$ each independently represent an unsubstituted or substituted aryl group having 6 to 20 carbon atoms, and two substituents on $Ar^6$ are located at an ortho position to each other; and

[Formula 11]

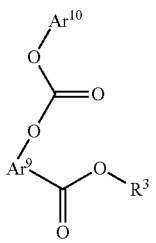

(8)

wherein $Ar^9$ represents an unsubstituted or substituted arylene group having 6 to 20 carbon atoms, $Ar^{10}$ represents an unsubstituted or substituted aryl group having 6 to 20 carbon atoms, $R^3$ represents a linear or branched aliphatic group having 1 to 12 carbon atoms, or an alicyclic aliphatic group having 5 to 12 carbon atoms, and two substituents on $Ar^9$ are located at an ortho position to each other.

[8]
The method for producing the diaryl carbonate according to any of [1] to [7], wherein the high boiling component recycled in the step (4) has "total moles of the compounds represented by the formula (1)/moles of metal atoms" from 0.005 to 10.

[9]
The method for producing the diaryl carbonate according to any of [1] to [8], wherein the steps (1) and/or (2) is performed in the presence of a composition A comprising the diaryl carbonate, an aryloxytitanium composition, and a compound represented by the following formulas (X) and/or (Y), and the composition A has a ratio of total moles of the compounds represented by the following formulas (X) and (Y) to moles of titanium atoms (a total of the compounds represented by the formulas (X) and (Y)/titanium atoms) from 0.005 to 4, the formulas (X) and (Y) being:

[Formula 12]

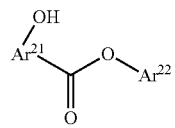

(X)

wherein $Ar^{21}$ represents an unsubstituted or substituted arylene group having 6 to 20 carbon atoms, $Ar^{22}$ represents an unsubstituted or substituted aryl group having 6 to 20 carbon atoms, and two substituents on $Ar^{21}$ are located at an ortho position to each other; and

[Formula 13]

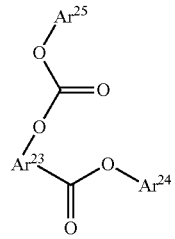

(Y)

wherein $Ar^{23}$ represents an unsubstituted or substituted arylene group having 6 to 20 carbon atoms, $Ar^{24}$ and $Ar^{25}$ each independently represent an unsubstituted or substituted aryl group having 6 to 20 carbon atoms, and two substituents on $Ar^{23}$ are located at an ortho position to each other.

[10]
The method for producing the diaryl carbonate according to any of [1] to [9], further comprising
sampling the high boiling component recycled in the step (4),
adding a monodentate or polydentate ligand capable of coordination to the metal atoms, to the sampled high boiling component at 1 equivalent or more with respect to titanium atoms therein so as to prepare an analysis sample, and
analyzing the analysis sample to quantify the compounds given by (i) to (iii) included in the high boiling component.

[11]
The method for producing the diaryl carbonate according to any of [1] to [10], further comprising
sampling the high boiling component recycled in the step (4),
adding at least one additive to the sampled high boiling component at 1 equivalent or more with respect to the metal atoms therein so as to prepare an analysis sample, the additive being selected from the group consisting of water, polyhydroxy compounds, nitrogen-containing heterocyclic compounds, sulfur-containing heterocyclic compounds, fluorine-substituted alcohols, and fluorine-substituted organic acids, and
analyzing the analysis sample by gas or liquid chromatography so as to quantify the compounds given by (i) to (iii) included in the high boiling component.

[12]

The method for producing the diaryl carbonate according to [10] or [11], further comprising performing control so that the compounds given by (i) to (iii) included in the high boiling component recycled in the step (4) satisfy the conditions of (iv) to (vi), respectively, after the step of quantifying the compounds given by (i) to (iii) according to [10] or [11].

[13]

The method for producing the diaryl carbonate according to any of [1] to [12], wherein the dialkyl carbonate used in the step (1) is a compound represented by the formula (9):

[Formula 14]

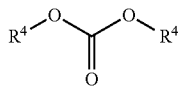
(9)

wherein $R^4$ represents a linear or branched aliphatic group having 1 to 12 carbon atoms, or an alicyclic aliphatic group having 5 to 12 carbon atoms, the aromatic monohydroxy compound used in the step (1) is a compound represented by the formula (10):

[Formula 15]

$Ar^{11}$—OH (10)

wherein $Ar^{11}$ represents an unsubstituted or substituted aryl group having 6 to 20 carbon atoms, the alkylaryl carbonate obtained in the step (1) is a compound represented by the formula (11):

[Formula 16]

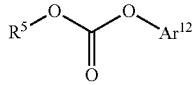
(11)

wherein $R^5$ represents a linear or branched aliphatic group having 1 to 12 carbon atoms, or an alicyclic aliphatic group having 5 to 12 carbon atoms, and $Ar^{12}$ represents an unsubstituted or substituted aryl group having 6 to 20 carbon atoms, and the diaryl carbonate obtained in the step (2) is a compound represented by the formula (12):

[Formula 17]

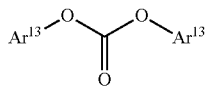
(12)

wherein $Ar^{13}$ represents an unsubstituted or substituted aryl group having 6 to 20 carbon atoms.

[14]

The method for producing the diaryl carbonate according to [9], wherein in the steps (1) and/or (2), production of the diaryl carbonate is started by feeding the composition A.

[15]

The method for producing the diaryl carbonate according to any of [1] to [14], wherein the reactions in the steps (1) and (2) are performed using a reaction apparatus comprising at least one selected from the group consisting of an agitation tank, an agitation tank with multistage impellers, a packed column, a distillation column, a multistage distillation column, a continuous multistage distillation column, a reactor comprising an internal support, and a forced circulation reactor.

[16]

The method for producing the diaryl carbonate according to [15], wherein in the step (1), the dialkyl carbonate and the aromatic monohydroxy compound are continuously fed to the reaction apparatus, and in the step (2) the reaction product obtained is continuously removed from the reaction apparatus.

[17]

The method for producing the diaryl carbonate according to any of [1] to [16], wherein the metal atoms in the metal-containing catalyst composition in the step (1) or (2) have a content of 0.0001 to 20% by mass.

[18]

The method for producing the diaryl carbonate according to [13], wherein $R^4$ in the formula (9) is an aliphatic alkyl group having 1 to 8 carbon atoms.

[19]

The method for producing the diaryl carbonate according to any of [1] to [18], wherein the steps (1) and (2) have a reaction temperature of 150 to 300° C., and a reaction time of 0.05 to 50 hr.

[20]

The method for producing the diaryl carbonate according to any of [1] to [19], wherein the distillation in the step (3) is performed by a distillation column, the distillation column has a temperature of 150 to 300° C. at the column bottom, and the distillation column provides a residence time of 0.02 to 100 hr at the column bottom.

[21]

The method for producing the diaryl carbonate according to [3] or [4], wherein the aryloxytitanium composition is phenoxytitanium.

[22]

The method for producing the diaryl carbonate according to any of [1] to [21], wherein the diaryl carbonate is diphenyl carbonate.

Advantages of the Invention

With the method for producing the diaryl carbonate according to the present invention, the diaryl carbonate can be produced stably for a long time with high productivity.

MODE FOR CARRYING OUT THE INVENTION

Figure 1:
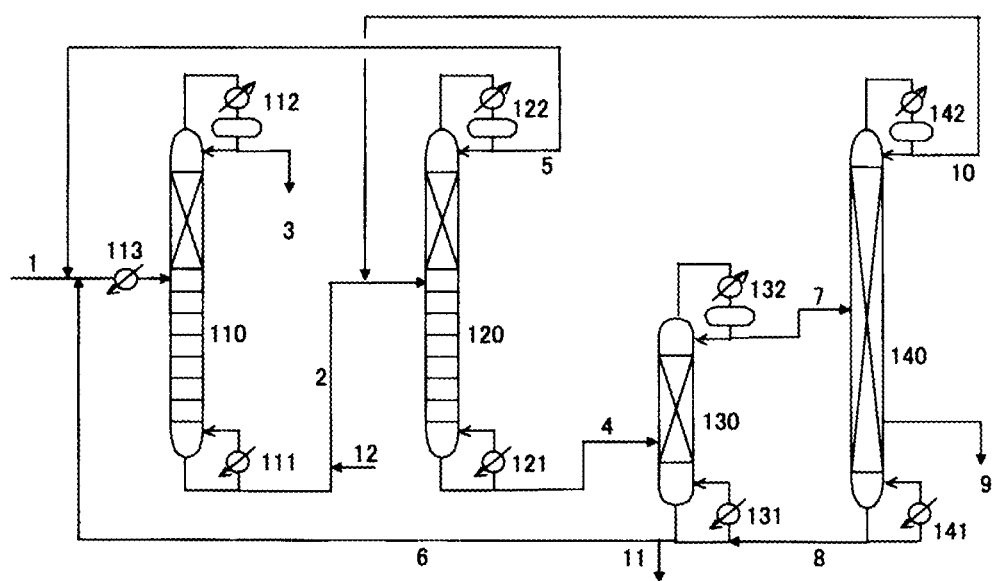
FIG. 1 shows a schematic configuration diagram of one example of a production apparatus for carrying out the method for producing the diaryl carbonate in the present embodiment.

The best mode for carrying out the present invention (hereinafter referred to as "the present embodiment") will be described in detail below. The present invention is not limited to the following embodiment. Various modifications can be made to the present invention without departing from the spirit thereof.

In the drawings, positional relationship, such as top, bottom, left, and right, is based on the positional relationship shown in the drawings, unless otherwise specified. Further, the dimensional ratio in the drawings is not limited to the ratio shown.

<Method for Producing Diaryl Carbonate>

A method for producing a diaryl carbonate according to the present embodiment is a method for producing a diaryl carbonate, using a metal-containing catalyst composition as a reaction catalyst, comprising a step (1) of subjecting a dialkyl carbonate and an aromatic monohydroxy compound to a transesterification reaction so as to obtain an alkylaryl carbonate, and removing an alcohol as by-product from the reaction system; a step (2) of subjecting the alkylaryl carbonate obtained in the step (1) to a transesterification or disproportionation reaction so as to obtain a reaction product including the diaryl carbonate; a step (3) of distilling the reaction product obtained in the step (2) to separate the reaction product into a low boiling component including the diaryl carbonate and a high boiling component including the reaction catalyst (hereinafter also described as a "high boiling component"); and a step (4) of recycling the high boiling component separated in the step (3) into the above steps (1) and/or (2), wherein the high boiling component separated in the above step (3) includes 70% by mass or less of a component having a higher boiling point than that of the diaryl carbonate; the high boiling component separated in the above step (3) includes a compound represented by the formula (1):

[Formula 18]

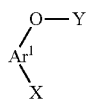

(1)

wherein $Ar^1$ represents an unsubstituted or substituted arylene group having 6 to 20 carbon atoms, X and Y—O are located at an ortho position to each other, X represents a hydroxy group or a substituent given by the formula (2) or (3), and Y represents hydrogen or a substituent given by the formula (3), the formulas (2) and (3) being as follows:

[Formula 19]

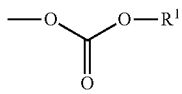

(2)

[Formula 20]

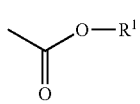

(3)

wherein $R^1$ represents a linear or branched aliphatic group having 1 to 12 carbon atoms, an alicyclic aliphatic group having 5 to 12 carbon atoms, or an unsubstituted or substituted aryl group having 6 to 20 carbon atoms, and the high boiling component recycled in the above step (4) includes compounds given by (i) to (iii):

(i) a compound of the formula (1) where X represents the formula (2) or (3), and Y represents the formula (3);

(ii) a compound of the formula (1) where X represents a hydroxy group, and Y represents the formula (3), and/or a compound of the formula (1) where X represents the formula (3), and Y represents hydrogen;

(iii) a compound of the formula (1) where X represents a hydroxy group, and Y represents hydrogen;

the compounds of (i) to (iii) satisfying conditions given by (iv) to (vi), respectively:

(iv) "the total moles of the compounds of (i)/the moles of metal atoms" is 0.005 to 20;

(v) "the total moles of the compounds of (ii)/the moles of metal atoms" is 0.005 to 4; and (vi) "the moles of the compound of (iii)/the moles of metal atoms" is less than 2.

The above steps (1) to step (4) will be described in detail below.

[Step (1)]

The step (1) is the step of subjecting the dialkyl carbonate and the aromatic monohydroxy compound to the transesterification reaction so as to obtain an alkylaryl carbonate, and removing the alcohol as by-product from the reaction system. The transesterification reaction is usually performed in the presence of a reaction catalyst described later.

(Dialkyl Carbonate)

The dialkyl carbonate used in the above step (1) is preferably a compound represented by the formula (9):

[Formula 21]

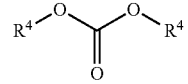

(9)

wherein $R^4$ represents a linear or branched aliphatic group having 1 to 12 carbon atoms, or an alicyclic aliphatic group having 5 to 12 carbon atoms. The above $R^4$ is more preferably an aliphatic alkyl group having 1 to 8 carbon atoms.

Examples of the above dialkyl carbonate include dimethyl carbonate, diethyl carbonate, dipropyl carbonate (isomers), dibutenyl carbonate (isomers), dibutyl carbonate (isomers), dipentyl carbonate (isomers), dihexyl carbonate (isomers), diheptyl carbonate (isomers), dioctyl carbonate (isomers), dinonyl carbonate (isomers), didecyl carbonate (isomers), dicyclopentyl carbonate, dicyclohexyl carbonate, and dicycloheptyl carbonate.

Particularly, as the above dialkyl carbonate, a dialkyl carbonate of the above formula (9) where $R^4$ represents a linear or branched aliphatic group having 1 to 6 carbon atoms is preferred. Specific examples of such a dialkyl carbonate include dimethyl carbonate, diethyl carbonate, dipropyl carbonate (isomers), dibutenyl carbonate (isomers), dibutyl carbonate (isomers), dipentyl carbonate (isomers), and dihexyl carbonate (isomers).

Such a dialkyl carbonate is easily separated from the diaryl carbonate by distillation and is preferred from a practical perspective.

(Aromatic Monohydroxy Compound)

The aromatic monohydroxy compound used in the above step (1) is preferably a compound represented by the formula (10):

[Formula 22]

$Ar^{11}$—OH (10)

wherein $Ar^{11}$ represents an unsubstituted or substituted aryl group having 6 to 20 carbon atoms.

Examples of $Ar^{11}$ in the above formula (10) include a phenyl group and various alkylphenyl groups, such as phenyl, tolyl (isomers), xylyl (isomers), trimethylphenyl (isomers), tetramethylphenyl (isomers), ethylphenyl (isomers), propylphenyl (isomers), butylphenyl (isomers), diethylphenyl (isomers), methylethylphenyl (isomers), pentylphenyl (isomers), hexylphenyl (isomers), and cyclohexylphenyl (isomers); various alkoxyphenyl groups, such as methoxyphenyl (isomers), ethoxyphenyl (isomers), and butoxyphenyl (isomers); various halogenated phenyl groups, such as fluorophenyl (isomers), chlorophenyl (isomers), bromophenyl (isomers), chloro(methyl)phenyl (isomers), and dichlorophenyl (isomers); and various substituted phenyl groups given by the formula (10a):

[Formula 23]

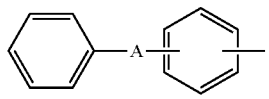

(10a)

wherein A represents any divalent group selected from the group consisting of a single bond, —O—, —S—, —CO—, —SO$_2$—, an alkylene group and a substituted alkylene group given by the following formula (10a-1), and a cycloalkylene group given by the following formula (10a-2).

The aromatic ring in the formula (10a) may be substituted by a substituent, such as a lower alkyl group having 1 to 12 carbon atoms, a lower alkoxy group having 1 to 12 carbon atoms, an ester group, a hydroxy group, a nitro group, a halogen, or a cyano group. The formulas (10a-1) and (10a-2) are as follows:

[Formula 24]

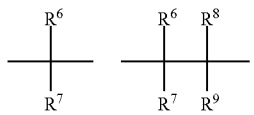

(10a-1)

wherein $R^6$, $R^7$, $R^8$, and $R^9$ are each independently any selected from the group consisting of a hydrogen atom, a lower alkyl group having 1 to 12 carbon atoms, a cycloalkyl group, an aryl group, and an aralkyl group, and may be substituted by a halogen atom or an alkoxy group; and

[Formula 25]

(10a-2)

wherein k is an integer of 3 to 11, and the hydrogen atom in —CH$_2$— may be substituted by a lower alkyl group having 1 to 12 carbon atoms, an aryl group, a halogen atom, or the like.

Examples of $Ar^{11}$ in the above formula (10) include a naphthyl group and various substituted naphthyl groups, such as naphthyl (isomers), methylnaphthyl (isomers), dimethylnaphthyl (isomers), chloronaphthyl (isomers), methoxynaphthyl (isomers), and cyanonaphthyl (isomers); and various substituted and unsubstituted hetero aromatic groups, such as pyridine (isomers), coumaryl (isomers), quinolyl (isomers), methylpyridyl (isomers), chloropyridyl (isomers), methylcoumaryl (isomers), and methylquinolyl (isomers).

Examples of the aromatic monohydroxy compound given by the above formula (10) include phenols, various alkylphenols, such as, cresol (isomers), xylenol (isomers), trimethylphenol (isomers), tetramethylphenol (isomers), ethylphenol (isomers), propylphenol (isomers), butylphenol (isomers), diethylphenol (isomers), methylethylphenol (isomers), methylpropylphenol (isomers), dipropylphenol (isomers), methylbutylphenol (isomers), pentylphenol (isomers), hexylphenol (isomers), and cyclohexylphenol (isomers); various alkoxyphenols, such as methoxyphenol (isomers) and ethoxyphenol (isomers); and various substituted phenols represented by the formula (10-1):

[Formula 26]

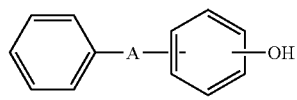

(10-1)

A and the aromatic ring in the above formula (10-1) have the same meaning as in the formula (10a).

For example, naphthol (isomers) and various substituted naphthols; and hetero aromatic monohydroxy compounds, such as hydroxypyridine (isomers), hydroxycoumarin (isomers), and hydroxyquinoline (isomers) are also used as the aromatic monohydroxy compound given by the above formula (10).

The above aromatic monohydroxy compound is preferably an aromatic monohydroxy compound of the above formula (10) where $Ar^{11}$ represents an aromatic group having 6 to 10 carbon atoms, particularly preferably a phenol.

(Transesterification Reaction)

A transesterification reaction as given by the following formula (a) is performed using the above-described dialkyl carbonate and aromatic monohydroxy compound, in the presence of the reaction catalyst described later, and the alkylaryl carbonate can be obtained. The formula (a) is as follows:

[Formula 27]

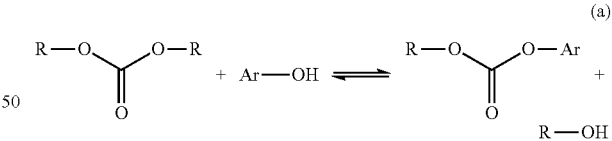

(a)

wherein R represents an alkyl group, and Ar represents an aryl group.

(Alkylaryl Carbonate)

The alkylaryl carbonate obtained in the above step (1) is preferably a compound represented by the formula (11):

[Formula 28]

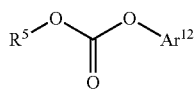

(11)

wherein $R^5$ represents a linear or branched aliphatic group having 1 to 12 carbon atoms, or an alicyclic aliphatic group having 5 to 12 carbon atoms, and $Ar^{12}$ represents an unsubstituted or substituted aryl group having 6 to 20 carbon atoms.

$R^5$ and $Ar^{12}$ correspond to $R^4$ in the above-described dialkyl carbonate and $Ar^{11}$ in the above-described aromatic monohydroxy compound, respectively.

Examples of the alkylaryl carbonate as described above include methyl phenyl carbonate, ethyl phenyl carbonate, propyl phenyl carbonate (isomers), butyl phenyl carbonate (isomers), pentyl phenyl carbonate (isomers), hexyl phenyl carbonate (isomers), heptyl phenyl carbonate (isomers), octyl phenyl carbonate (isomers), octyl tolyl carbonate (isomers), nonyl (ethylphenyl)carbonate (isomers), decyl(butylphenyl) carbonate (isomers), methyl tolyl carbonate (isomers), ethyl tolyl carbonate (isomers), propyl tolyl carbonate (isomers), butyl tolyl carbonate (isomers), allyl tolyl carbonate (isomers), methyl xylyl carbonate (isomers), methyl (trimethylphenyl)carbonate (isomers), methyl (chlorophenyl)carbonate (isomers), methyl (nitrophenyl) carbonate (isomers), methyl (methoxyphenyl)carbonate (isomers), methyl cumyl carbonate (isomers), methyl (naphthyl)carbonate (isomers), ethyl cumyl carbonate (isomers), methyl (benzoylphenyl)carbonate (isomers), and ethyl xylyl carbonate (isomers).

Among these alkylaryl carbonates, alkylaryl carbonates of the above formula (11) where $R^5$ represents an alkyl group having 1 to 6 carbon atoms, such as methyl, ethyl, propyl (isomers), butyl (isomers), pentyl (isomers), or hexyl (isomers), and $Ar^{12}$ represents an aromatic group having 6 to 10 carbon atoms are preferred.

The metal atoms in the above metal-containing catalyst composition in the above step (1) preferably have a content of 0.0001 to 20% by mass, more preferably 0.001 to 15% by mass, and further preferably 0.01 to 10% by mass. When the metal atoms in the above metal-containing catalyst composition have a content in the above range, the flowability of the composition tends to be good. In the present embodiment, the content of the metal atoms in the metal-containing catalyst composition can be obtained by a method described in Examples described later.

In the above step (1), the reaction temperature is preferably 150 to 300° C., more preferably 160 to 270° C., and further preferably 180 to 250° C. The reaction pressure is preferably 0.1 to 2.0×10$^7$ Pa, more preferably 0.5 to 1.0×10$^7$ Pa, and further preferably 1 to 5.0×10$^6$ Pa. The reaction time is preferably 0.05 to 50 hr, more preferably 0.1 to 35 hr, and further preferably 0.2 to 25 hr.

Such reaction conditions are preferred in terms of a control of reaction conditions in industrial production.

[Step (2)]

The step (2) is the step of subjecting the alkylaryl carbonate obtained in the above-described step (1) to a transesterification or disproportionation reaction so as to obtain a reaction product including the diaryl carbonate. The transesterification reaction is a reaction as given by the following formula (a'), in which the above alkylaryl carbonate and the aromatic monohydroxy compound further react with each other so as to produce the diaryl carbonate and an alcohol. The transesterification reaction is usually performed in the presence of the reaction catalyst described later, as in the transesterification reaction in the above-described step (1). The formula (a') is as follows:

[Formula 29]

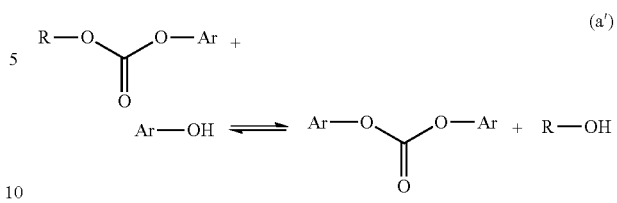

The disproportionation reaction is a reaction as given by the following formula (b), and is usually performed in the presence of the reaction catalyst described later. The formula (b) is as follows:

[Formula 30]

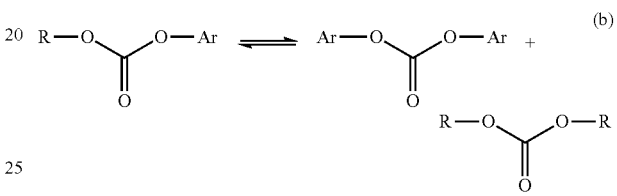

wherein R represents an alkyl group, and Ar represents an aryl group.

The alcohol as by-product by the reactions given by the above formulas (a) and/or (a') may be recovered for recycling and is preferably used for the synthesis of the dialkyl carbonate. The aliphatic carbonate is obtained by a conventional known method.

In terms of the effective use of the compounds, it is preferred that the aliphatic carbonate produced by the reaction given by the above formula (b) is recovered for recycling, recirculated, and used again for the reaction given by the above formula (a).

In other words, for example, it is preferred to add a step of mainly performing the transesterification reactions given by the above formulas (a) and (a') in a first reactor, then feeding the reaction solution comprising the alkylaryl carbonate and/or the diaryl carbonate removed from the first reactor, to a second reactor, as it is, or after removing the starting material and the reactant, mainly performing the disproportionation reaction given by the above formula (b) so as to produce the useful diaryl carbonate, removing the dialkyl carbonate produced as by-product at the time, in a gas state, by distillation, from the upper portion of the distillation column, and reusing the dialkyl carbonate as the starting material in the above formula (a) after purifying it if necessary.

(Diaryl Carbonate)

The diaryl carbonate obtained in the step (2) is preferably a compound represented by the formula (12):

[Formula 31]

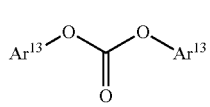

wherein $Ar^{13}$ represents an unsubstituted or substituted aryl group having 6 to 20 carbon atoms. $Ar^{13}$ corresponds to the $Ar^{12}$ of the above-described alkylaryl carbonate.

Examples of the diaryl carbonate given by the above formula (12) include a diaryl carbonate in which $R^5$ in the alkylaryl carbonate having the above-described $R^5$ and $Ar^{12}$ is replaced by the above-described $Ar^{12}$.

Specific examples of the above diaryl carbonate include diphenyl carbonate, ditolyl carbonate, di(ethylphenyl)carbonate, di(butylphenyl)carbonate, dixylyl carbonate, di(trimethylphenyl)carbonate, di(chlorophenyl)carbonate, di(nitrophenyl)carbonate, di(methoxyphenyl)carbonate, dicumyl carbonate, dinaphthyl carbonate, and dibenzoylphenyl carbonate. Among these diaryl carbonates, particularly, those in which $Ar^{13}$ is an aromatic group having 6 to 10 carbon atoms are preferred, and diphenyl carbonate is more preferred.

The metal atoms in the above metal-containing catalyst composition in the above step (2) preferably have a content of 0.0001 to 20% by mass, more preferably 0.001 to 15% by mass, and further preferably 0.01 to 10% by mass. When the metal atoms in the above metal-containing catalyst composition have a content in the above range, the flowability of the composition tends to be good.

In the above step (2), the reaction temperature is preferably 150 to 300° C., more preferably 160 to 270° C., and further preferably 180 to 250° C. The reaction pressure is preferably 0.1 to $2.0 \times 10^7$ Pa, more preferably 0.5 to $1.0 \times 10^7$ Pa, and further preferably 1 to $5.0 \times 10^6$ Pa. The reaction time is preferably 0.05 to 50 hr, more preferably 0.1 to 35 hr, and further preferably 0.2 to 25 hr.

Such reaction conditions are preferred in terms of a control of reaction conditions in industrial production.

[Step (3)]

The step (3) is the step of distilling the reaction product obtained in the above step (2) to separate the reaction product into a low boiling component including the diaryl carbonate and a high boiling component including the reaction catalyst.

The distillation in the step (3) is preferably performed by a distillation column. The distillation column preferably has a temperature of 150 to 300° C., more preferably 160 to 270° C., and further preferably 180 to 250° C., at a column bottom. Further, the distillation column preferably provides a residence time of 0.02 to 100 hr, more preferably 0.05 to 80 hr, and further preferably 0.1 to 50 hr, at a column bottom.

The low boiling component separated in the above step (3) includes, for example, the unreacted alkylaryl carbonate, in addition to the diaryl carbonate.

The high boiling component separated in the above step (3) usually includes a component having a higher boiling point than that of the diaryl carbonate, but may include the remaining diaryl carbonate that cannot be separated.

When the high boiling component separated in the above step (3) is 100% by mass, the high boiling component includes 70% by mass or less, preferably 60% by mass or less, and more preferably 50% by mass or less, of the component having the higher boiling point than that of the diaryl carbonate. The lower limit of the content of the component having the higher boiling point than that of the diaryl carbonate is not particularly limited, but is, for example, 0.1% by mass or more.

The content of the component having the higher boiling point than that of the diaryl carbonate can be obtained by a method described in (Quantitative Analysis of Compounds of Formula (1)) described later.

The high boiling component separated in the above step (3) includes a compound represented by the formula (1):

[Formula 32]

(1)

wherein $Ar^1$ represents an unsubstituted or substituted arylene group having 6 to 20 carbon atoms, X and Y—O are located at an ortho position to each other, X represents a hydroxy group or a substituent given by the formula (2) or (3), and Y represents hydrogen or a substituent given by the formula (3). The formulas (2) and (3) are as follows:

[Formula 33]

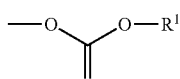

(2)

[Formula 34]

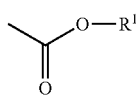

(3)

wherein $R^1$ represents a linear or branched aliphatic group having 1 to 12 carbon atoms, an alicyclic aliphatic group having 5 to 12 carbon atoms, or an unsubstituted or substituted aryl group having 6 to 20 carbon atoms.

Examples of the above $Ar^1$ include a phenylene group and various alkylphenylene groups, such as phenylene, methylphenylene (isomers), dimethylphenylene (isomers), trimethylphenylene (isomers), tetramethylphenylene, ethylphenylene (isomers), diethylphenylene (isomers), methylethylphenylene (isomers), pentylphenylene (isomers), hexylphenylene (isomers), and cyclohexylphenylene (isomers); various alkoxyphenylene groups, such as methoxyphenylene (isomers), ethoxyphenylene (isomers), and butoxyphenylene (isomers); various halogenated phenylene groups, such as fluorophenylene (isomers), chlorophenylene (isomers), bromophenylene (isomers), chloro(methyl)phenylene (isomers), and dichlorophenylene (isomers); various substituted phenylene groups given by the following formula (1a); and a naphthylene group and various substituted naphthylene groups, such as naphthylene (isomers), methylnaphthylene (isomers), dimethylnaphthylene (isomers), chloronaphthylene (isomers), methoxynaphthylene (isomers), and cyanonaphthylene (isomers).

$R^1$ corresponds to the $R^5$ or $Ar^{12}$ of the above-described alkylaryl carbonate. The formula (1a) is as follows:

[Formula 35]

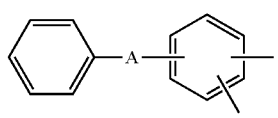

(1a)

wherein A represents any divalent group selected from the group consisting of a single bond, —O—, —S—, —CO—, —$SO_2$—, an alkylene group or a substituted alkylene group given by the following formula (1a-1), and a cycloalkylene group given by the following formula (1a-2), and the aromatic ring may be substituted by a substituent, such as a lower alkyl group, a lower alkoxy group, an ester group, a hydroxy group, a nitro group, a halogen, or a cyano group. The formulas (1a-1) and (1a-2) are as follows:

[Formula 36]

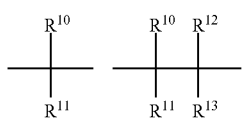
(1a-1)

wherein $R^{10}$, $R^{11}$, $R^{12}$, and $R^{13}$ are each independently a hydrogen atom, a lower alkyl group, a cycloalkyl group, an aryl group, or an aralkyl group, and may be substituted by a halogen atom or an alkoxy group; and

[Formula 37]

(1a-2)

wherein k is an integer of 3 to 11, and the hydrogen atom may be substituted by a lower alkyl group, an aryl group, a halogen atom, or the like.

The compound represented by the above formula (1) is preferably at least one selected from a group of compounds represented by the following formulas (4) to (8):

[Formula 38]

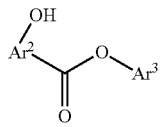
(4)

wherein $Ar^2$ represents an unsubstituted or substituted arylene group having 6 to 20 carbon atoms, $Ar^3$ represents an unsubstituted or substituted aryl group having 6 to 20 carbon atoms, and two substituents on $Ar^2$ are located at an ortho position to each other;

[Formula 39]

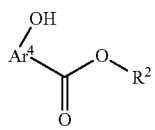
(5)

wherein $Ar^4$ represents an unsubstituted or substituted arylene group having 6 to 20 carbon atoms, $R^2$ represents a linear or branched aliphatic group having 1 to 12 carbon atoms, or an alicyclic aliphatic group having 5 to 12 carbon atoms, and two substituents on $Ar^4$ are located at an ortho position to each other;

[Formula 40]

(6)

wherein $Ar^5$ represents an unsubstituted or substituted arylene group having 6 to 20 carbon atoms, and two hydroxy groups on $Ar^5$ are located at an ortho position to each other;

[Formula 41]

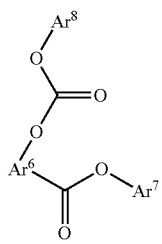
(7)

wherein $Ar^6$ represents an unsubstituted or substituted arylene group having 6 to 20 carbon atoms, $Ar^7$ and $Ar^8$ each independently represent an unsubstituted or substituted aryl group having 6 to 20 carbon atoms, and two substituents on $Ar^6$ are located at an ortho position to each other; and

[Formula 42]

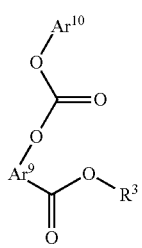
(8)

wherein $Ar^9$ represents an unsubstituted or substituted arylene group having 6 to 20 carbon atoms, $Ar^{10}$ represents an unsubstituted or substituted aryl group having 6 to 20 carbon atoms, $R^3$ represents a linear or branched aliphatic group having 1 to 12 carbon atoms, or an alicyclic aliphatic group having 5 to 12 carbon atoms, and two substituents on $Ar^9$ are located at an ortho position to each other.

There are a case where the compound given by the above formula (1) is produced by a reaction of the raw material with an oxidizing substance, and a case where the compound given by the above formula (1) is produced as by-product by an occurrence of a Fries rearrangement reaction in the presence of the metal-containing catalyst composition.

(Production by Reaction of Raw Material with Oxidizing Substance)

The case where the compound given by the above formula (1) is produced by the reaction of the raw material with an oxidizing substance will be described.

For example, when the aromatic monohydroxy compound that is the raw material in the step (1) coexists with an oxidizing substance, such as oxygen, the aromatic monohydroxy compound changes to an aromatic dihydroxy compound, as given by the following formula (c). This aromatic dihydroxy compound corresponds to the compound represented by the above formula (1) where X represents a hydroxy group, and Y represents hydrogen. The formula (c) is as follows:

[Formula 43]

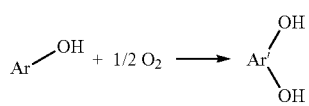
(c)

wherein Ar represents an unsubstituted or substituted aryl group having 6 to 20 carbon atoms, and Ar' has two hydroxy groups at an ortho position and represents an unsubstituted or substituted arylene group having 6 to 20 carbon atoms.

The aromatic dihydroxy compound produced as by-product by coexistence with the oxidizing substance, such as oxygen, as described above, further reacts with the dialkyl carbonate, the alkylaryl carbonate, or the diaryl carbonate, and changes to aromatic carbonates, as given by the following formulas (d) and (e).

The compounds obtained by the formulas (d) and (e) correspond to the compounds represented by the above formula (1) where X represents a hydroxy group or a substituent given by the formula (2), and Y represents hydrogen or a substituent given by the formula (3). The formulas (d) and (e) are as follows:

[Formula 44]

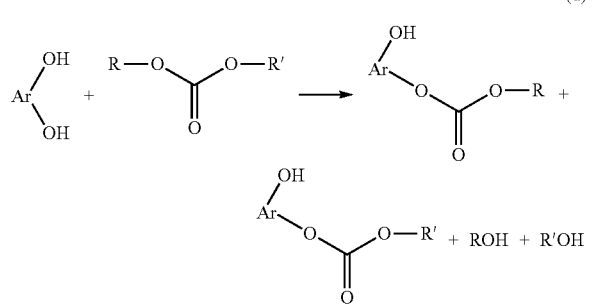
(d)

wherein Ar represents an arylene group having substituents at an ortho position to each other, and R and R' represent an alkyl group or an aryl group; and

[Formula 45]

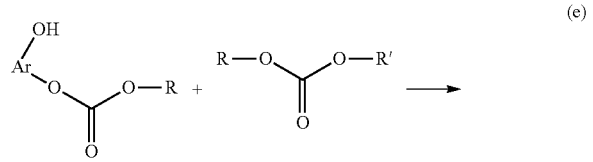
(e)

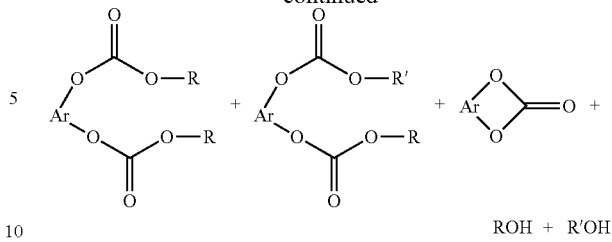

wherein Ar represents an arylene group having substituents at an ortho position to each other, and R and R' represent an alkyl group or an aryl group.

(Production by Fries Rearrangement Reaction)

The case where the compound given by the above formula (1) is produced as by-product by a Fries rearrangement reaction in the presence of the metal-containing catalyst composition will be described.

The metal-containing catalyst composition described later has a function of significantly improving the reaction rate of the transesterification reaction and the disproportionation reaction, and an improvement in the productivity of the diaryl carbonate is intended.

However, a side reaction due to Fries rearrangement given by the following formulas (f) and (g) occurs in the presence of the metal-containing catalyst composition. The formula (f) is as follows:

[Formula 46]

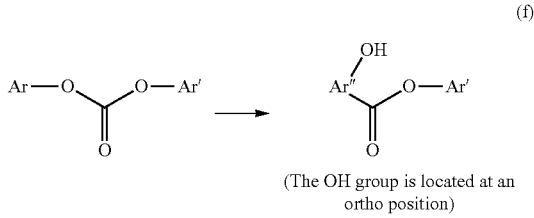
(f)

(The OH group is located at an ortho position)

wherein Ar and Ar' represent an aryl group, and Ar" represents an arylene group.

The salicylate ester produced by the above formula (f) is generally the compound represented by the above-described formula (4). The formula (g) is as follows:

[Formula 47]

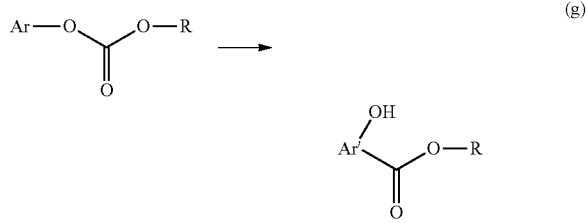
(g)

(The OH group is located at an ortho position)

wherein R represents an alkyl group, Ar represents an aryl group, and Ar' represents an arylene group.

The salicylate ester produced by the reaction of the formula (g) is generally the compound represented by the above-described formula (5).

The production of the salicylate ester by the side reaction described above increases as the temperature of the environment increases. Further, the salicylate ester has a high boiling point, and therefore is not separated by distillation from the metal-containing catalyst composition similarly having a high boiling point. As a result, the salicylate ester easily coexists with the metal-containing catalyst composition.

The above-described salicylate ester corresponds to the compound represented by the above formula (1) where X represents the above formula (3), and Y represents hydrogen.

Such a salicylate ester reacts with the dialkyl carbonate, the alkylaryl carbonate, or the diaryl carbonate so as to produce a salicylate ester carbonate, as given by the following formula (h).

The salicylate ester carbonate produced in this manner corresponds to the compound represented by the above formula (1) where X represents the above formula (3), and Y represents the above formula (3). The formula (h) is as follows:

[Formula 44]

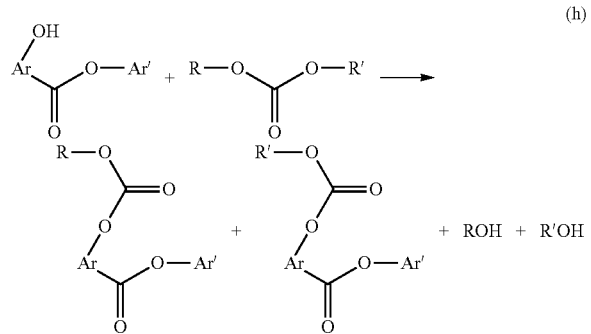

wherein Ar represents an arylene group having substituents at an ortho position to each other, R and R' represent an alkyl group or an aryl group, and Ar' represents an aryl group.

If a large amount of the aromatic dihydroxy compounds produced as described above and the aromatic carbonates derived from the aromatic dihydroxy compounds coexist with the metal-containing catalyst composition, generally, the productivity of the originally targeted diaryl carbonate decreases significantly.

Further, the salicylate esters produced by the above-described Fries rearrangement reaction also generally cause a significant decrease in the productivity of the originally targeted diaryl carbonate.

However, in the method for producing the diaryl carbonate according to the present embodiment, the diaryl carbonate that is the target product can be stably produced, while maintaining high productivity, by performing control so that the compounds given by (i) to (iii) described later, such as aromatic dihydroxy compounds, aromatic carbonates derived from the aromatic dihydroxy compounds, and salicylate esters, satisfy the conditions of (iv) to (vi) described later, respectively.

In other words, the present inventors consider that the ratio of a particular compound produced as by-product by the reaction of the raw material with the oxidizing substance or the Fries rearrangement reaction during the step to the metal-containing catalyst composition affects the productivity of the diaryl carbonate.

[Step (4)]

The step (4) is the step of recycling the high boiling component separated in the above step (3) into the above steps (1) and/or (2).

The high boiling component recycled in the above step (4) includes compounds given by (i) to (iii):

(i) a compound of the above formula (1) where X represents the above formula (2) or (3), and Y represents the above formula (3);

(ii) a compound of the above formula (1) where X represents a hydroxy group, and Y represents the above formula (3), and/or a compound of the above formula (1) where X represents the above formula (3), and Y represents hydrogen; and (iii) a compound of the above formula (1) where X represents a hydroxy group, and Y represents hydrogen.

The compounds of (i) to (iii) satisfy conditions given by (iv) to (vi), respectively:

(iv) "the total moles of the compounds of (i)/the moles of metal atoms" is 0.005 to 20;

(v) "the total moles of the compounds of (ii)/the moles of metal atoms" is 0.005 to 4; and (vi) "the moles of the compound of (iii)/the moles of metal atoms" is less than 2.

A preferred condition of (iv) will be described.

"The total moles of the compounds of (i)/the moles of metal atoms" is preferably 0.005 to 10, more preferably 0.005 to 5.

A preferred condition of (v) will be described.

"The total moles of the compounds of (ii)/the moles of metal atoms" is preferably 0.005 to 3, more preferably 0.005 to 2.5.

A preferred condition of (vi) will be described.

"The moles of the compound of (iii)/the moles of metal atoms" is preferably less than 1.7, more preferably less than 1.5. The lower limit of "the moles of the compound of (iii)/the moles of metal atoms" is not particularly limited, but is, for example, 0.001 or more.

The high boiling component recycled in the above step (4) preferably has "total moles of the compounds represented by the above formula (1)/moles of metal atoms" from 0.005 to 10, more preferably from 0.005 to 5, and further preferably from 0.005 to 4.

In the step of continuously producing the diaryl carbonate, the compounds represented by the formula (1) are produced as by-products and accumulated, and thus, the productivity of the diaryl carbonate decreases. Therefore, while the metal-containing catalyst composition and the compounds represented by the formula (1) included in the distillation residue are circulated, part of them are removed, and the metal-containing catalyst composition or a composition A described later is fed to the production step, so that production is performed in an environment adapted to satisfy the above-described conditions (iv) to (vi), in order to stably ensure the productivity of the diaryl carbonate. In the continuous production of the diaryl carbonate, the amount of the accumulated compounds represented by the formula (1) may be small at the initial stage, but it is also possible to previously add the compounds represented by the formula (1) to the metal-containing catalyst composition included in the distillation residue and circulate them into the step of producing the diaryl carbonate so as to satisfy the above-described conditions (iv) to (vi).

At the time of the start of the continuous production, the by-products are not accumulated yet, and therefore, the above-described conditions (iv) to (vi) are satisfied. However, in order to stably produce the diaryl carbonate in the continuous production step over a long time, it is necessary to continuously satisfy the above-described conditions (iv) to (vi).

As a specific example of the method for controlling the conditions (iv) to (vi), a case where the compound represented by the above formula (1) is a salicylate ester will be described below.

In the present embodiment, when the targeted diaryl carbonate and the alkylaryl carbonate produced in an intermediate step (hereinafter also simply described as "products") coexist with a high concentration of the metal-containing catalyst composition, or are placed at high temperature for a long time in the coexistence of the metal-containing catalyst composition, a large amount of a salicylate ester is produced.

For the case where the products coexist with a high concentration of the metal-containing catalyst composition, for example, a case as described below is considered.

In a step of producing a diaryl carbonate, using a metal-containing catalyst composition, generally, a mixture of products and the metal-containing catalyst composition is separated by distillation or the like, and the metal-containing catalyst composition included in the distillation residue is circulated and reused. At that time, part of the products coexist with a high concentration of the metal-containing catalyst composition in a recovery portion of a distillation column.

When the alkylaryl carbonate and the diaryl carbonate coexist with a high concentration of the metal-containing catalyst composition in this manner, an environment in which a large amount of a salicylate ester is easily produced is provided. Therefore, in order to suppress the production of the salicylate ester and satisfy the above conditions (iv) to (vi), it is necessary to control the metal-containing catalyst composition concentration, the reaction temperature, and the residence time in each step.

Specifically, in the step of separating the products and concentrating the metal-containing catalyst composition included in the distillation residue, the concentration of the metal-containing catalyst composition is adjusted to be preferably 20% by mass or less, more preferably 10% by mass or less, in the distillation residue liquid. The lower limit of the concentration of the metal-containing catalyst composition is preferably 0.05% by mass.

As another specific example of the method for controlling the above conditions (iv) to (vi), a case where the compound represented by the above formula (1) is an aromatic dihydroxy compound will be described.

It is considered that the aromatic dihydroxy compound is produced particularly by a mixing of oxygen into the raw material from air. Therefore, for example, when the raw material is previously purified by distillation and then stored in a nitrogen atmosphere in order to prevent the mixing of oxygen, the production of the aromatic dihydroxy compound can be suppressed. An amount of oxygen contained in all raw materials applied in the production step is preferably 500 ppm or less, more preferably 50 ppm or less.

(Quantitative Analysis of Compounds of Formula (1))

In the method for producing the diaryl carbonate according to the present embodiment, the compounds represented by the above formula (1) produced as by-products may form stable complexes with a metal component contained in the reaction catalyst. Then, the quantitative analysis of the compounds represented by the above formula (1) is inaccurate, and as a result, a problem is that the molar ratio of the compounds represented by the above formula (1) to metal atoms (the compounds represented by the formula (1)/metal atoms) is not accurately obtained.

As described above, it is important to perform accurate quantitative analysis of the mixture comprising the compounds represented by the above formula (1) and the metal-containing catalyst composition and accurately obtain the molar ratio of the compounds represented by the above formula (1) to metal atoms (the compounds represented by the formula (1)/metal atoms).

Specific examples of the method for performing accurate quantitative analysis of the molar ratio of the compounds represented by the above formula (1) to metal atoms (the compounds represented by the formula (1)/metal atoms) include a method for adding an additive for dissociating the above complexes (the compounds represented by the above formula (1)) to the mixture comprising the compounds represented by the above formula (1) produced and the metal-containing catalyst composition, performing treatment, such as filtration, as required, and performing quantitative analysis by gas chromatography, high performance liquid chromatography, or the like which uses a general analysis apparatus, in the method for producing the diaryl carbonate.

The above additive is selected according to the type of the reaction catalyst. Examples of the above additive include a monodentate or polydentate ligand capable of coordination to the metal atoms, specifically, water, polyhydroxy compounds, nitrogen-containing heterocyclic compounds, sulfur-containing heterocyclic compounds, fluorine-substituted alcohols, and fluorine-substituted organic acids, and preferably, water, catechol, phenanthroline, hexafluoroisopropanol, and trifluoroacetic acid.

The method for producing the diaryl carbonate according to the present embodiment preferably further comprises the step of sampling the high boiling component recycled in the above step (4), adding a monodentate or polydentate ligand capable of coordination to the metal atoms, to the above sampled high boiling component at 1 equivalent or more, preferably 3 equivalents or more, with respect to the metal atoms therein so as to prepare an analysis sample, and analyzing the analysis sample to quantify the compounds given by (i) to (iii) included in the above high boiling component. Specifically, the method for producing the diaryl carbonate according to the present embodiment preferably further comprises the step of sampling the high boiling component recycled in the above step (4), adding at least one additive to the above sampled high boiling component at 1 equivalent or more, preferably 3 equivalents or more, with respect to the metal atoms therein so as to prepare an analysis sample, the additive being selected from the group consisting of water, polyhydroxy compounds, nitrogen-containing heterocyclic compounds, sulfur-containing heterocyclic compounds, fluorine-substituted alcohols, and fluorine-substituted organic acids, and analyzing the analysis sample by gas or liquid chromatography to quantify the compounds given by (i) to (iii) included in the above high boiling component.

The method for producing the diaryl carbonate in the present embodiment preferably further comprises the step of performing control so that the compounds given by (i) to (iii) included in the high boiling component recycled in the above step (4) satisfy the conditions of (iv) to (vi), respectively, after the step of quantifying the compounds given by (i) to (iii).

Examples of the step of performing control so that the conditions of (iv) to (vi) are satisfied include the step of controlling the metal-containing catalyst composition concentration, the reaction temperature, and the residence time, and include the step of preventing the mixing of oxygen into the raw material from air particularly when the compound represented by the formula (1) is an aromatic dihydroxy compound, as described above.

[Reaction Catalyst]

The reaction catalyst used in the present embodiment is a metal-containing catalyst composition. The metal-containing catalyst composition is preferably a metal-containing catalyst composition that is dissolved in the reaction solution or present in a liquid state, and is preferably a metal-containing catalyst composition having at least one metal-oxygen-carbon linkage.

In the metal-containing catalyst composition used in the present embodiment, the metal portion is preferably a Group 4, 5, 8, 13, or 14 metal of the periodic table, more preferably at least one metal selected from the group consisting of Ti, V, Zr, Fe, Al, and Sn. These have high catalytic activity and are preferred from a practical perspective.

The metal-containing catalyst composition is preferably an alkyloxy metal composition having an alkoxy group or an aryloxy metal composition having an aryl group. The metal-containing catalyst composition is preferably a titanium-containing catalyst composition. The titanium-containing catalyst composition will be described in detail later.

The metal-containing catalyst composition used in the present embodiment preferably comprises at least one selected from compounds represented by the following formulas (D1), (D2), and (D3):

[Formula 49]

$$M^{n+}Q_m \quad (D1)$$

wherein M represents zirconium, iron, or aluminum, Q represents an alkoxy group or an aryloxy group, n represents the valence of the metal M, m and n are each an integer of 1 or more, and m=n;

[Formula 50]

$$Z_jSnO_kT_l \quad (D2)$$

wherein Sn represents tin, Z represents an alkyl group, O represents an oxygen atom, T represents an alkoxy group or an aryloxy group, k is an integer of 0 or 1, j and l are each an integer of 1 to 4, and j+2k+l=4; and

[Formula 51]

$$VO_sL_t \quad (D3)$$

wherein V represents vanadium, O represents oxygen, L represents an alkoxy group or an aryloxy group, s is an integer of 0 or 1, t is an integer of 3 to 5, and 2s+t=5.

The alkoxy group and the aryloxy group in the above formulas (D1) to (D3) are the same as the alkoxy group and the aryloxy group of the titanium-containing catalyst composition described later.

Specific examples of the zirconium-containing catalyst composition include tetramethoxyzirconium, tetraethoxyzirconium, tetrapropoxyzirconium (isomers), tetrabutoxyzirconium (isomers), and tetraphenoxyzirconium.

Specific examples of the iron-containing catalyst composition include trimethoxyiron, triethoxyiron, tripropoxyiron (isomers), tributoxyiron (isomers), and triphenoxyiron.

Specific examples of the aluminum-containing catalyst composition include trimethoxyaluminum, triethoxyaluminum, tripropoxyaluminum (isomers), tributoxyaluminum (isomers), and triphenoxyaluminum.

Specific examples of the tin-containing catalyst composition include tin tetramethoxide, tin tetrabutoxide, tin tetraphenoxide, monobutyltin oxide methoxide, monobutyltin oxide ethoxide, monobutyltin oxide propoxide (isomers), monobutyltin butoxide (isomers), monobutyltin pentoxide (isomers), monobutyltin phenoxide, monooctyltin oxide methoxide, monooctyltin oxide ethoxide, monooctyltin oxide propoxide (isomers), monooctyltin butoxide (isomers), monooctyltin pentoxide (isomers), monooctyltin phenoxide, dibutyltin dimethoxide, dibutyltin diethoxide, dibutyltin dipropoxide (isomers), dibutyltin dibutoxide (isomers), dibutyltin dipentoxide (isomers), dibutyltin diphenoxide (isomers), dioctyltin dimethoxide, dioctyltin diethoxide, dioctyltin dipropoxide (isomers), dioctyltin dibutoxide (isomers), dioctyltin dipentoxide (isomers), and dioctyltin diphenoxide (isomers).

Specific examples of the vanadium-containing catalyst composition include vanadium pentamethoxide, vanadium pentaethoxide, vanadium pentapropoxide (isomers), vanadium pentabutoxide (isomers), vanadium oxide trimethoxide, vanadium oxide triethoxide, vanadium oxide tripropoxide (isomers), and vanadium oxide tributoxide (isomers).

For the above-described metal-containing catalyst, those containing two or more types of metals can also be applied.

The titanium-containing catalyst composition, among the metal-containing catalyst compositions used in the present embodiment, will be described in detail as an example below.

The titanium-containing catalyst composition is preferably an organic oxytitanium composition having at least one R—O—Ti linkage, wherein R represents an organic group containing 1 to 20 carbon atoms. The titanium-containing catalyst composition is preferably dissolved in the reaction solution or present in a liquid state. The titanium-containing catalyst composition is preferably an alkyloxytitanium composition and/or an aryloxytitanium composition described later. Further, the titanium-containing catalyst composition used in the present embodiment is more preferably a titanium-containing composition formed of a diaryl carbonate and an aryloxytitanium composition. As described above, the above steps (1) and/or (2) is usually performed in the presence of the reaction catalyst.

An amount of the titanium-containing catalyst composition used to carry out the method for producing the diaryl carbonate in the present embodiment varies depending on various conditions, such as a type of the reaction catalyst, raw materials and an amount ratio of the raw materials, reaction temperature, and reaction pressure, but is preferably 0.0001 to 50% by mass, more preferably 0.001 to 30% by mass based on the total mass of the raw materials.

The titanium-containing catalyst composition will be described in detail below.

(Titanium-Containing Catalyst Composition)

The titanium-containing catalyst composition usually promotes the transesterification reaction in the step (1) and the transesterification or disproportionation reaction in the step (2). The titanium-containing catalyst composition used in the present embodiment is preferably an organic oxytitanium composition having at least one R—O—Ti linkage.

(Organic Oxytitanium Composition Having R—O—Ti Linkage)

The organic oxytitanium composition having the R—O—Ti linkage is an organic oxytitanium composed of a tetravalent Ti atom, in which the Ti atom is substituted by an R—O— group, wherein R represents an organic group.

Here, the "organic oxytitanium composition having the R—O—Ti linkage" means that not only one "organic oxytitanium having an R—O—Ti linkage" is present, but also a plurality of "organic oxytitaniums having an R—O—Ti linkage" may be mixed. This is due to the fact that it is difficult to exactly identify the structure.

The organic oxytitanium composition may be a monomer or may be a polymer (organic polytitanoxane).

The "polytitanoxane" herein refers to an organic-inorganic hybrid compound comprising a Ti—O—Ti repeating structure and an R—O—Ti linkage, wherein R represents an organic group. The Ti atom constituting the polytitanoxane is preferably tetravalent.

For the structure of the polytitanoxane, there are reports in which the structure is presumed (for example, Kogyo Kagaku Zasshi (Journal of the Chemical Society of Japan, Industrial Chemistry Section), vol. 64, p. 885-888 (1961), and Nature, p. 273-274 (1961)), and reports in which a particular linkage (for example, Ti—O—Ti) is allegedly detected (for example, Japanese Patent Laid-Open No. 2004-256719).

The polytitanoxane used in the present embodiment is preferably a polytitanoxane comprising at least one polytitanoxane comprising a structural unit selected from the group consisting of the following general formulas (1b), (2b), (3b), and (4b). In other words, the polytitanoxane used in the present embodiment may have a structure in which the structural units given by the following formulas are combined to form a linear, branched, or cyclic structure via a Ti—O—Ti linkage between each other, or a structure comprising a combination thereof. The general formulas (1b), (2b), (3b), and (4b) are as follows:

[Formula 52]

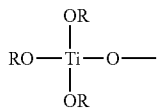

(1b)

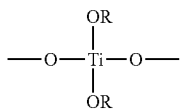

(2b)

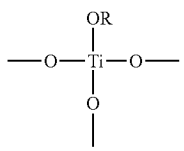

(3b)

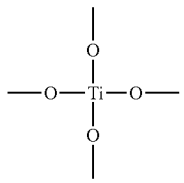

(4b)

In the above formulas (1b) to (4b), R represents an organic group.

The R group is an organic group described in Nomenclature (IUPAC Nomenclature of Organic Chemistry) prescribed by IUPAC (The International Union of Pure and Applied Chemistry).

A plurality of R groups are contained in the above organic polytitanoxane. They may be the same or different.

For the structure forming a branched or cyclic structure, for example, those shown in the following formulas (1c) and (2c) are considered.

[Formula 53]

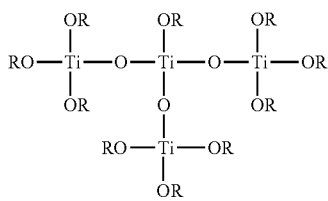

(1c)

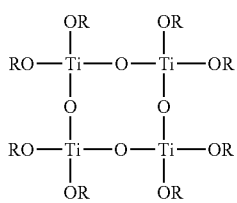

(2c)

When the IUPAC Rules, and the Nomenclature Rules prescribed by IUPAC also shown hereinafter (except for cases where other years' IUPAC Recommendations and the like are specially cited) herein are cited below, "Yukikagaku•Seikagaku Meimeiho (Organic Chemical and Biochemical Nomenclature)" (revised second edition published in 1992, Nankodo Co., Ltd., Japan) is cited, which is based on the edition including all the rules of organic chemistry and biochemistry, and Japanese transliteration rules, published as a separate volume of "Kagaku no Ryoiki (The Area of Chemistry)" in 1980, based on Recommendations 1979, and in which all subsequent revisions and recommendations are added.

"Organic" refers to generally a group of compounds that are subjects of the nomenclature disclosed in the book.

The subjects ("organic") may be subjects described in Recommendations issued in 1993 (when it is difficult to obtain the above-described book published in Japan, Recommendations 1979 and Recommendations 1993 may be referred to).

However, the above-described "organic" compounds that are subjects of the Nomenclature also include organometallic compounds and metal complexes.

"Organic" and/or "organic groups" and/or "substituents" and the like, and the compounds used in the present embodiment will be described herein below. They are composed of an atom not including a metal atom and/or a semimetal, unless otherwise specified.

Further preferably, "organic compounds," "organic groups," and "substituents" composed of an atom selected from H (hydrogen atom), C (carbon atom), N (nitrogen atom), O (oxygen atom), and S (sulfur atom) are used in the present embodiment.

The limitations "aliphatic" and "aromatic" are frequently used herein. According to the IUPAC Rules, it is described that organic compounds are classified into aliphatic compounds and aromatic compounds, and the definition of aliphatic compounds is groups according to the aliphatic compounds based on IUPAC Recommendations 1995.

In the Recommendations, aliphatic compounds are defined as "Acyclic or cyclic, saturated or unsaturated carbon compounds, excluding aromatic compounds."

An aliphatic group often used herein is a group comprising the above aliphatic compound.

For a group, for example, the R portion obtained by removing a hydrogen atom from the aliphatic compound RH is defined as a monovalent aliphatic group.

Aliphatic and aliphatic groups include all of saturated and unsaturated, and acyclic and cyclic, and refer to the above "organic compounds," "organic groups," and "substituents" composed of an atom selected from H (hydrogen atom); C (carbon atom); N (nitrogen atom); O (oxygen atom); S (sulfur atom); Si (silicon atom); and a halogen atom selected from Cl (chlorine atom), Br (bromine atom), and I (iodine atom).

A case where an aromatic group is bonded to an aliphatic group, such as an aralkyl group, is often described as "an aliphatic group substituted by an aromatic group" or "a group comprising an aliphatic group to which an aromatic group is bonded" in such a manner.

This is based on reactivity in the present embodiment, and the nature regarding the reaction of groups, such as aralkyl groups, is extremely similar to the reactivity of aliphatic groups, rather than aromaticity.

Non-aromatic reactive groups including aralkyl groups and alkyl groups are often described as "aliphatic groups which may be aromatically substituted," "aromatically substituted aliphatic groups," "aliphatic groups to which aromatic groups are bonded," or the like.

When the general formulas of the compounds used herein are described, definitions according to the above-described Nomenclature Rules prescribed by IUPAC are used. However, in the description of the compounds used in the present embodiment, in order to clarify the feature of the structure, coined words, such as an "organic polytitanoxane" and an "aryloxytitanium," are used, and for the names of particular groups and illustrated compound names, trivial names are often used.

The number of atoms and the number of substituents are often described herein. They all represent zero or a positive integer (zero is often a positive integer). However, when a composition ratio formula is represented, positive numbers are used.

This is notation often used for the notation of inorganic compounds and organic-inorganic hybrid compounds.

The above R group is preferably a group composed of a carbon atom, a hydrogen atom, and/or an oxygen atom, and it is any of an aliphatic group, an aromatic group, and a group in which an aliphatic group and an aromatic group are bonded to each other, and it represents an acyclic hydrocarbon group, a cyclic hydrocarbon group (a group such as, for example, a monocyclic hydrocarbon group, a condensed polycyclic hydrocarbon group, a bridged cyclic hydrocarbon group, a spiro hydrocarbon group, a ring assembly hydrocarbon group, a cyclic hydrocarbon group with a side chain, a heterocyclic group, a heterocyclic spiro group, or a bridged heterocyclic group), a group in which one or more groups selected from the above acyclic hydrocarbon group and the above cyclic hydrocarbon group are bonded, and a group in which these groups are linked via covalent bonds to a particular nonmetal atom (carbon or oxygen).

The above covalent bond to the particular nonmetal atom (carbon or oxygen) refers to, for example, a state in which a group represented by the following formulas (1d) to (4d) and the above-described group are covalently bonded to each other.

[Formula 54]

(1d)

(2d)

(3d)

(4d)

Among the R groups as described above, the R group preferably used in the present embodiment is selected from the group consisting of an aliphatic group, an aromatic group, and a group in which an aliphatic group and an aromatic group are bonded to each other, considering that a side reaction is less likely to occur, and is preferably a group selected from the group consisting of an acyclic hydrocarbon group and a cyclic hydrocarbon group (a monocyclic hydrocarbon group, a condensed polycyclic hydrocarbon group, a bridged cyclic hydrocarbon group, a spiro hydrocarbon group, a ring assembly hydrocarbon group, and a cyclic hydrocarbon group with a side chain), and a group in which at least one group selected from the group is bonded (groups substituted by each other), which contain 1 to 20 carbon atoms.

Considering the flowability of the above organic oxytitanium composition having the R—O—Ti linkage, and the like, the R group is preferably a group containing 1 to 10 carbon atoms, more preferably a group containing 1 to 7 carbon atoms.

A more preferred R group is a group selected from a group in which at least one or more selected from the group consisting of an alkyl group, a cycloalkyl group, and an aryl group are bonded to each other, and a group in which at least one or more selected from the group consisting of an alkyl group, a cycloalkyl group, and an aryl group are formed via a linkage selected from the above formulas (1d) to (4d).

Examples of such an R group include a methyl group, an ethyl group, a propyl group (isomers), a butyl group (isomers), a pentyl group (isomers), a hexyl group (isomers), a heptyl group (isomers), a cyclopropyl group, a cyclobutyl group, a cyclopentyl group, a cyclohexyl group, a cycloheptyl group, a cyclopropylmethyl group, a cyclobutylmethyl group, a cyclopentylmethyl group, a cyclohexylmethyl group, a phenyl group, a phenylmethyl group, a cresyl group (isomers), a phenylethyl group, a furfuryl group, and a pyrazyl group.

A monomer structure having an $(R-O-)_4Ti$ structure, as well as the above-described various polytitanoxanes having the R—O—Ti linkage can be preferably used as the organic oxytitanium composition having the R—O—Ti linkage used in the present embodiment. It is extremely difficult to isolate the polytitanoxane for determining the structure. Therefore, in the present embodiment, a composition containing at least one or more types of polytitanoxane having the R—O—Ti linkage is intended for a polytitanoxane composition having the R—O—Ti linkage.

The above polytitanoxane composition having the R—O—Ti linkage is preferably a composition such that a mole average degree of polymerization is 1.1 or more and 12 or less. The mole average degree of polymerization is determined by the following mathematical expression (1), using the number of Ti atoms contained in an individual polytitanoxane having an R—O—Ti linkage, which constitutes the polytitanoxane composition, and the following "molar ratio".

The polytitanoxane composition comprises one or more polytitanoxanes having a different degree of polymerization (the number of Ti atoms in the molecule).

The above "molar ratio" refers to the moles of a polytitanoxane having an individual degree of polymerization with respect to the total moles of polytitanoxanes in the polytitanoxane composition.

By the above "mole average degree of polymerization," it is meant that the product of the molar ratio of a polytitanoxane having an individual degree of polymerization and the degree of polymerization is determined, and the product is integrated for all degrees of polymerization to obtain an integrated value. In other words, the question of how many Ti atoms are contained in one polytitanoxane molecule is answered as average value.

[Expression 1]

$$Pn = \sum_{l}^{z} (p_w \cdot m_w) \qquad (1)$$

In the above mathematical expression (1), Pn is a positive number representing the mole average degree of polymerization.

z represents the number of types of polytitanoxane having an R—O—Ti linkage having a different degree of polymerization contained in the polytitanoxane composition having the R—O—Ti linkage, and represents an integer of 1 or more.

$p_w$ is a positive natural number representing the number of Ti atoms contained in a polytitanoxane molecular structure w having an R—O—Ti linkage contained in the above composition.

$m_w$ is the mole fraction of the molecular structure w to the composition and satisfies the mathematical expression (2):

[Expression 2]

$$1 = \sum_{l}^{z} m_w \qquad (2)$$

wherein z has the same meaning as z described in the above mathematical expression (1), and represents the number of types of polytitanoxane having an R—O—Ti linkage having a different degree of polymerization contained in the polytitanoxane composition having the R—O—Ti linkage, and represents an integer of 1 or more.

For example, in the case of a composition comprising 1 mole of a tetraalkyloxytitanium represented by the following formula (1e), and 1 mole of a polytitanoxane represented by the following formula (2e), the mole average degree of polymerization is 1.5. The formulas (1e) and (2e) are as follows:

[Formula 55]

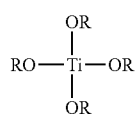
(1e)

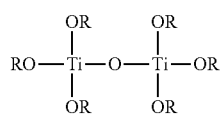
(2e)

When the above-described polytitanoxane is used as a catalyst for producing a diaryl carbonate, the above-described polytitanoxane is preferably a polytitanoxane having an R—O—Ti linkage comprising small molecules as little as possible, and having a high mole average degree of polymerization. When flowability is considered, the mole average degree of polymerization is preferably not very high. Therefore, the above-described mole average degree of polymerization is preferably in the range of 1.1 or more and 12 or less, most preferably in the range of 2 or more and 8 or less.

<Alkyloxytitanium Composition>

One example of the organic oxytitanium composition having the R—O—Ti linkage used as the titanium-containing catalyst composition in the present embodiment includes an alkyloxytitanium composition. Particularly, a polytitanoxane composition having an alkoxy group is preferred.

An alkyloxytitanium represents, among organic oxytitaniums constituting the above organic oxytitanium compositions having the R—O—Ti linkage, an organic oxytitanium in which the R group is an alkyl group, and the —O— forming the R—O—Ti linkage is oxygen bonded to the alkyl group.

Therefore, the alkyloxytitanium compositions are, among the above-described organic oxytitanium compositions having the R—O—Ti linkage, only those in which R is limited to an alkyl group, and only those excluding part of the illustrations of the R group (illustrations in which R is not an alkyl group).

Examples of such an R group include a methyl group, an ethyl group, a propyl group (isomers), a butyl group (isomers), a pentyl group (isomers), a hexyl group (isomers), a heptyl group (isomers), an octyl group (isomers), a nonyl group (isomers), and a decyl group (isomers). Examples of a preferred R group are a methyl group, an ethyl group, a propyl group (isomers), a butyl group (isomers), and a pentyl group (isomers).

<Cycloalkyloxytitanium Composition>

One example of the organic oxytitanium composition having an R—O—Ti linkage used as the titanium-containing catalyst composition in the present embodiment includes a cycloalkyloxytitanium composition. Particularly, a polytitanoxane composition having a cycloalkoxy group is preferred.

A cycloalkyloxytitanium represents, among organic oxytitaniums constituting the above organic oxytitanium compositions having the R—O—Ti linkage, an organic oxytitanium in which the R group is a cycloalkyl group, and the —O— forming the R—O—Ti linkage is oxygen bonded to the cycloalkyl group.

Therefore, the cycloalkyloxytitanium compositions are, among the above-described organic oxytitaniums having the R—O—Ti linkage, only those in which R is limited to a cycloalkyl group, and only those excluding part of the illustrations of the R group (illustrations in which R is not a cycloalkyl group).

Examples of such an R group include a cyclopentyl group, a cyclohexyl group, a cycloheptyl group, a cyclooctyl group, a cyclononyl group, and a cyclodecyl group. Examples of a preferred R group are a cyclopentyl group and a cyclohexyl group.

The organic oxytitanium compositions having the R—O—Ti linkage used in the present embodiment in which the R group is an alkyl group and in which the R group is a cycloalkyl group exhibit similar behavior in the above steps (1) and (2), and therefore, the above-described cycloalkyloxytitanium composition will be described below as having the same meaning as the alkyloxytitanium composition. (Exactly, the alkyl group is branched and/or linear, and the cycloalkyl group is cyclic, but there is no difference in reactivity and the like, and therefore, they have the same meaning herein. Similarly, a group in which a cycloalkyl group and an alkyl group are bonded to each other has the same meaning.)

<Aryloxytitanium Composition>

The aryloxytitanium composition used as the titanium-containing catalyst composition in the present embodiment represents, among the above organic oxytitanium compositions having the R—O—Ti linkage, an organic oxytitanium composition in which the R group is a group having an aromatic ring, and the —O— forming the R—O—Ti linkage is oxygen bonded to the group having an aromatic ring. Particularly, a polytitanoxane composition having an aryloxy group is preferred.

When the above group having the aromatic ring is represented as an Ar group (that is, a polytitanoxane having an aryloxy group is defined as a polytitanoxane having an Ar—O—Ti linkage), a polytitanoxane having an aryloxy group can be represented by the following formula according to the definition of the above polytitanoxane composition having the R—O—Ti linkage.

The structure of the polytitanoxane is diverse by the combination of the above formulas (1b) to (4b) (in the polytitanoxane having an aryloxy group, the R group in the above formulas (1b) to (4b) is an Ar group), that is, the following formulas (1f) to (4f), as described for the above polytitanoxane having the R—O—Ti linkage. It is difficult to identify the structure by the current analysis method, and the structure is presumed to be a mixture of various structures. The formulas (1f) to (4f) are as follows:

[Formula 56]

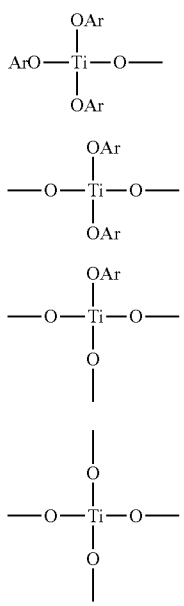

In the above formulas (1f) to (4f), Ar is a group having an aromatic ring, the Ar group forms an Ar—O—Ti linkage, and the oxygen atom of the ArO group in the linkage represents a group bonded to the aromatic ring in the Ar group.

The above aryloxy group constituting the aryloxytitanium is preferably represented by the following formula (ArO).

[Formula 57]

In the formula (ArO), the ring A represents an organic group having 6 to 20 carbon atoms, containing an aromatic group to which an oxygen atom bonded to Ti is bonded at any position keeping aromaticity, and may be a single ring or a plurality of rings, or a heterocyclic ring, and/or may be substituted by another substituent.

The ring A is often described as an Ar group herein.

The Ar group is not particularly limited as long as it is a group having an aromatic ring. Examples of the Ar group include groups composed of a carbon atom, a hydrogen atom, and/or an oxygen atom, such as an aromatic group and a group in which an aliphatic group and an aromatic group are bonded to each other. More specific examples include groups having an aromatic ring, which are an acyclic hydrocarbon group, a cyclic hydrocarbon group (a group such as, for example, a monocyclic hydrocarbon group, a condensed polycyclic hydrocarbon group, a bridged cyclic hydrocarbon group, a spiro hydrocarbon group, a ring assembly hydrocarbon group, a cyclic hydrocarbon group with a side chain, a heterocyclic group, a heterocyclic spiro group, or a bridged heterocyclic group), a group in which one or more groups selected from the above acyclic hydrocarbon group and the above cyclic hydrocarbon group are bonded, and a group in which the above groups are linked via covalent bonds to a particular nonmetal atom (carbon or oxygen).

The above covalent bond to the particular nonmetal atom (carbon or oxygen) is, for example, a state in which a group represented by the following formulas (1d) to (4d) and the above-described group are covalently bonded to each other.

[Formula 58]

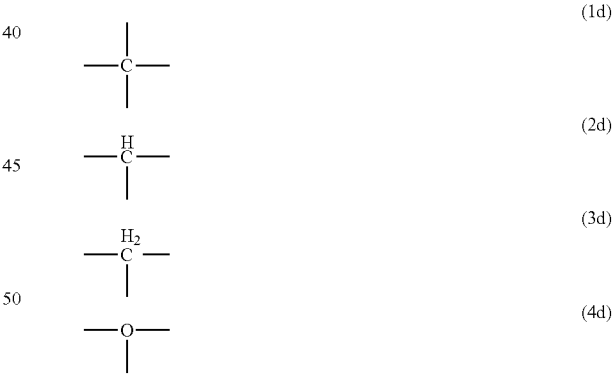

Among such Ar groups, the Ar group that can be preferably used in the present embodiment is selected from an aromatic group and a group in which an aliphatic group and an aromatic group are bonded to each other, considering that a side reaction is less likely to occur. Examples of the Ar group that can be preferably used in the present embodiment include a group selected from the group consisting of an acyclic hydrocarbon group and a cyclic hydrocarbon group (a monocyclic hydrocarbon group, a condensed polycyclic hydrocarbon group, a bridged cyclic hydrocarbon group, a spiro hydrocarbon group, a ring assembly hydrocarbon group, and a cyclic hydrocarbon group with a side chain), and a group in which at least one group selected from the group of these groups is bonded (groups substituted by each other), which are organic groups having 6 to 20 carbon atoms, preferably groups having 6 to 10 carbon atoms.

A more preferred Ar group is a group having an aromatic ring, which is a group selected from a group in which at least one or more selected from the group consisting of a cycloalkyl group and an aryl group are bonded to each other, and a group in which at least one or more selected from the group consisting of an alkyl group, a cycloalkyl group, and an aryl group are formed via a linkage selected from the above-described formulas (1d) to (4d).

A group having 6 or 7 carbon atoms is further preferred.

Examples of such Ar groups include a phenyl group, a cresyl group (isomers), a xylyl group (isomers), and a naphthyl group.

Examples of preferred Ar groups are a phenyl group and a cresyl group (isomers).

When the aryloxytitanium composition is used as the reaction catalyst in the production of the diaryl carbonate in the present embodiment, it is preferred that the aryl group constituting the diaryl carbonate, and the above-described aryl group constituting the aryloxytitanium composition are the same type of aryl group (that is, the aryloxy group constituting the aryloxytitanium composition is the same aryloxy group as the aryloxy group constituting the diaryl carbonate).

A monomer structure having an (Ar—O—)$_4$Ti structure, as well as the above polytitanoxane having the Ar—O—Ti linkage can be preferably used as the aryloxytitanium composition used in the present embodiment. As previously described, it is extremely difficult to isolate the polytitanoxane for determining the structure. The polytitanoxane having the Ar—O—Ti linkage used in the present embodiment is a polytitanoxane composition having an Ar—O—Ti linkage, containing at least one or more types of polytitanoxane having an Ar—O—Ti linkage.

Preferably, the above polytitanoxane composition having the Ar—O—Ti linkage is a composition such that a mole average degree of polymerization is 1.1 or more and 12 or less. The mole average degree of polymerization is determined by the following mathematical expression (1), using the number of Ti atoms contained in an individual polytitanoxane having an Ar—O—Ti linkage, which constitutes the polytitanoxane composition, and the following "molar ratio".

The polytitanoxane composition comprises one or more polytitanoxanes having a different degree of polymerization (the number of Ti atoms in the molecule).

The above "molar ratio" refers to the moles of a polytitanoxane having an individual degree of polymerization with respect to the total moles of polytitanoxanes in the polytitanoxane composition.

By the above "mole average degree of polymerization," it is meant that the product of the molar ratio of a polytitanoxane having an individual degree of polymerization and the degree of polymerization is determined, and the product is integrated for all degrees of polymerization to obtain an integrated value. In other words, the question of how many Ti atoms are contained in one polytitanoxane molecule is answered as average value.

[Expression 3]

$$Pn = \sum_i^z (p_w \cdot m_w) \quad (1)$$

In the above mathematical expression (1), Pn is a positive number representing the mole average degree of polymerization.

z represents the number of types of polytitanoxane having an Ar—O—Ti linkage having a different degree of polymerization contained in the polytitanoxane composition having the Ar—O—Ti linkage, and represents an integer of 1 or more.

$p_w$ is a positive natural number representing the number of Ti atoms contained in a polytitanoxane molecular structure w having an Ar—O—Ti linkage contained in the composition.

$m_w$ is the mole fraction of the above molecular structure w to the composition and satisfies the following mathematical expression (2).

The total of mole fractions is 1 (the left side).

[Expression 4]

$$1 = \sum_i^z m_w \quad (2)$$

In the above mathematical expression (2), z has the same meaning as z described in the above mathematical expression (1), and represents the number of types of polytitanoxane having an Ar—O—Ti linkage having a different degree of polymerization contained in the polytitanoxane composition having the Ar—O—Ti linkage, and represents an integer of 1 or more.

For example, in the case of a composition comprising 1 mole of a tetraaryloxytitanium represented by the following formula (1 g), and 1 mole of a polytitanoxane represented by the following formula (2 g), the mole average degree of polymerization is 1.5.

[Formula 59]

(1g)

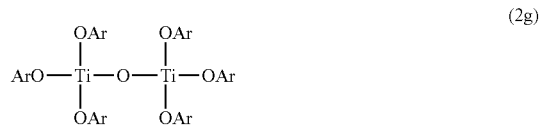

(2g)

When the aryloxytitanium composition is used as a reaction catalyst for the production method of a diaryl carbonate in the present embodiment, a polytitanoxane having an Ar—O—Ti linkage comprising small molecules as little as possible and having a high mole average degree of polymerization is preferred. When flowability is considered, the degree of polymerization is preferably not very high.

Therefore, the above-described mole average degree of polymerization is preferably in the range of 1.1 or more and 12 or less, more preferably in the range of 2 or more and 8 or less.

The titanium-containing catalyst composition used in the present embodiment is more preferably a titanium-containing composition comprising the above-described aryloxytitanium composition and diaryl carbonate. The above titanium-containing composition can be obtained by mixing the aryloxytitanium composition and the diaryl carbonate and by a method described later. The above aryloxytitanium composition can be obtained, for example, by reacting the above-described alkyloxytitanium composition with an aromatic monohydroxy compound described later.

The diaryl carbonate that is the raw material in obtaining the above titanium-containing catalyst composition is similar to the one described in the paragraphs of the above step (2).

The titanium constituting the above aryloxytitanium composition is preferably tetravalent.

The above aryloxytitanium composition preferably has 1 or more and 4 or less aryloxy groups per titanium atom.

(Method for Producing Titanium-Containing Catalyst Composition)

The titanium-containing catalyst composition used in the present embodiment can be produced, for example, by the following method. First, the above-described alkyloxytitanium composition is reacted with the aromatic monohydroxy compound described later so as to obtain an aryloxytitanium composition. At that time, ROH corresponding to the alkyloxy group is produced, and therefore, the boiling point of the ROH and the aromatic monohydroxy compound is compared to select an alkyloxytitanium composition and an aromatic monohydroxy compound used which are suitable for use.

<Aromatic Monohydroxy Compound>

The aromatic monohydroxy compound used will be described.

The aromatic monohydroxy compound is an aromatic monohydroxy compound represented by the formula (1h):

[Formula 60]

ArOH    (1h)

wherein the Ar group is a ring A given by the formula (2h):

[Formula 61]

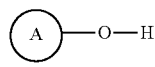    (2h)

In the above formula (2h), the ring A represents an organic group having 6 to 20 carbon atoms, comprising an aromatic group to which an oxygen atom forming an OH group is bonded at any position keeping aromaticity, and may be a single ring or a plurality of rings, or a heterocyclic ring, and/or may be substituted by another substituent.

The Ar group is not particularly limited as long as it is a group having an aromatic ring. Examples of the Ar group include groups composed of a carbon atom, a hydrogen atom, and/or an oxygen atom, such as an aromatic group and a group in which an aliphatic group and an aromatic group are bonded to each other. More specific examples include groups having an aromatic ring, which are a group comprising an acyclic hydrocarbon group or a cyclic hydrocarbon group (for example, a monocyclic hydrocarbon group, a condensed polycyclic hydrocarbon group, a bridged cyclic hydrocarbon group, a spiro hydrocarbon group, a ring assembly hydrocarbon group, a cyclic hydrocarbon group with a side chain, a heterocyclic group, a heterocyclic spiro group, and a bridged heterocyclic group), a group in which one or more groups selected from the above acyclic hydrocarbon group and the above cyclic hydrocarbon group are bonded, and a group in which the above groups are linked via covalent bonds to a particular nonmetal atom (carbon or oxygen).

The above covalent bond to the particular nonmetal atom (carbon or oxygen) is, for example, a state in which a group represented by the following formulas (1d) to (4d) and the above-described group are covalently bonded to each other.

[Formula 62]

$$-\underset{|}{\overset{|}{C}}-\quad (1d)$$

$$-\underset{|}{\overset{H}{C}}-\quad (2d)$$

$$-\overset{H_2}{C}-\quad (3d)$$

$$-\underset{|}{O}-\quad (4d)$$

Among such Ar groups, the Ar group that can be preferably used in the present embodiment is selected from an aromatic group and a group in which an aliphatic group and an aromatic group are bonded to each other, considering that a side reaction is less likely to occur. Examples of the Ar group that can be preferably used in the present embodiment include a group selected from the group consisting of an acyclic hydrocarbon group and a cyclic hydrocarbon group (a monocyclic hydrocarbon group, a condensed polycyclic hydrocarbon group, a bridged cyclic hydrocarbon group, a spiro hydrocarbon group, a ring assembly hydrocarbon group, and a cyclic hydrocarbon group with a side chain), and a group in which at least one group selected from the group is bonded (groups substituted by each other), which are organic groups having 6 to 20 carbon atoms, preferably groups having 6 to 10 carbon atoms. A further preferred Ar group is a group having an aromatic ring, which is a group selected from a group in which at least one or more selected from the group consisting of a cycloalkyl group and an aryl group are bonded to each other, and a group in which at least one or more selected from the group consisting of an alkyl group, a cycloalkyl group, and an aryl group are formed via a linkage selected from the above (1d) to (4d).

Examples of such Ar groups include a phenyl group, a cresyl group (isomers), a xylyl group (isomers), and a naphthyl group.

Examples of preferred Ar groups are a phenyl group and a cresyl group (isomers), more preferably a group having 6 or 7 carbon atoms.

When ROH has a lower boiling point than that of ArOH, ROH is easily removed by distillation, and therefore, an organic oxytitanium having an alkoxy group (R—O— group) and an aromatic hydroxy compound (ArOH) such that ROH has a lower boiling point than that of ArOH are selected.

In this case, the preferred R group is preferably a group having a small number of carbon atoms because of easy removal.

The R group preferably is a group having 1 to 6 carbon atoms, more preferably an alkyl group having 3 to 6 carbon atoms, considering the flowability of the organic oxytitanium having the R—O— group, and even more preferably a propyl group (isomers), a butyl group (isomers), a pentyl group (isomers), or a hexyl group (isomers).

For the aromatic hydroxy compound, phenols and cresol (isomers) can be preferably used, considering the industrial utility value.

The most preferred combination of the R group and the Ar group is a case where the R group is an R group selected from an n-propyl group, an isopropyl group, an n-butyl group, an isobutyl group, an n-pentyl group, and an isopentyl group, and the Ar group is a phenyl group.

Next, an amount of the alkyloxytitanium composition and the aromatic monohydroxy compound used will be described.

The amount of the aromatic monohydroxy compound used is preferably 1 to 50 molar equivalents, more preferably 5 to 30 molar equivalents, with respect to the total moles of alkoxy groups contained in the alkyloxytitanium composition and is determined by the size of the reactor, and the like.

If a large amount of polyhydroxy compounds (for example, catechol, trihydroxyphenol, and salicylic acid) are included in the aromatic monohydroxy compound, these polyhydroxy compounds react with the alkyloxytitanium, and the amount of the targeted aryloxytitanium produced decreases. Therefore, the content of these polyhydroxy compounds is preferably 0.01 or less, more preferably 0.001 or less, in terms of the molar ratio of the polyhydroxy compounds to titanium atoms.

As the method for obtaining the aryloxytitanium composition, for example, first, the above-described alkyloxytitanium composition is fed to a reactor in a nitrogen atmosphere, and then, the aromatic monohydroxy compound is fed. Next, the mixture in the above reactor is heated and reacted at ordinary pressure so as to obtain the aryloxytitanium composition. The heating temperature is preferably 0 to 300° C., more preferably 20 to 250° C., and further preferably 50 to 200° C. The heating time is preferably 0.01 to 500 hr, more preferably 0.1 to 300 hr, and further preferably 0.5 to 200 hr. The alcohol produced by the reaction is recovered as required.

The titanium-containing catalyst composition used in the present embodiment can be obtained, for example, by a method as described below.

First, a diaryl carbonate is fed to the aryloxytitanium composition obtained by the above method or the above-described aryloxytitanium composition, and the mixture in the reactor is heated. The heating temperature is preferably 100 to 300° C., more preferably 120 to 270° C., and further preferably 150 to 250° C. The heating time is preferably 0.1 to 500 hr, more preferably 0.2 to 300 hr, and further preferably 0.5 to 200 hr.

Next, the pressure of the above reactor is reduced, and the diaryl carbonate including a low boiling component is evaporated, and thus, the titanium-containing catalyst composition can be obtained. The titanium atoms constituting the above aryloxytitanium composition preferably have a content of 0.1 to 20% by mass, more preferably 1 to 15% by mass, further preferably 1 to 12% by mass, and particularly preferably 1 to 10% by mass, based on 100% by mass of the above titanium-containing catalyst composition. By appropriately adding the diaryl carbonate, the titanium concentration in the titanium-containing catalyst composition can be adjusted to be in the above range.

Specific examples of the alkyloxytitanium composition that is the raw material in obtaining the above aryloxytitanium composition include titanium tetramethoxide, titanium tetraisopropoxide, and titanium tetrabutoxide. These titanium-containing compounds can also be preferably used in the form of the polytitanoxane as described above, by being partially hydrolyzed.

[Composition A]

The composition A used in the present embodiment is a composition comprising the above-described diaryl carbonate and aryloxytitanium composition, and a compound represented by formulas (X) and/or (Y) described later.

The above composition A is preferably formed using the diaryl carbonate and the aryloxytitanium composition. Specifically, for example, the above composition A can be obtained by heating the above-described titanium-containing catalyst composition.

When the above-described titanium-containing catalyst composition is heated, a product having a higher boiling point than that of the above diaryl carbonate (hereinafter also described as a "high boiling product") is produced, and the composition A comprising the high boiling product is obtained. Examples of the high boiling product include a compound represented by the formula (X) described later. The present inventors presume that the stability of the above-described titanium-containing catalyst composition is increased by the production of such a high boiling product.

The above steps (1) and/or (2) is preferably performed in the presence of the above composition A. By using the composition A formed in this manner, in the above steps (1) and/or (2), the diaryl carbonate can be produced stably and efficiently for a long period without clogging.

In the method for producing the diaryl carbonate according to the present embodiment, in the above steps (1) and/or (2), the production of the diaryl carbonate is preferably started by feeding the above composition A.

The above composition A has a ratio of the total moles of the compounds represented by the formulas (X) and (Y) described later to the moles of titanium atoms (the total of the compounds represented by the formulas (X) and (Y)/titanium atoms) from 0.005 to 4, preferably from 0.005 to 3, and more preferably from 0.005 to 2.

The ratio of the total moles of the compounds represented by the formulas (X) and (Y) to the moles of titanium atoms (the total of the compounds represented by the formulas (X) and (Y)/titanium atoms) can be controlled by appropriately setting the type and concentration of the titanium-containing catalyst composition, conditions in heating the titanium-containing catalyst composition, and the like. Specifically, the ratio can be controlled by producing the high boiling product in the range of heating temperature and heating time described later, using the above-described titanium-containing catalyst composition.

By controlling the ratio of the total moles of the compounds represented by the formulas (X) and (Y) to the moles of titanium atoms in this manner, the clogging of the reaction apparatus with the catalyst is suppressed, and the diaryl carbonate can be stably produced with high efficiency.

The titanium constituting the above aryloxytitanium composition preferably has a content of 0.1 to 20% by mass, more preferably 1 to 15% by mass, further preferably 1 to 12% by mass, and particularly preferably 1 to 10% by mass, based on 100% by mass of the above composition A. By appropriately adding the diaryl carbonate, the content of the titanium in the above composition can be adjusted to be in the above range.

The titanium constituting the above aryloxytitanium composition is preferably tetravalent titanium.

The above aryloxytitanium composition preferably has 1 or more and 4 or less aryloxy groups per titanium atom.

(Compounds Represented by Formulas (X) and (Y))

The composition A used in the present embodiment contains the compound represented by the following formulas (X) and/or (Y).

Any of the compounds represented by the following formulas (X) and (Y) is a type of product having a higher boiling point than that of the diaryl carbonate (hereinafter also described as "high boiling product") that is produced by heating the above-described titanium-containing catalyst composition. The formulas (X) and (Y) are as follows:

[Formula 63]

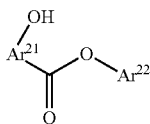

(X)

wherein Ar$^{21}$ represents an unsubstituted or substituted arylene group having 6 to 20 carbon atoms, Ar$^{22}$ represents an unsubstituted or substituted aryl group having 6 to 20 carbon atoms, and two substituents on Ar$^{21}$ are located at an ortho position to each other; and

[Formula 64]

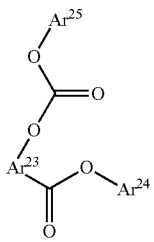

(Y)

wherein Ar$^{23}$ represents an unsubstituted or substituted arylene group having 6 to 20 carbon atoms, Ar$^{24}$ and Ar$^{25}$ each independently represent an unsubstituted or substituted aryl group having 6 to 20 carbon atoms, and two substituents on Ar$^{23}$ are located at an ortho position to each other.

Examples of the above Ar$^{21}$ and Ar$^{23}$ include a phenylene group and various alkylphenylene groups, such as phenylene, methylphenylene (isomers), dimethylphenylene (isomers), trimethylphenylene (isomers), tetramethylphenylene, ethylphenylene (isomers), diethylphenylene (isomers), methylethylphenylene (isomers), pentylphenylene (isomers), hexylphenylene (isomers), and cyclohexylphenylene (isomers); various alkoxyphenylene groups, such as methoxyphenylene (isomers), ethoxyphenylene (isomers), and butoxyphenylene (isomers); various halogenated phenylene groups, such as fluorophenylene (isomers), chlorophenylene (isomers), bromophenylene (isomers), chloro(methyl)phenylene (isomers), and dichlorophenylene (isomers); various substituted phenylene groups given by the following formula (Za); and a naphthylene group and various substituted naphthylene groups, such as naphthylene (isomers), methylnaphthylene (isomers), dimethylnaphthylene (isomers), chloronaphthylene (isomers), methoxynaphthylene (isomers), and cyanonaphthylene (isomers).

Ar$^{22}$, Ar$^{24}$, and Ar$^{25}$ correspond to the Ar$^{13}$ of the above-described diaryl carbonate. The formula (Za) is as follows:

[Formula 65]

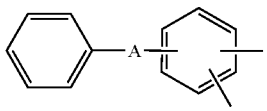

(Za)

wherein A represents any divalent group selected from the group consisting of a single bond, —O—, —S—, —CO—, —SO$_2$—, an alkylene group or a substituted alkylene group given by the following formula (Za-1), and a cycloalkylene group given by the following formula (Za-2), and the aromatic ring may be substituted by a substituent, such as a lower alkyl group, a lower alkoxy group, an ester group, a hydroxy group, a nitro group, a halogen, or a cyano group. The formulas (Za-1) and (Za-2) are as follows:

[Formula 66]

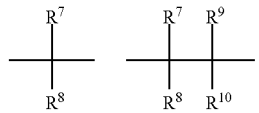

(Za-1)

wherein R$^7$, R$^8$, R$^9$, and R$^{10}$ are each independently a hydrogen atom, a lower alkyl group, a cycloalkyl group, an aryl group, or an aralkyl group, and may be substituted by a halogen atom or an alkoxy group; and

[Formula 67]

(Za-2)

wherein k is an integer of 3 to 11, and the hydrogen atom may be substituted by a lower alkyl group, an aryl group, or a halogen atom.

In the method for producing the diaryl carbonate according to the present embodiment, the compound given by the above formula (X) is produced as by-product by the occurrence of a Fries rearrangement reaction in the presence of the titanium-containing catalyst composition. The compounds given by the above formulas (X) and (Y) may be previously prepared and contained.

The case where the compound given by the above formula (X) is produced as by-product by the Fries rearrangement reaction in the presence of the titanium-containing catalyst composition will be described below.

The above titanium-containing catalyst composition has the function of significantly improving the reaction rates of the transesterification and disproportionation reactions, and a higher productivity of the diaryl carbonate can be thus achieved.

However, a side reaction due to Fries rearrangement given by the following formula (c) occurs in the presence of the titanium-containing catalyst composition. The formula (c) is as follows:

[Formula 68]

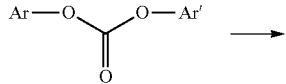

(c)

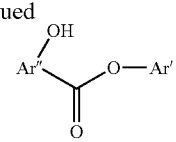

(The OH group is located at an ortho position)

wherein Ar and Ar' represent an aryl group, and Ar'' represents an arylene group.

The salicylate ester produced by the above formula (c) is generally the compound represented by the above formula (X).

The production of the salicylate ester by the side reaction described above increases as the temperature of the environment increases. Further, the salicylate ester has a high boiling point, and therefore is not separated by distillation from the titanium-containing catalyst composition similarly having a high boiling point. As a result, the salicylate ester easily coexists with the titanium-containing catalyst composition.

Such a salicylate ester reacts with a carbonate so as to produce a salicylate ester carbonate corresponding to the formula (Y), as given by the formula (d):

[Formula 69]

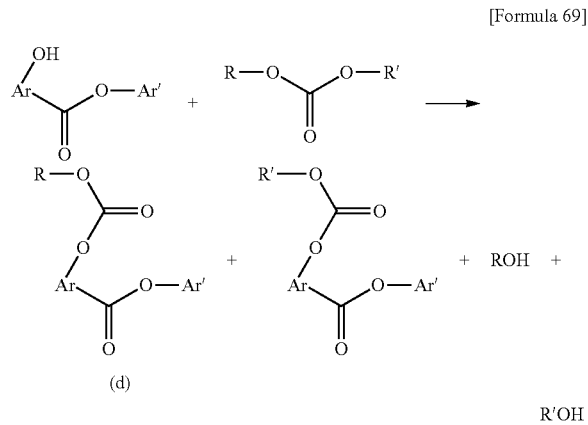

(d)

wherein Ar represents an arylene group having substituents at an ortho position to each other, R and R' represent an alkyl group or an aryl group, and Ar' represents an aryl group.

The compound represented by the above formula (X) can be obtained, for example, by the reaction of the corresponding diaryl carbonate and aryloxytitanium composition.

The conditions of the reaction in obtaining the compounds given by the above formulas (X) and (Y) will be described in detail below.

The reaction temperature varies depending on the type and concentration of the titanium-containing catalyst composition, but is preferably 100° C. or more and 300° C. or less, more preferably 150° C. or more and 250° C. or less, and further preferably 180° C. or more and 250° C. or less. The reaction pressure is preferably 0.1 or more and $2.0 \times 10^7$ Pa or less, more preferably 0.2 or more and $1.0 \times 10^7$ Pa or less, and further preferably 0.5 or more and $5.0 \times 10^6$ Pa or less.

Further, the reaction time varies depending on the reaction temperature and the type of the titanium-containing catalyst composition, but is preferably 0.1 hours or more and 500 hours or less, more preferably 0.2 hours or more and 300 hours or less, and further preferably 0.5 hours or more and 250 hours or less.

By producing the compounds given by the above formulas (X) and (Y) under the above reaction conditions, the composition A can be adjusted to have the ratio of the total moles of the compounds represented by the above formulas (X) and (Y) to the moles of titanium atoms (the total of the compounds represented by the formulas (X) and (Y)/titanium atoms) from 0.005 to 4. As a result, the stability of the above-described titanium-containing catalyst composition increases.

When the titanium-containing catalyst composition adjusted in this manner is used as the reaction catalyst in the method for producing the diaryl carbonate according to the present embodiment, the reaction catalyst is not either insolubilized or attached to the piping wall surface in feeding, leading to no problem, such as clogging.

In the method for producing the diaryl carbonate according to the present embodiment, the compounds represented by the above formulas (X) and (Y) produced as by-products may form stable complexes with the metal component contained in the catalyst. Then, the quantitative analysis of the compounds represented by the above formulas (X) and (Y) in the composition is inaccurate, and as a result, a problem arises that the ratio of the total moles of the compounds represented by the above formulas (X) and (Y) to the moles of titanium atoms (the total of the compounds represented by the formulas (X) and (Y)/titanium atoms) is not accurately obtained.

As described above, it is important to perform accurate quantitative analysis of the mixture comprising the compounds represented by the above formulas (X) and (Y) and the titanium-containing catalyst composition and accurately obtain the ratio of the total moles of the compounds represented by the above formulas (X) and (Y) to the moles of titanium atoms (the total of the compounds represented by the formulas (X) and (Y)/titanium atoms).

Specific examples of the method for performing accurate quantitative analysis of the mixture comprising the compounds represented by the above formulas (X) and (Y) and the titanium-containing catalyst composition include a method for adding an additive for dissociating the above complexes to the mixture comprising the compounds represented by the above formulas (X) and (Y) produced and the titanium-containing catalyst composition, performing treatment, such as filtration, as required, and performing quantitative analysis by gas chromatography or high performance liquid chromatography which uses a general analysis apparatus, in the method for producing the diaryl carbonate.

The above additive is selected according to the type of the aryloxytitanium composition constituting the catalyst. Examples of the above additive include water, polyhydroxy compounds, nitrogen-containing heterocyclic compounds, sulfur-containing heterocyclic compounds, fluorine-substituted alcohols, and fluorine-substituted organic acids, and preferably, water, catechol, phenanthroline, hexafluoroisopropanol, and trifluoroacetic acid. An amount of the additive with respect to the compounds represented by the above formulas (X) and (Y) varies depending on the metal constituting the catalyst, but is usually 1 or more equivalents, preferably 3 equivalents or more.

[Reaction Apparatus and the Like]

A reaction apparatus for carrying out the method for producing the diaryl carbonate in the present embodiment is not particularly limited, and reaction apparatuses of known various types, for example, an agitation tank, an agitation tank with multistage impellers, a multistage distillation column, and a combination thereof are used.

In the method for producing the diaryl carbonate according to the present embodiment, the reactions in the above steps (1) and (2) are preferably performed using a reaction apparatus comprising at least one selected from the group consisting of an agitation tank, an agitation tank with multistage impellers, a packed column, a distillation column, a multistage distillation column, a continuous multistage distillation column, a reactor comprising an internal support, and a forced circulation reactor.

These reaction apparatuses may be either a batch type or a continuous type. In terms of efficiently shifting the equilibrium toward the products, a method using a multistage distillation column is preferred, and a continuous process using a multistage distillation column is particularly preferred. The multistage distillation column is a distillation column having multiple stages in which the theoretical plate number of distillation is 2 or more, and may be any one as long as continuous distillation is possible.

Such a multistage distillation column may be any one that is usually used as a multistage distillation column, for example, an Oldershaw type distillation column, a plate column type using trays, such as a bubble cap tray, a perforated plate tray, a valve tray, a chimney tray, and a countercurrent tray, and a packed column type packed with various packings, such as a Raschig ring, a Lessing ring, a Pall ring, a Berl saddle, an Intalox saddle, a Dixon packing, a Mcmahon packing, a Heli pack, a Sulzer packing, and Mellapak. Further, a plate-packed column type having both a plate portion and a portion packed with a packing is also preferably used.

In the method for producing the diaryl carbonate according to the present embodiment, it is preferred that in the above step (1), the dialkyl carbonate and the aromatic monohydroxy compound are continuously fed to the above reaction apparatus, and in the above step (2), the reaction product obtained is continuously removed from the above reaction apparatus.

For example, when the continuous process is carried out using the multistage distillation column, it is preferred to continuously feed the dialkyl carbonate and the aromatic monohydroxy compound into a continuous multistage distillation column and carry out the reaction between both of the substances in a liquid phase or a gas-liquid phase in the presence of the above-described reaction catalyst in the distillation column. It is preferred to remove a high boiling product including a diaryl carbonate or a diaryl carbonate mixture produced, in a liquid state, from the lower portion of the distillation column, simultaneously with the reaction. On the other hand, by continuously removing a low boiling product including an alcohol as by-product or the dialkyl carbonate, in a gas state, by distillation from the upper portion of the distillation column, the diaryl carbonate is obtained.

In the step of producing the diaryl carbonate described above, when the reaction occurs in the multistage distillation column in which the catalyst is present, an amount of the reaction product produced usually depends on the holdup in the distillation column. In other words, when a distillation column having the same column height and the same column diameter is used, a distillation column having a large holdup is preferred in a sense that the residence time, that is, reaction time, of the reaction solution can be relatively long.

However, if the holdup is too large, the residence time is long, and therefore, a side reaction proceeds, and flooding is likely to occur.

Therefore, the holdup of the distillation column is preferably 0.005 to 0.75 as expressed by the ratio of the volume of the holdup to the empty column volume of the multistage distillation column, though it can also change depending on the distillation conditions and the type of the distillation column.

In the step of producing the diaryl carbonate described above, when the reflux ratio is increased, an effect of distilling the alcohol as by-product in the transesterification reaction, into a vapor phase increases, and therefore, a concentration of the alcohol in the removed vapor can be increased. However, if the reflux ratio is increased too much, the required thermal energy is excessive, which is unpreferred. The alcohol should be concentrated after it is removed from the distillation column, and therefore, refluxing is not always necessary.

Therefore, the reflux ratio is preferably 0 to 20, more preferably 0 to 10.

In other words, when the transesterification reaction typically given by the above-described reaction formula (a) is carried out, it is preferred to feed the dialkyl carbonate, the aromatic monohydroxy compound, and the catalyst to the multistage distillation column, as a mixture or through separate places, continuously remove the alkylaryl carbonate and/or the diaryl carbonate that is a product, in a liquid state, from a bottom of the distillation column, and continuously remove the low boiling component, such as the alcohol as by-product, in a gas state, by distillation from the upper portion of the distillation column.

At that time, the reaction catalyst may be fed through any place of the multistage distillation column, but is preferably fed to a position above a column bottom of the distillation column, and is further preferably fed to a position above a middle portion of the distillation column. In this case, the raw materials or the reaction solution in which the reaction catalyst is dissolved may be fed to the distillation column, or the reaction catalyst and the raw materials or the reaction solution may be separately fed to the distillation column.

When the disproportionation reaction typically given by the above formula (b) is carried out, it is preferred to feed the alkylaryl carbonate and the catalyst to the multistage distillation column, continuously remove the diaryl carbonate that is a product, in a liquid state, from the bottom of the distillation column, and continuously remove the low boiling component, such as the dialkyl carbonate as by-product, in a gas state, by distillation from the upper portion of the distillation column.

Instrumentation devices, such as a flowmeter and a thermometer, valves, piping joints, pumps, heat sources, and the like attached to the reaction apparatus can be used in a known range, and heat may be recovered, and the raw material, such as the dialkyl carbonate, may be recycled.

A reaction solvent is not essential to carry out the production method in the present embodiment. However, for the purpose of improving the flowability of the reaction raw materials and the products to make the transfer and reaction operations easy, an inert solvent may be applied.

Examples of such an inert solvent include acyclic or cyclic hydrocarbons having 5 to 16 carbon atoms, and ethers comprising acyclic or cyclic hydrocarbons having 4 to 16 carbon atoms.

Specific examples thereof include acyclic or cyclic hydrocarbons having 6 to 16 carbon atoms selected from pentane (isomers), hexane (isomers), heptane (isomers), octane (isomers), nonane (isomers), decane (isomers), tetradecane (isomers), hexadecane (isomers), cyclohexane, cycloheptane, cyclooctane, benzene, toluene, xylene (isomers), ethylbenzene, and the like; and ethers selected from diethyl ether, dipropyl ether (isomers), dibutyl ether (isomers), dihexyl ether (isomers), dioctyl ether (isomers), diphenyl ether, and the like.

EXAMPLES

The present invention will be specifically described by way of the following examples and comparative examples, although the present invention is not limited to the examples in any way.

First, an analysis method applied to the examples and the comparative examples will be described below.

[Analysis Method of Concentration of Metal in Metal-Containing Catalyst Composition]

A sample solution was collected, and the collected sample solution was subjected to a pretreatment using aqua regalis. ICP analysis was then carried out by the following apparatus, thereby obtaining the concentration of a metal in a metal-containing catalyst composition.

Analyzer: JY-138ULTRACE high frequency inductively-coupled plasma emission analyzer (ICP) system, manufactured by RIGAKU Corporation

[Analysis Method of Compounds Shown in the Above Items (i) to (iii) Other than Salicylate Ester and Formula (Y)]

[1] Production of Analysis Sample 1 g of a sample solution was weighed, and was dissolved in 5 mL of a trifluoroacetic acid/acetonitrile (20 g/l L) solution. The resulting solution was then filtered using a propylsulfonic acid filter. The filtrate was used as an analysis sample.

[2] Analysis Conditions

Analyzer: High-performance liquid chromatography LC10-AT system, manufactured by Shimadzu Corporation
Column: ODS-3V (GL Science Inertsil)
Column oven: 25° C.
Eluting solution: acetonitrile/water
Eluting solution gradient: Acetonitrile 15% v/v (11 min)→20% (31 min)→100% (20 min)
Flow rate: 1 mL/min
Injection rate: 10 μL
Detection part: UV (254 nm)

[3] Quantitative Analysis Method

Analysis was carried out for a reference sample of each reference material under the above-mentioned analysis conditions, and a calibration curve was prepared. Quantitative analysis of an analysis sample was then carried out based on the calibration curve, and compounds shown in the above items (i) to (iii) other than salicylate ester and the formula (Y) were quantified.

[Analysis Method of Compound Represented by Formula (X) or Salicylate Ester]

[1] Production of Analysis Sample Solution 0.06 g of a sample solution was weighed, and about 1.4 g of phenyl methyl ether was added thereto. Furthermore, about 0.04 g of toluene or diphenyl ether as an internal reference and about 0.05 g of catechol as a treatment for a titanium-containing composition were added to the obtained solution, and were sufficiently mixed. The mixture was then filtered with a membrane filter of 0.45 μm, and the filtrate was used as a gas chromatography analysis sample solution.

[2] Gas Chromatography Analysis Conditions

Analyzer: GC-2010 system, manufactured by Shimadzu Corporation
Column: DB-1 (manufactured by J & W Scientific, USA)
Liquid phase: 100% dimethylpolysiloxane
Length: 30 m
Inner diameter: 0.25 mm
Film thickness: 1 μm
Column temperature: 50° C. (held for 5 min)→200° C. (raised at 10° C./min; held at 200° C. for 5 min)→300° C. (held for 15 min)
Injection temperature: 300° C.
Detector temperature: 300° C.
Detection method: FID

[3] Quantitative Analysis Method

Analysis was carried out for a reference sample of each reference material under the above-mentioned analysis conditions, and a calibration curve was prepared. Quantitative analysis of an analysis sample solution was then carried out based on the calibration curve, and a compound represented by the formula (X) or salicylate ester was quantified.

[Analysis Method of Components Other than Compound Represented by Formula (1) and Components Other than Compounds Represented by Formulas (X) and (Y)]

[1] Production of Analysis Sample Solution 0.15 g of a sample solution was weighed, and about 2 g of dry acetone was added thereto. Furthermore, about 0.04 g of toluene or diphenyl ether as an internal reference was added thereto. The resulting solution was used as a gas chromatography analysis sample solution.

[2] Gas Chromatography Analysis Conditions

Analyzer: GC-2010 system, manufactured by Shimadzu Corporation
Column: DB-1 (manufactured by J & W Scientific, USA)
Liquid phase: 100% dimethylpolysiloxane
Length: 30 m
Inner diameter: 0.25 mm
Film thickness: 1 μm
Column temperature: 50° C. (held for 5 min)→200° C. (raised at 10° C./min; held at 200° C. for 5 min)→300° C. (held for 5 min)
Injection temperature: 300° C.
Detector temperature: 300° C.
Detection method: FID

[3] Quantitative Analysis Method

Analysis was carried out for a reference sample of each reference material under the above-mentioned analysis conditions, and a calibration curve was prepared. Quantitative analysis of an analysis sample solution was then carried out based on the calibration curve, and components other than a compound represented by the formula (1) and components other than compounds represented by the formulae (X) and (Y) were quantified.

[Analysis Method of Average Degree of Polymerization]

A titanium concentration of a titanium-containing compound was quantified by ICP analysis in the same manner as in the above-mentioned analysis method of the concentration of the metal in the titanium-containing composition, and furthermore, an alkoxy group (for example, butoxy) was quantitatively analyzed by a gas chromatography method to obtain an average degree of polymerization.

Example 1

Preparation of Titanium-Containing Composition 7 kg of tetrabutoxytitanium (manufactured by E.I. DuPont de Nemours & Company Inc., product name: Tyzor TnBT) was charged to a batch type reactor equipped with an agitator, a heater, and a distillation column and having a volume of 60 L in a nitrogen atmosphere. 14 kg of phenol previously distilled/purified was then charged thereto.

Next, the mixture in the batch type reactor was heated to 180° C. under a normal pressure by the heater, to react the mixture. n-Butanol generated by the reaction was recovered from the column top of the distillation column. Furthermore, the batch type reactor was depressurized to about 53 kPa, and n-butanol was recovered.

The batch type reactor was then returned to a normal pressure, and about 18 kg of diphenyl carbonate was charged thereto. The mixture in the reactor was heated to about 190° C. Next, the batch type reactor was depressurized to about 1.3 kPa, and the diphenyl carbonate containing a low boiling component was evaporated, thereby obtaining a titanium-containing composition. Diphenyl carbonate was added so that the titanium concentration of the obtained titanium-containing composition was 5% by mass. After the titanium-containing composition was heated at 200° C. for about 48 hours, the heated titanium-containing composition were used as a reaction catalyst for the following production of a diaryl carbonate.

(Producing Apparatus of Diaryl Carbonate)

A schematic configuration view of a producing apparatus used in example 1 is shown in FIG. 1.

The producing apparatus is equipped with distillation columns 110 and 120 which have a continuous multistage structure, a distillation column 130, and a distillation purification column 140.

These are connected via predetermined lines.

Specifically, lines 1 and 12 are feed lines for feeding raw compounds and a titanium-containing composition, or the like. Lines 3 and 9 are recovery lines for recovering a product compound and other materials. Lines 2, 4, 5, 6, 7, 8, and 10 are transfer lines. A line 11 is a removal line.

Reference numerals 111, 121, 131, and 141 designate reboilers, and reference numerals 112, 122, 132, and 142 designate condensers. Reference numeral 113 designate a preheater for setting a feed material to a predetermined temperature.

(Production of Diaryl Carbonate)
(1) Start-Up Operation

The distillation column 110 had a continuous multistage structure, and was equipped with a concentration part and a recovery part. The concentration part was filled with sieve trays of 25 stages, and had an inner diameter of 150 mm and a length of 4.8 m. The recovery part was filled with Melapak CY (manufactured by Sulzer Chemtech Ltd., Switzerland), and had an inner diameter of 150 mm and a length of 2.3 m.

In the distillation column 110, bis(3-methylbutyl) carbonate, phenol, and the reaction catalyst prepared above were continuously fed at about 1830 g/hr from the feed line 1 through the preheater 113 from the sieve tray of the 25th stage to perform a transesterification reaction. The feed rate of each material mixed liquid was adjusted so that the mass ratio of bis(3-methylbutyl) carbonate to phenol in the mixed liquid was about 1.08, and a titanium atom concentration was about 500 ppm.

The concentration part was provided below the stage continuously feeding the mixed liquid, and the recovery part was provided above the stage.

An amount of heat required for the reaction and distillation was controlled by providing an external heater, or by circulating a liquid in a lower column part through the reboiler 111. The method controlled a temperature of the column bottom of the multistage distillation column 110 to about 230° C., and a pressure of the column top thereof to about 140 kPa.

A reaction solution was continuously removed at about 1700 g/hr through the transfer line 2 from the column bottom of the continuous multistage distillation column 110.

A low boiling component containing 3-methyl-1-butanol as by-product was removed from the column top. The low boiling component was then condensed by the condenser 112, and was recovered by a reflux ratio of 2 from the recovery line 3.

The reaction solution removed from the transfer line 2 as described above was fed to the continuous multistage distillation column 120.

The continuous multistage distillation column 120 is equipped with the reboiler 121, the concentration part of the distillation column (the inner diameter: 150 mm, the length: about 6 m) filled with chimney trays of 5 stages, and the recovery part filled with Melapak CY and having an inner diameter of 150 mm and a length of 3.8 m. The feeding position of the reaction solution was set at the upper portion of the concentration part, and the feed rate of the reaction solution was set at about 1700 g/hr.

A temperature of the column bottom of the distillation column 120 was controlled to 200° C., and the pressure of the column top thereof was controlled to about 3 kPa. A disproportionation reaction was performed under these conditions.

A low boiling component containing phenol and bis(3-methylbutyl)carbonate was circulated to the distillation column 110 through the condenser 122, the transfer line 5, and the feed line 1 from the column top of the distillation column 120.

From the column bottom of the distillation column 120, the reaction solution containing diphenyl carbonate was fed to the distillation column 130 through the transfer line 4 to perform distillation separation.

The distillation column 130 was a distillation column filled with Melapak CY and having an inner diameter of 150 mm and a length of 4 m, and was provided with the reboiler 131 and the condenser 132.

A temperature of the column bottom of the distillation column 130 was controlled to about 180° C., and a pressure of the column top thereof was controlled to about 0.5 kPa.

The low boiling component containing diphenyl carbonate was removed from the column top, and was fed to the distillation purification column 140 through the condenser 132 and the transfer line 7.

On the other hand, a high boiling component containing a reaction catalyst was circulated to the distillation column 110 through the transfer line 6 and the feed line 1.

The distillation purification column 140 was a distillation column filled with Melapak CY and having an inner diameter of 150 mm and a length of 5 m, and was equipped with the reboiler 141 and the condenser 142.

The reaction solution containing diphenyl carbonate, fed to the distillation purification column 140 through the transfer line 7 from the distillation column 130 was purified in the distillation purification column 140. About 100% by mass of diphenyl carbonate (diaryl carbonate) was obtained from the recovery line 9 by the purification. The position of the recovery line 9 was set at the lower portion of the distillation column located above the column bottom.

The low boiling component containing 3-methylbutyl phenyl carbonate was removed from the column top of the distillation purification column 140, and was circulated to the distillation column 120 through the recovery line 10 and the transfer line 2.

(2) Control Operation

A rate of a titanium-containing high boiling component removed from the removal line 11 was adjusted to about 11 g/hr (the titanium atom concentration: about 1% by mass), and a rate of the reaction catalyst fed from the feed line 12 was adjusted to about 2.3 g/hr (the titanium atom concentration: about 5% by mass). The feed of the reaction catalyst from the feed line 1 was stopped.

Simultaneously, an amount of a liquid circulated to each distillation column was gradually increased so that a rate of the diphenyl carbonate recovered from the recovery line 9 was about 1000 g/hr.

After the continuous operation described above was performed for about 12 hours, the operation entered into a steady state.

At that time, in the transfer line 2, the composition of the liquid contained about 15% by mass of phenol, about 67% by mass of bis(3-methylbutyl)carbonate, about 17% by mass of 3-methy butyl phenyl carbonate, about 0.3% by mass of diphenyl carbonate, and about 0.2% by mass of 3-methyl-1-butanol. The flow rate thereof was about 11402 g/hr.

A residence times of the reaction solution in the steady state in the distillation columns 110 and 120 were respectively about 1 hr and about 2.5 hr.

The composition of the liquid in the recovery line 3 contained about 100% by mass of 3-methyl-1-butanol. The flow rate thereof was about 823 g/hr.

In the transfer line 4, the composition of the liquid contained about 0.2% by mass of bis(3-methylbutyl) carbonate, about 18% by mass of 3-methylbutyl phenyl carbonate, and about 80% by mass of diphenyl carbonate. The flow rate thereof was about 1238 g/hr.

In the transfer line 5, the composition of the liquid contained about 0.2% by mass of 3-methyl-1-butanol, about 17% by mass of phenol, and about 82% by mass of bis(3-methylbutyl)carbonate. The flow rate thereof was about 10300 g/hr.

In the transfer line 7, the composition of the liquid contained about 88% by mass of diphenyl carbonate, about 12% by mass of 3-methy butyl phenyl carbonate, and about 0.2% by mass of bis(3-methylbutyl)carbonate. The flow rate thereof was about 1140 g/hr.

When the titanium-containing high boiling component obtained from the removal line 11 was analyzed, the ratio of total moles of phenyl salicylate and 3-methylbutyl salicylate ester to moles of titanium atoms was about 0.7.

After the continuous operation described above was further continued for about 100 hr, the diphenyl carbonate (diaryl carbonate) recovered from the recovery line 9 could be stably produced at about 1000 g/hr.

The rate of the titanium-containing high boiling component removed from the removal line 11 was then adjusted to about 9 g/hr (the titanium atom concentration: about 1% by mass), and the rate of the reaction catalyst fed from the feed line 12 was adjusted to about 1.8 g/hr (the titanium atom concentration: about 5% by mass). Similarly, the continuous operation was performed for about 200 hr.

When the titanium-containing high boiling component obtained from the removal line 11 was analyzed, the ratio of total moles of salicylate esters of phenyl salicylate plus 3-methylbutyl salicylate ester to moles of titanium atoms was about 1.1. The ratio of moles of phenyl salicylate carbonate to moles of titanium atoms was about 0.2. Furthermore, the ratio of moles of catechol to moles of titanium atoms was about 0.01.

In the distillation separation in the distillation column 130, the high boiling component removed from the column bottom contained about 8% by mass of a component having a higher boiling point than that of the diphenyl carbonate.

Similarly, the diphenyl carbonate (diaryl carbonate) recovered from the recovery line 9 could be stably produced at about 1200 g/hr.

Examples 2 to 6

Start-up operation was performed in the same manner as in the example 1 except that dialkyl carbonates of types shown in the following Table 1 were used in place of bis(3-methylbutyl)carbonate, so as to produce diphenyl carbonate (diaryl carbonate). A flow rate and a pressure were controlled depending on the type of each dialkyl carbonate in control operation.

In distillation separation in a distillation column 130, a high boiling component removed from a column bottom contained about 7% by mass, about 10% by mass, about 8% by mass, about 9% by mass, and about 8% by mass of a component having a higher boiling point than that of the diphenyl carbonate, in order of examples 2 to 6.

The results of analyzing a titanium-containing high boiling component obtained from a removal line 11 are shown in Table 1. All the examples satisfied the conditions of the above-mentioned items (iv) to (vi), and could stably produce the diaryl carbonates.

TABLE 1

| | | molar ratio of each compound to titanium atoms | | | | |
|---|---|---|---|---|---|---|
| | dialkyl carbonate | phenyl salicylate | salicylate ester carbonate | phenyl salicylate carbonate | catechol | average recovery of diphenyl carbonate [kg/hr] |
| Example 1 | bis (3-methylbuthyloxy) carbonate | 0.3 | 0.8 | 0.2 | 0.2 | 0.01 | 1.2 |
| Example 2 | bis (cyclopentyloxy) carbonate | 0.5 | 0.7 | 0.1 | 0.2 | 0.04 | 1.2 |
| Example 3 | bis (2-methylpropyloxy) carbonate | 0.6 | 1.0 | 0.1 | 0.4 | 0.05 | 1.2 |
| Example 4 | bis (2-ethylbutyloxy) carbonate | 1.0 | 1.2 | 0.2 | 0.6 | 0.03 | 1.0 |
| Example 5 | di (n-butyl) carbonate | 0.8 | 1.5 | 0.1 | 0.5 | 0.04 | 1.2 |
| Example 6 | bis (n-pentyl) carbonate | 0.9 | 1.3 | 0.2 | 0.6 | 0.05 | 1.0 |

Example 7

Preparation of Titanium-Containing Composition 7 kg of polytitanoxane butoxide (manufactured by E.I. DuPont de Nemours & Company Inc., product name: Tyzor BTP) was charged to a batch type reactor equipped with an agitator, a heater, and a distillation column and having a volume of 60 L under a nitrogen atmosphere, and 14 kg of previously distilled/purified phenol was then charged thereto.

Next, the mixture in the batch type reactor was heated to 180° C. under a normal pressure by the heater to react the mixture. n-Butanol generated by the reaction was recovered from the column top of the distillation column. Furthermore, the batch type reactor was depressurized to about 53 kPa, and n-butanol was recovered.

The batch type reactor was then returned to a normal pressure. About 18 kg of diphenyl carbonate was charged thereto. The mixture in the reactor was heated to about 190° C. Next, the batch type reactor was depressurized to about 1.3 kPa, and the diphenyl carbonate containing a low boiling component was evaporated to obtain a titanium-containing composition. Diphenyl carbonate was added so that the titanium concentration of the obtained titanium-containing composition was 5% by mass.

(Producing Apparatus of Diaryl Carbonate)

Figure 2:
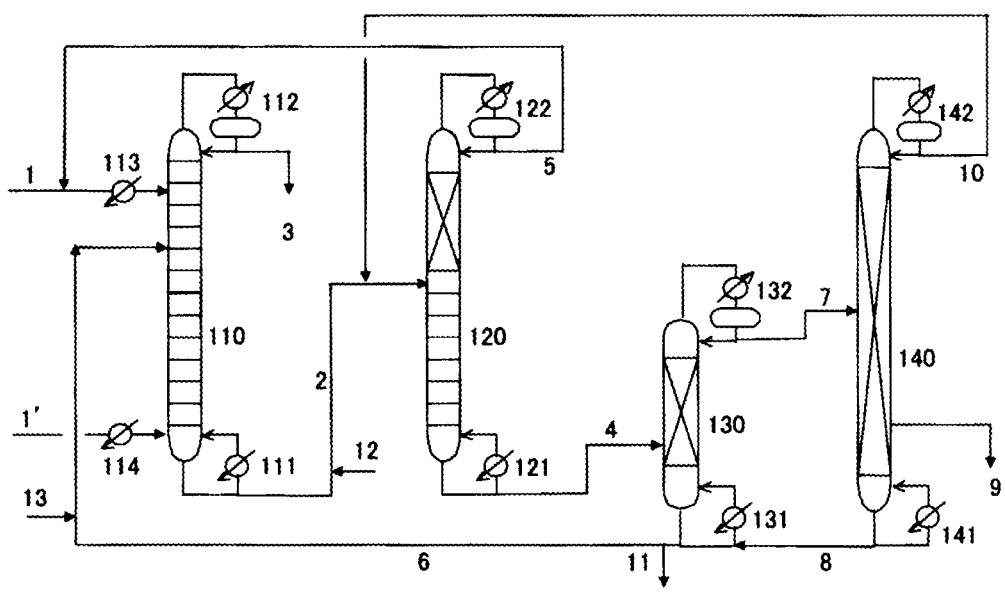
FIG. 2 shows a schematic configuration diagram of one example of the production apparatus for carrying out the method for producing the diaryl carbonate in the present embodiment.

A schematic configuration view of a producing apparatus used in example 7 is shown in FIG. 2.

The producing apparatus is equipped with distillation columns 110 and 120 which have a continuous multistage structure, a distillation column 130, and a distillation purification column 140.

These are connected via predetermined lines.

Specifically, lines 1, 1', 12, and 13 are feed lines feeding raw compounds and a titanium-containing composition, or the like. Lines 3 and 9 are recovery lines recovering a product compound and other materials. Lines 2, 4, 5, 6, 7, 8, and 10 are transfer lines. A line 11 is a removal line.

Reference numerals designate 111, 121, 131, and 141 designate reboilers, and reference numerals 112, 122, 132, and 142 designate condensers. Reference numeral 113 designate a preheater for setting a feed material to a predetermined temperature.

(Preparation of Reaction Catalyst)

In the distillation column 130, as described below, a product having a higher boiling point than that of diphenyl carbonate was produced to prepare a reaction catalyst.

The distillation column 130 was a distillation column filled with Melapak CY and having an inner diameter of 150 mm and a length of 4 m, and was provided with the reboiler 131 and the condenser 132.

About 10 kg of the prepared titanium-containing composition (the titanium concentration: about 5% by mass) was fed to the lower portion of the distillation column 130. A temperature of the titanium-containing composition was controlled to about 200° C. This state was held for about 72 hr. When part of the titanium-containing composition was then sampled and analyzed, phenyl salicylate having a higher boiling point than that of the diphenyl carbonate was detected. The molar ratio of phenyl salicylate and titanium atoms (phenyl salicylate/titanium atoms) was about 0.5. The mixture (hereinafter, also described as "composition A") of the high boiling product material generated in the distillation column 130 and the titanium-containing composition was used as a reaction catalyst for the next production of a diaryl carbonate.

(Production of Diaryl Carbonate)

The distillation column 110 had a continuous multistage structure. The distillation column 110 was filled with sieve trays of 50 stages and had an inner diameter of 150 mm and a length of 12 m. In the distillation column 110, a mixed liquid (a) containing about 30% by mass of dimethyl carbonate and about 70% by mass of phenol was continuously fed at about 41 kg/hr to the sieve tray of the 50th stage from the feed line 1 through the preheater 113. On the other hand, a mixed liquid (b) containing about 70% by mass of dimethyl carbonate and about 30% by mass of phenol was continuously fed at about 41 kg/hr to the lower portion of the distillation column 110 from the feed line 1'.

A concentration part was provided below the stage continuously feeding the mixed liquids (a) and (b), and a recovery part was provided above the stage.

An amount of heat required for the reaction and distillation was controlled by providing an external heater, or by circulating a liquid in a lower column part through the reboiler. The method controlled a temperature of the column bottom of the multistage distillation column 110 to about 230° C., and controlled a pressure of the column top thereof to about 0.55 MPa-G.

Next, the prepared reaction catalyst (composition A) was gradually fed to the 45th stage of the distillation column 110 from the lower portion of the distillation column 130 using the transfer line 6, and a titanium atom concentration in a reaction solution of the distillation column 110 was adjusted to about 300 ppm. The reaction solution was continuously removed at about 21 kg/hr through the transfer line 2 from the column bottom of the continuous multistage distillation column 110.

A low boiling component containing methanol as by-product was removed from the column top of the distillation column 110. The low boiling component was then condensed by the condenser 112, and was recovered from the recovery line 3.

The reaction solution removed from the transfer line 2 as described above was fed to the continuous multistage distillation column 120.

The continuous multistage distillation column 120 was equipped with the reboiler 121, the concentration part of a sieve tray type distillation column (the inner diameter: 150 mm, the length: about 4 m) of 16 stages, and the recovery part filled with Melapak CY and having an inner diameter of 150 mm and a length of about 4 m. The feeding position of the reaction solution was set at the upper portion of the concentration part, and the feed rate of the reaction solution was set at about 21 kg/hr.

A temperature of the column bottom of the distillation column 120 was controlled to 210° C., and a pressure of the column top thereof was controlled to about 13.3 kPa. A disproportionation reaction was performed under these conditions.

A low boiling component containing phenol and dimethyl carbonate was circulated to the distillation column 110 through the condenser 122, the transfer line 5, and the feed line 1 from the column top of the distillation column 120.

From the column bottom of the distillation column 120, the reaction solution containing diphenyl carbonate was fed to the distillation column 130 through the transfer line 4 to perform distillation separation.

The distillation column 130 was a distillation column filled with Melapak CY and having an inner diameter of 150 mm and a length of 4 m, and was provided with the reboiler 131 and the condenser 132.

A temperature of the column bottom of the distillation column 130 was controlled to about 190° C., and a pressure of the column top thereof was controlled to about 1.7 kPa.

The low boiling component containing diphenyl carbonate was removed from the column top, and was fed to the distillation purification column 140 through the condenser 132 and the transfer line 7.

On the other hand, a high boiling component containing the reaction catalyst (composition A) was circulated to the distillation column 110 through the transfer line 6 and the feed line 1.

The distillation purification column 140 was a distillation column filled with Melapak CY and having an inner diameter of 150 mm and a length of 5 m, and was equipped with the reboiler 141 and the condenser 142.

The reaction solution containing diphenyl carbonate fed to the distillation purification column 140 through the transfer line 7 from the distillation column 130 was purified in the distillation purification column 140. 99.8% by mass of diphenyl carbonate (diaryl carbonate) was obtained from the recovery line 9 by the purification. The position of the recovery line 9 was set at the lower portion of the distillation column located above the column bottom.

The low boiling component containing methyl phenyl carbonate was removed from the column top of the distillation purification column 140, and was circulated to the distillation column 120 through the recovery line 10 and the transfer line 2.

After the continuous operation described above was performed for about 12 hours, the operation entered into a steady state.

At that time, in the transfer line 2, the composition of the liquid contained about 55% by mass of phenol, about 26% by mass of dimethyl carbonate, about 17% by mass of methyl phenyl carbonate, about 2% by mass of diphenyl carbonate, and about 0.09% by mass of methanol. The flow rate thereof was about 40 kg/hr.

In the transfer line 4, the composition of the liquid contained about 0.1% by mass of dimethyl carbonate, about 17% by mass of methyl phenyl carbonate, about 3% by mass of phenol, and about 80% by mass of diphenyl carbonate. The flow rate thereof was about 6.2 kg/hr.

In the transfer line 7, the composition of the liquid contained about 78% by mass of diphenyl carbonate, about 19% by mass of methyl phenyl carbonate, and about 3% by mass of phenol. The flow rate thereof was about 5 kg/hr.

After the continuous operation described above was further continued for about 100 hr, the diphenyl carbonate (diaryl carbonate) recovered from the recovery line 9 could be stably produced at about 4 kg/hr.

When the titanium-containing high boiling component obtained from the removal line 11 was analyzed, the ratio of total moles of phenyl salicylate and methyl salicylate ester to moles of titanium atoms was about 1.2.

After the continuous operation described above was further continued for about 500 hr, the diphenyl carbonate (diaryl carbonate) recovered from the recovery line 9 could be stably produced at about 4 kg/hr.

The rate of the titanium-containing high boiling component removed from the removal line 11 was then adjusted to about 10 g/hr (the titanium atom concentration: about 1% by mass), and the rate of the reaction catalyst fed from the feed line 12 was adjusted to about 2.0 g/hr (the titanium atom concentration: about 5% by mass). Similarly, the continuous operation was performed for about 500 hr.

When the titanium-containing high boiling component obtained from the removal line 11 was analyzed, the ratio of total moles of salicylate esters of phenyl salicylate plus methyl salicylate ester to moles of titanium atoms was about 1.9. The ratio of moles of phenyl salicylate carbonate to moles of titanium atoms was about 0.5. Furthermore, the ratio of moles of catechol to moles of titanium atoms was about 0.02.

In the distillation separation in the distillation column 130, the high boiling component removed from the column bottom contained about 15% by mass of a component having a higher boiling point than that of the diphenyl carbonate.

Similarly, the diphenyl carbonate (diaryl carbonate) recovered from the recovery line 9 could be stably produced at about 4 kg/hr.

Production Example 1

Production of Polytitanoxane Composition Having Alkoxy Group

Hereinafter, Often Described as "Polytitanoxane Alkoxide"

20 kg of tetrabutoxytitanium (manufactured by E.I. DuPont de Nemours & Company Inc., Tyzor TnBT) was introduced to a reactor with an agitator. The reactor was equipped with a cooling coil, a heating jacket, and a distillation column. 8 kg of n-butanol was then introduced thereto, and an internal liquid temperature was adjusted to 0° C.

Hydrous n-butanol having a water concentration set at 2% by mass (% by weight) was adjusted to 0° C. in another reactor with an agitator. The reactor was equipped with a cooling coil, a heating jacket, and a distillation column.

The hydrous n-butanol was added into the reactor under agitation through a line.

The addition time was set at 1 hour, and the added amount of water was set at 0.5 molar equivalents (with respect to moles of Ti atoms in the reactor).

A trace moisture meter analyzed a reaction solution with time, and confirmed that the added water was consumed in a hydrolysis reaction and the analyzed value became constant.

The obtained reaction solution was heated under agitation, and n-butanol was evaporated using the distillation column after the reaction solution reached 150° C.

The composition of the evaporated liquid was analyzed by gas chromatography, and it was confirmed that the evaporated amount was mostly lost. The distillation was then completed.

When a transparent and colorless liquid left in the reactor was analyzed and a Ti content and an alkoxy group content were measured, it was found that polytitanoxane having a butoxy group having an average degree of polymerization of 2 (hereinafter often described as "polytitanoxane butoxide") was obtained.

Production Examples 2 to 4

Polytitanoxane alkoxide was produced in the same manner as in the above [production example 1] except that the added amount of water was changed as shown in Table 2. After the addition of water was completed, the reaction solution obtained as in the production example 1 was heated under agitation, and n-butanol was evaporated using the distillation column after the reaction solution reached 150° C. The composition of the evaporated liquid was analyzed by gas chromatography, and it was confirmed that the evaporated amount was mostly lost. The distillation was then completed. When a transparent and colorless liquid left in the reactor was analyzed and a Ti content and an alkoxy group content were measured, it was found that polytitanoxane butoxides having different average degrees of polymerization as shown in Table 2 were obtained.

TABLE 2

| | added amount of water with respect to moles of titanium [molar equivalent] | average degree of polymerization |
|---|---|---|
| Production Example 2 | 0.67 | 4 |
| Production Example 3 | 0.81 | 7 |
| Production Example 4 | 0.91 | 10 |

Examples 8 to 12

Diphenyl carbonate (diaryl carbonate) was produced in the same manner as in the example 7 except that tetrabutoxytitanium (manufactured by E.I. DuPont de Nemours & Company Inc., Tyzor TnBT) and the polytitanoxane alkoxides obtained from the production examples 1 to 4 were used in place of polytitanoxane butoxide (manufactured by E.I. DuPont de Nemours & Company Inc., product name: Tyzor BTP) in preparation of a titanium-containing composition.

In distillation separation in a distillation column 130, a high boiling component removed from a column bottom contained about 16% by mass, about 15% by mass, about 17% by mass, about 16% by mass, and about 18% by mass of a component having a higher boiling point than that of the diphenyl carbonate, in order of examples 8 to 12.

When a titanium-containing high boiling component obtained from a removal line 11 was analyzed, all the examples satisfied the above-mentioned items (iv) to (vi), and could stably produce the diaryl carbonates. The results are shown in Table 3.

rate of a reaction catalyst fed from a feed line 12 was adjusted to about 2.4 g/hr (the titanium atom concentration: about 5% by mass). Simultaneously, an amount of a liquid circulated to each distillation column was gradually increased so that a rate of diphenyl carbonate recovered from a recovery line 9 was about 1000 g/hr. After continuous operation was performed for about 12 hours, the operation entered into a steady state.

The rate of the titanium-containing high boiling component removed from the removal line 11 was then gradually adjusted to about 2 g/hr (the titanium atom concentration: about 1% by mass), and the rate of the reaction catalyst fed from a feed line 12 was gradually adjusted to about 0.4 g/hr (the titanium atom concentration: about 5% by mass). The continuous operation was performed in the same circulated amount of a liquid as that of the example 1. However, since the diphenyl carbonate recovered from the recovery line 9 was gradually decreased, a material liquid fed from a feed line 1 was adjusted corresponding thereto. After the continuous operation was performed for about 100 hr, the rate of the diphenyl carbonate recovered from the recovery line 9 was about 150 g/hr in the steady state.

When the titanium-containing high boiling component obtained from the removal line 11 was analyzed, the ratio of total moles of phenyl salicylate and 3-methylbutyl salicylate ester to moles of titanium atoms was about 4.0.

Furthermore, the rate of the titanium-containing high boiling component removed from the removal line 11 was adjusted to about 1.5 g/hr (the titanium atom concentration: about 1% by mass), and a rate of a titanium tetraphenoxide-containing phenol liquid fed from the feed line 12 was

TABLE 3

| | | molar ratio of each compound to titanium atoms | | | | | average recovery of |
|---|---|---|---|---|---|---|---|
| | titanium-containing composition | methyl salicylate | phenyl salicylate | salicylate ester carbonate | phenyl salicylate carbonate | catechol | diphenyl carbonate [kg/hr] |
| Example 8 | tetrabutoxytitanium | 0.5 | 1.7 | 0.1 | 0.4 | 0.05 | 4.0 |
| Example 9 | polytitanoxane butoxide (average degree of polymerization: 2) | 0.2 | 1.8 | 0.1 | 0.6 | 0.03 | 4.1 |
| Example 10 | polytitanoxane butoxide (average degree of polymerization: 4) | 0.3 | 1.8 | 0.2 | 0.5 | 0.04 | 4.0 |
| Example 11 | polytitanoxane butoxide (average degree of polymerization: 7) | 0.4 | 1.6 | 0.1 | 0.5 | 0.04 | 4.1 |
| Example 12 | polytitanoxane butoxide (average degree of polymerization: 10) | 0.2 | 1.7 | 0.1 | 0.6 | 0.05 | 4.1 |

Comparative Example 1

(1) Start-Up Operation

Operation until start-up operation was performed in the same manner as in the example 1.

(2) Control Operation

A rate of a titanium-containing high boiling component removed from a removal line 11 was adjusted to about 12 g/hr (the titanium atom concentration: about 1% by mass), and a adjusted to about 0.3 g/hr (the titanium atom concentration: about 5% by mass). Similarly, the continuous operation was performed.

After the continuous operation was performed for about 100 hr, the rate of the diphenyl carbonate recovered from the recovery line 9 was about 80 g/hr in the steady state.

When the titanium-containing high boiling component obtained from the removal line 11 was analyzed, the ratio of total moles of phenyl salicylate and 3-methylbutyl salicylate ester to moles of titanium atoms was about 4.2. Therefore, the condition of the above item (v) was not satisfied.

Comparative Example 2

(1) Start-Up Operation

Operation until start-up operation was performed in the same manner as in the example 1.

(2) Control Operation

A rate of a titanium-containing high boiling component removed from a removal line 11 was adjusted to about 8 g/hr (the titanium atom concentration: about 1.5% by mass), and a rate of a reaction catalyst fed from a feed line 12 was adjusted to about 2.4 g/hr (the titanium atom concentration: about 5% by mass). Simultaneously, an amount of a liquid circulated to each distillation column was gradually increased so that the rate of diphenyl carbonate recovered from a recovery line 9 was about 1000 g/hr. After continuous operation was performed for about 12 hours, the operation entered into a steady state.

A temperature of the column bottom of a distillation column 130 was then controlled to 250° C., and a pressure of the column top thereof was controlled to about 20 kPa. The rate of the titanium-containing high boiling component removed from the removal line 11 was gradually adjusted to about 4.7 g/hr (the titanium atom concentration: about 1.5% by mass), and the rate of the reaction catalyst fed from the feed line 12 was gradually adjusted to about 1.4 g/hr (the titanium atom concentration: about 5% by mass). The continuous operation was performed in the same circulated amount of a liquid as that of the example 1. However, since the diphenyl carbonate recovered from the recovery line 9 was gradually decreased, a material liquid fed from the feed line 1 was adjusted correspondingly thereto.

After the continuous operation was performed for about 100 hr, the rate of the diphenyl carbonate recovered from the recovery line 9 was about 350 g/hr in the steady state.

When the titanium-containing high boiling component obtained from the removal line 11 was analyzed, the ratio of total moles of phenyl salicylate and 3-methylbutyl salicylate ester to moles of titanium atoms was about 2.8.

Furthermore, the rate of the titanium-containing high boiling component removed from the removal line 11 was adjusted to about 2.0 g/hr (the titanium atom concentration: about 1.5% by mass), and the rate of the reaction catalyst fed from the feed line 12 was adjusted to about 0.6 g/hr (the titanium atom concentration: about 5% by mass). Similarly, the continuous operation was performed.

After the continuous operation was performed for about 100 hr, the rate of the diphenyl carbonate recovered from the recovery line 9 was about 100 g/hr in the steady state.

When the titanium-containing high boiling component obtained from the removal line 11 was analyzed, the ratio of total moles of phenyl salicylate and 3-methylbutyl salicylate ester to moles of titanium atoms was about 4.2. Therefore, the condition of the above item (v) was not satisfied.

Comparative Example 3

(1) Start-Up Operation

Operation until start-up operation was performed in the same manner as in the example 1 except that bis(3-methylbutyl)carbonate and phenol (the dissolved oxygen concentrations were about 60 ppm and about 80 ppm in order) stored under a compressed air atmosphere were used as materials.

(2) Control Operation

The rate of the titanium-containing high boiling component removed from a removal line 11 was adjusted to about 12 g/hr (the titanium atom concentration: about 1% by mass), and a rate of a titanium tetraphenoxide-containing phenol liquid fed from a feed line 12 was adjusted to about 2.4 g/hr (the titanium atom concentration: about 5% by mass). Simultaneously, an amount of a liquid circulated to each distillation column was gradually increased so that the rate of diphenyl carbonate recovered from a recovery line 9 was about 1000 g/hr. After continuous operation was performed for about 12 hours, the operation entered into a steady state.

The rate of the titanium-containing high boiling component removed from the removal line 11 was then gradually adjusted to about 5 g/hr (the titanium atom concentration: about 1% by mass), and the rate of the titanium tetraphenoxide-containing phenol liquid fed from the feed line 12 was gradually adjusted to about 1 g/hr (the titanium atom concentration: about 5% by mass, containing no salicylate ester). The continuous operation was performed in the same circulated amount of a liquid as that of the example 1. However, since the diphenyl carbonate recovered from the recovery line 9 was gradually decreased, a material liquid fed from a feed line 1 was adjusted corresponding thereto.

After the continuous operation was performed for about 100 hr, the rate of the diphenyl carbonate recovered from the recovery line 9 was about 250 g/hr in the steady state.

When the titanium-containing high-boiling substance obtained from the removal line 11 was analyzed, the titanium-containing high boiling component contained catechol, phenyl salicylate and 3-methylbutyl salicylate ester. The ratio of total moles thereof to moles of titanium atoms was about 2.2.

Furthermore, the rate of the titanium-containing high boiling component removed from the removal line 11 was adjusted to about 4 g/hr (the titanium atom concentration: about 1% by mass), and the rate of the titanium tetraphenoxide-containing phenol liquid fed from the feed line 12 was adjusted to about 0.8 g/hr (the titanium atom concentration: about 5% by mass, containing no salicylate ester). Similarly, the continuous operation was performed.

After the continuous operation was performed for about 100 hr, the rate of the diphenyl carbonate recovered from the recovery line 9 was about 90 g/hr in the steady state.

When the titanium-containing high-boiling substance obtained from the removal line 11 was analyzed, the ratio of total moles of phenyl salicylate and 3-methylbutyl salicylate ester to moles of titanium atoms was about 4.1. The ratio was four times larger than moles of the titanium-containing composition. The ratio of total moles of catechol to moles of titanium atoms was about 2.1. The ratio was two times larger than the titanium atoms of the titanium-containing composition. Therefore, the requirements of the above items (v) and (vi) were not satisfied in all the cases.

Comparative Examples 4 to 8

Preparation of Reaction Catalyst

Titanium-containing compositions were prepared in the same manner as in the example 7 except that tetrabutoxytitanium (manufactured by E.I. DuPont de Nemours & Company Inc., Tyzor TnBT) and the polytitanoxane alkoxides obtained from the production examples 1 to 4 were used in place of polytitanoxane butoxide (manufactured by E.I. DuPont de Nemours & Company Inc., product name: Tyzor BTP) in preparation of the titanium-containing compositions.
(Production of Diaryl Carbonate)

The titanium-containing composition prepared above was used as a reaction catalyst for a diaryl carbonate as it is without preparing a composition A from the titanium-containing composition. 95% by mass of a high boiling component in a distillation column 130 was recovered from a removal line 11. Diphenyl carbonate (diaryl carbonate) was produced in the same manner as in the example 7 except that the reaction catalyst was fed from a feed line 13. The results are shown in Table 4. When the reaction catalyst was fed for several hours (3 to 5 hr) in all the comparative examples 4 to 8, the feed line 13 was blocked, and the operation became impossible.

TABLE 4

| | titanium-containing compound | molar ratio of each compound to titanium atoms | | | | | continuous operation time [hr] |
|---|---|---|---|---|---|---|---|
| | | methyl salicylate | phenyl salicylate | salicylate ester carbonate | phenyl salicylate carbonate | catechol | |
| Comparative Example 4 | tetrabutoxytitanium | 0.001 | 0.002 | 0.00 | 0.00 | 0.001 | 5 |
| Comparative Example 5 | polytitanoxane butoxide (average degree of polymerization: 2) | 0.002 | 0.001 | 0.00 | 0.00 | 0.001 | 4 |
| Comparative Example 6 | polytitanoxane butoxide (average degree of polymerization: 4) | 0.001 | 0.001 | 0.00 | 0.00 | 0.002 | 4 |
| Comparative Example 7 | polytitanoxane butoxide (average degree of polymerization: 7) | 0.001 | 0.002 | 0.00 | 0.00 | 0.001 | 5 |
| Comparative Example 8 | polytitanoxane butoxide (average degree of polymerization: 10) | 0.001 | 0.001 | 0.00 | 0.00 | 0.001 | 3 |

Comparative Examples 9 to 13

Preparation of Reaction Catalyst

Titanium-containing compositions were prepared in the same manner as in the example 7 except that tetrabutoxytitanium (manufactured by E.I. DuPont de Nemours & Company Inc., Tyzor TnBT) and the polytitanoxane alkoxides obtained from the production examples 1 to 4 were used in place of polytitanoxane butoxide (manufactured by E.I. DuPont de Nemours & Company Inc., product name: Tyzor BTP) in preparation of the titanium-containing compositions.

(Production of Diaryl Carbonate)

Diphenyl carbonate (diaryl carbonate) was produced in the same manner as in the example 7 except that a temperature as a heating condition in preparing a composition A was changed to 230° C. from 200° C., and the heating time was changed to 200 hr from 72 hr. The results are shown in Table 5. Since an amount of production of the diphenyl carbonate (diaryl carbonate) was unstable, the continuous operation time was about 8 to 30 hours.

TABLE 5

| | titanium-containing compound | molar ratio of each compound to titanium atoms | | | | | average recovery of diphenyl carbonate [kg/hr] | continuous operation time [hr] |
|---|---|---|---|---|---|---|---|---|
| | | methyl salicylate | phenyl salicylate | salicylate ester carbonate | phenyl salicylate carbonate | catechol | | |
| Comparative Example 9 | tetrabutoxytitanium | 0.25 | 4.1 | 0.30 | 0.50 | 0.05 | 1.0 | 24 |
| Comparative Example 10 | polytitanoxane butoxide (average degree of polymerization: 2) | 0.30 | 4.2 | 0.25 | 0.60 | 0.04 | 0.8 | 20 |
| Comparative Example 11 | polytitanoxane butoxide (average degree of polymerization: 4) | 0.35 | 4.1 | 0.30 | 0.40 | 0.03 | 0.7 | 15 |
| Comparative Example 12 | polytitanoxane butoxide (average degree of polymerization: 7) | 0.20 | 4.1 | 0.35 | 0.50 | 0.02 | 0.9 | 30 |
| Comparative Example 13 | polytitanoxane butoxide (average degree of polymerization: 10) | 0.25 | 4.1 | 0.25 | 0.30 | 0.03 | 0.6 | 8 |

Comparative Examples 14 to 18

Preparation of Reaction Catalyst

Titanium-containing compositions were prepared in the same manner as in the example 7 except that tetrabutoxytitanium (manufactured by E.I. DuPont de Nemours & Company Inc., Tyzor TnBT) and the polytitanoxane alkoxides obtained from the production examples 1 to 4 were used in place of polytitanoxane butoxide (manufactured by E.I. DuPont de Nemours & Company Inc., product name: Tyzor BTP) in preparation of the titanium-containing compositions. Diphenyl carbonate was added so that the titanium content of the obtained titanium-containing composition was changed from 5% by mass to about 0.6% by mass.

(Production of Diaryl Carbonate)

Diphenyl carbonate (diaryl carbonate) was produced in the same manner as in the example 7 except that a temperature as a heating condition in preparing a composition A was changed to 250° C. from 200° C., and the heating time was changed to 300 hr from 72 hr. The results are shown in Table 6. Since the amount of production of the diphenyl carbonate (diaryl carbonate) was unstable, the continuous operation time was about 9 to 20 hours. In distillation separation in a distillation column 130, a high boiling component removed from a column bottom contained about 72% by mass, about 70% by mass, about 71% by mass, about 72% by mass, and about 74% by mass of a component having a higher boiling point than that of the diphenyl carbonate, in order of the comparative examples 14 to 18.

was evaporated to obtain a titanium-containing composition. Diphenyl carbonate was added so that the titanium concentration of the obtained titanium-containing composition was 5% by mass.

(Producing Apparatus of Diaryl Carbonate)

A schematic configuration view of a producing apparatus used in example 13 is shown in FIG. 2.

The producing apparatus is equipped with distillation columns 110 and 120 which have a continuous multistage structure, a distillation column 130, and a distillation purification column 140.

These are connected via predetermined lines.

Specifically, lines 1, 1', 12, and 13 are feed lines feeding raw compounds and a titanium-containing composition, or the like. Lines 3 and 9 are recovery lines recovering a product compound and other materials. Lines 2, 4, 5, 6, 7, 8, and 10 are transfer lines. A line 11 is a removal line.

Reference numerals designate 111, 121, 131, and 141 designate reboilers, and reference numerals 112, 122, 132, and 142 designate condensers. Reference numeral 113 designate a preheater for setting a feed material to a predetermined temperature.

TABLE 6

| | | molar ratio of each compound to titanium atoms | | | | average recovery of diphenyl carbonate [kg/hr] | continuous operation time [hr] |
|---|---|---|---|---|---|---|---|
| | titanium-containing compound | methyl salicylate | phenyl salicylate | salicylate ester carbonate | phenyl salicylate carbonate | catechol | |
| Comparative Example 14 | tetrabutoxytitanium | 0.35 | 6.1 | 2.3 | 18.0 | 0.06 | 0.9 | 19 |
| Comparative Example 15 | polytitanoxane butoxide (average degree of polymerization: 2) | 0.45 | 6.2 | 2.4 | 17.7 | 0.05 | 0.9 | 20 |
| Comparative Example 16 | polytitanoxane butoxide (average degree of polymerization: 4) | 0.55 | 5.9 | 2.2 | 18.0 | 0.05 | 0.8 | 16 |
| Comparative Example 17 | polytitanoxane butoxide (average degree of polymerization: 7) | 0.60 | 5.8 | 2.5 | 18.2 | 0.04 | 0.7 | 18 |
| Comparative Example 18 | polytitanoxane butoxide (average degree of polymerization: 10) | 0.50 | 6.0 | 2.3 | 18.4 | 0.07 | 0.6 | 9 |

Example 13

Preparation of Titanium-Containing Composition 7 kg of polytitanoxane butoxide (manufactured by E.I. DuPont de Nemours & Company Inc., product name: Tyzor BTP) was charged to a batch type reactor equipped with an agitator, a heater, and a distillation column and having a volume of 60 L under a nitrogen atmosphere, and 14 kg of previously distilled/purified phenol was then charged thereto.

Next, the mixture in the batch type reactor was heated to 180° C. under a normal pressure by the heater to react the mixture. n-Butanol generated by the reaction was recovered from the column top of the distillation column. Furthermore, the batch type reactor was depressurized to about 53 kPa, and n-butanol was recovered.

The batch type reactor was then returned to a normal pressure. About 18 kg of diphenyl carbonate was charged thereto. The mixture in the reactor was heated to about 190° C. Next, the batch type reactor was depressurized to about 1.3 kPa, and the diphenyl carbonate containing a low boiling component (Preparation of Composition A)

In the distillation column 130, as described below, a product having a higher boiling point than that of the diphenyl carbonate was produced to prepare a composition A.

The distillation column 130 was a distillation column filled with Melapak CY and having an inner diameter of 150 mm and a length of 4 m, and was provided with the reboiler 131 and the condenser 132.

About 10 kg of the prepared titanium-containing composition (the titanium concentration: about 5% by mass) was fed to the lower portion of the distillation column 130. A temperature of the titanium-containing composition was controlled to about 200° C. This state was held for about 72 hr. When part of the titanium-containing composition was then sampled and analyzed, phenyl salicylate and phenyl salicylate carbonate having a higher boiling point than that of the diphenyl carbonate were detected. The molar ratio of total of phenyl salicylate and phenyl salicylate carbonate, and titanium atoms (total of phenyl salicylate and phenyl salicylate carbonate/titanium atoms) was about 0.5. The mixture (hereinafter, also described as "composition A") of the high boiling product material generated in the distillation column 130 and the titanium-containing composition was used as a reaction catalyst for the next production of a diaryl carbonate.

(Production of Diaryl Carbonate)

The distillation column 110 had a continuous multistage structure. The distillation column 110 was filled with sieve trays of 50 stages and had an inner diameter of 150 mm and a length of 12 m. In the distillation column 110, a mixed liquid (a) containing about 30% by mass of dimethyl carbonate and about 70% by mass of phenol was continuously fed at about 41 kg/hr to the sieve tray of the 50th stage from the feed line 1 through the preheater 113. On the other hand, a mixed liquid (b) containing about 70% by mass of dimethyl carbonate and about 30% by mass of phenol was continuously fed at about 41 kg/hr to the lower portion of the distillation column 110 from the feed line 1'.

A concentration part was provided below the stage continuously feeding the mixed liquids (a) and (b), and a recovery part was provided above the stage.

An amount of heat required for the reaction and distillation was controlled by providing an external heater, or by circulating a liquid in a lower column part through the reboiler. The method controlled a temperature of the column bottom of the multistage distillation column 110 to about 230° C., and controlled a pressure of the column top thereof to about 0.55 MPa-G.

Next, the prepared composition A was gradually fed to the 45th stage of the distillation column 110 from the lower portion of the distillation column 130 using the transfer line 6, and the titanium atom concentration in the column bottom of the distillation column 110 was adjusted to about 300 ppm. A reaction solution was continuously removed at about 21 kg/hr through the transfer line 2 from the column bottom of the continuous multistage distillation column 110.

A low boiling component containing methanol as by-product was removed from the column top of the distillation column 110. The low boiling component was then condensed by the condenser 112, and was recovered from the recovery line 3.

The reaction solution removed from the transfer line 2 as described above was fed to the continuous multistage distillation column 120.

The continuous multistage distillation column 120 was equipped with the reboiler 121, the concentration part of a sieve tray type distillation column (the inner diameter: 150 mm, the length: about 4 m) of 16 stages, and the recovery part filled with Melapak CY and having an inner diameter of 150 mm and a length of about 4 m. The feeding position of the reaction solution was set at the upper portion of the concentration part, and the feed rate of the reaction solution was set at about 21 kg/hr.

A temperature of the column bottom of the distillation column 120 was controlled to 210° C., and a pressure of the column top thereof was controlled to about 13.3 kPa. A disproportionation reaction was performed under these conditions.

A low boiling component containing phenol and dimethyl carbonate was circulated to the distillation column 110 through the condenser 122, the transfer line 5, and the feed line 1 from the column top of the distillation column 120.

From the column bottom of the distillation column 120, the reaction solution containing diphenyl carbonate was fed to the distillation column 130 through the transfer line 4 to perform distillation separation.

The distillation column 130 was a distillation column filled with Melapak CY and having an inner diameter of 150 mm and a length of 4 m, and was provided with the reboiler 131 and the condenser 132.

The temperature of the column bottom of the distillation column 130 was controlled to about 190° C., and the pressure of the column top thereof was controlled to about 1.7 kPa.

The low boiling component containing diphenyl carbonate was removed from the column top, and was fed to the distillation purification column 140 through the condenser 132 and the transfer line 7.

On the other hand, the high boiling component containing the composition A was circulated to the distillation column 110 through the transfer line 6 and the feed line 1.

The distillation purification column 140 was a distillation column filled with Melapak CY and having an inner diameter of 150 mm and a length of 5 m, and was equipped with the reboiler 141 and the condenser 142.

The reaction solution containing diphenyl carbonate fed to the distillation purification column 140 through the transfer line 7 from the distillation column 130 was purified in the distillation purification column 140. 99.8% by mass of the diphenyl carbonate (diaryl carbonate) was obtained from the recovery line 9 by the purification. The position of the recovery line 9 was set at the lower portion of the distillation column located above the column bottom.

The low boiling component containing methyl phenyl carbonate was removed from the column top of the distillation purification column 140, and was circulated to the distillation column 120 through the recovery line 10 and the transfer line 2.

After the continuous operation described above was performed for about 12 hours, the operation entered into a steady state.

At that time, in the transfer line 2, the composition of the liquid contained about 55% by mass of phenol, about 26% by mass of dimethyl carbonate, about 17% by mass of methyl phenyl carbonate, about 2% by mass of diphenyl carbonate, and about 0.09% by mass of methanol. The flow rate thereof was about 40 kg/hr.

In the transfer line 4, the composition of the liquid contained about 0.1% by mass of dimethyl carbonate, about 17% by mass of methyl phenyl carbonate, about 3% by mass of phenol, and about 80% by mass of diphenyl carbonate. The flow rate thereof was about 6.2 kg/hr.

In the transfer line 7, the composition of the liquid contained about 78% by mass of diphenyl carbonate, about 19% by mass of methyl phenyl carbonate, and about 3% by mass of phenol. The flow rate thereof was about 5 kg/hr.

After the continuous operation described above was further continued for about 100 hr, the diphenyl carbonate recovered from the recovery line 9 could be stably produced at about 4 kg/hr.

When the titanium-containing high boiling component obtained from the removal line 11 was analyzed, the ratio of total moles of salicylate esters of phenyl salicylate plus methyl salicylate ester to moles of titanium atoms was about 1.3. The ratio of moles of phenyl salicylate carbonate to moles of titanium atoms was about 0.08. Furthermore, the ratio of moles of catechol to moles of titanium atoms was about 0.008.

In the distillation separation in the distillation column 130, the high boiling component removed from the column bottom contained about 11% by mass of a component having a higher boiling point than that of the diphenyl carbonate.

Example 14

Diphenyl carbonate (diaryl carbonate) was produced in the same manner as in the example 13 except that tetrabutoxytitanium (manufactured by E.I. DuPont de Nemours & Company Inc., Tyzor TnBT) was used in place of polytitanoxane butoxide (manufactured by E.I. DuPont de Nemours & Company Inc., product name: Tyzor BTP) in preparation of a titanium-containing composition, and the molar ratio of total of phenyl salicylate and phenyl salicylate carbonate, and titanium atoms (total of phenyl salicylate and phenyl salicylate carbonate/titanium atoms) in a composition A was changed to about 1.1 from about 0.5 in preparation of the composition A.

99.8% by mass of diphenyl carbonate (diaryl carbonate) was obtained from a recovery line 9.

A low boiling component containing methyl phenyl carbonate was removed from the column top of a distillation purification column 140, and was circulated to the distillation column 120 through a recovery line 10 and a transfer line 2.

After the continuous operation described above was performed for about 12 hours, the operation entered into a steady state.

At that time, in the transfer line 2, the composition of the liquid contained about 53% by mass of phenol, about 26% by mass of dimethyl carbonate, about 17% by mass of methyl phenyl carbonate, about 2% by mass of diphenyl carbonate, and about 0.09% by mass of methanol. The flow rate thereof was about 40 kg/hr.

In the transfer line 4, the composition of the liquid contained about 0.1% by mass of dimethyl carbonate, about 17% by mass of methyl phenyl carbonate, about 3% by mass of phenol, and about 80% by mass of diphenyl carbonate. The flow rate thereof was about 6.2 kg/hr.

In the transfer line 7, the composition of the liquid contained about 78% by mass of diphenyl carbonate, about 19% by mass of methyl phenyl carbonate, and about 3% by mass of phenol. The flow rate thereof was about 5 kg/hr.

After the continuous operation described above was further continued for about 100 hr, the diphenyl carbonate (diaryl carbonate) recovered from the recovery line 9 could be stably produced at about 4 kg/hr.

When a titanium-containing high boiling component obtained from a removal line 11 was analyzed, the ratio of total moles of salicylate esters of phenyl salicylate plus methyl salicylate ester to moles of titanium atoms was about 1.6. The ratio of moles of phenyl salicylate carbonate to moles of titanium atoms was about 0.4. Furthermore, the ratio of moles of catechol to moles of titanium atoms was about 0.01.

In distillation separation in a distillation column 130, a high boiling component removed from a column bottom contained about 12% by mass of a component having a higher boiling point than that of the diphenyl carbonate.

Examples 15 to 30

Diphenyl carbonate (diaryl carbonate) was produced in the same manner as in the example 13 except that polytitanoxane butoxides having different average degrees of polymerization, obtained from the production examples 1 to 4 as shown in the following Table 7 were used in preparation of a titanium-containing composition, and the molar ratio of total of phenyl salicylate and phenyl salicylate carbonate, and titanium atoms (total of phenyl salicylate and phenyl salicylate carbonate/titanium atoms) in a composition A was changed as shown in the following Table 7 in preparation of the composition A. The results are shown in Table 7. The results showed that continuous operation was possible for 150 to 200 hours without blocking the distillation column when the compositions A prepared in the examples 15 to 30 were fed, and the diphenyl carbonate (diaryl carbonate) could be stably produced.

In distillation separation in a distillation column 130, a high boiling component removed from a column bottom contained about 9% by mass, about 9% by mass, about 8% by mass, about 8% by mass, about 18% by mass, about 36% by mass, about 32% by mass, about 13% by mass, about 12% by mass, about 22% by mass, about 38% by mass, about 33% by mass, about 23% by mass, about 27% by mass, about 31% by mass, and about 39% by mass of a component having a higher boiling point than that of the diphenyl carbonate, in order of examples 15 to 30.

When a titanium-containing high boiling component obtained from a removal line 11 was analyzed, all the examples satisfied the above-mentioned items (iv) to (vi), and could stably produce the diaryl carbonates. The results are shown in Table 8.

TABLE 7

| | average degree of polymerization | molar ratio of (phenyl salicylate and phenyl salicylate carbonate)/Ti in composition A | state of distillation column at start of feed | average recovery of diphenyl carbonate [kg/hr] | continuous operation time [hr] |
|---|---|---|---|---|---|
| Example 15 | 2 | 0.7 | no clogging | 4.1 | 200 |
| Example 16 | 4 | 0.5 | no clogging | 4.0 | 200 |
| Example 17 | 6 | 0.4 | no clogging | 4.0 | 200 |
| Example 18 | 10 | 0.4 | no clogging | 4.1 | 200 |
| Example 19 | 2 | 2.0 | no clogging | 4.0 | 150 |
| Example 20 | 2 | 3.5 | no clogging | 3.5 | 150 |
| Example 21 | 2 | 3.0 | no clogging | 3.7 | 150 |
| Example 22 | 2 | 1.5 | no clogging | 4.0 | 120 |
| Example 23 | 4 | 1.0 | no clogging | 4.0 | 200 |
| Example 24 | 4 | 2.0 | no clogging | 3.9 | 150 |
| Example 25 | 4 | 3.5 | no clogging | 3.6 | 150 |
| Example 26 | 4 | 3.0 | no clogging | 3.7 | 150 |
| Example 27 | 7 | 2.0 | no clogging | 4.0 | 200 |
| Example 28 | 7 | 2.5 | no clogging | 3.9 | 150 |
| Example 29 | 7 | 3.0 | no clogging | 3.7 | 150 |
| Example 30 | 7 | 3.5 | no clogging | 3.6 | 150 |

TABLE 8 molar ratio of each compound to titanium atoms $$\underset{O}{\overset{OH}{\underset{\|}{Ar}}}\overset{}{\underset{}{\diagdown}}C\overset{O\diagdown R}{}$$

| | phenyl salicylate | salicylate ester carbonate | phenyl salicylate carbonate | catechol |
|---|---|---|---|---|
| Example 15 | 0.1 | 1.0 | 0.07 | 0.1 | 0.01 |
| Example 16 | 0.3 | 0.9 | 0.08 | 0.2 | 0.03 |

TABLE 8-continued molar ratio of each compound to titanium atoms

|  | Ar(OH)–C(=O)–O–R phenyl salicylate | salicylate ester carbonate | phenyl salicylate carbonate | catechol |
|---|---|---|---|---|
| Example 17 | 0.3 | 0.9 | 0.10 | 0.4 | 0.02 |
| Example 18 | 0.2 | 1.0 | 0.08 | 0.3 | 0.03 |
| Example 19 | 0.5 | 2.5 | 0.10 | 0.6 | 0.04 |
| Example 20 | 0.6 | 3.8 | 0.10 | 0.8 | 0.04 |
| Example 21 | 0.4 | 3.6 | 0.08 | 0.7 | 0.02 |
| Example 22 | 0.3 | 1.9 | 0.09 | 0.5 | 0.03 |
| Example 23 | 0.2 | 1.6 | 0.06 | 0.4 | 0.02 |
| Example 24 | 0.4 | 2.6 | 0.09 | 0.6 | 0.03 |
| Example 25 | 0.6 | 3.8 | 0.10 | 0.9 | 0.02 |
| Example 26 | 0.6 | 3.7 | 0.09 | 0.8 | 0.03 |
| Example 27 | 0.5 | 2.6 | 0.07 | 0.6 | 0.04 |
| Example 28 | 0.5 | 3.0 | 0.09 | 0.7 | 0.05 |
| Example 29 | 0.4 | 3.6 | 0.10 | 0.9 | 0.04 |
| Example 30 | 0.5 | 3.9 | 0.09 | 0.8 | 0.05 |

Example 31

Preparation of Titanium-Containing Composition 7 kg of polytitanoxane butoxide (manufactured by E.I. DuPont de Nemours & Company Inc., product name: Tyzor BTP) was charged to a batch type reactor equipped with an agitator, a heater, and a distillation column and having a volume of 60 L under a nitrogen atmosphere, and 14 kg of previously distilled/purified phenol was then charged thereto.

Next, the mixture in the batch type reactor was heated to 180° C. under a normal pressure by the heater to react the mixture. n-Butanol generated by the reaction was recovered from the column top of the distillation column. Furthermore, the batch type reactor was depressurized to about 53 kPa, and n-butanol was recovered.

The batch type reactor was then returned to a normal pressure. About 18 kg of diphenyl carbonate was charged thereto. The mixture in the reactor was heated to about 190° C. Next, the batch type reactor was depressurized to about 1.3 kPa, and the diphenyl carbonate containing a low boiling component was evaporated to obtain a titanium-containing composition. Diphenyl carbonate was added so that the titanium concentration of the obtained titanium-containing composition was 5% by mass.

(Preparation of Composition A)

The titanium-containing composition was then heated to 200° C., and was held for about 120 hr so as to obtain a composition A. When part of the composition A was then sampled and analyzed, phenyl salicylate and phenyl salicylate carbonate having a higher boiling point than that of the diphenyl carbonate were detected. The molar ratio of total of phenyl salicylate and phenyl salicylate carbonate, and titanium atoms (total of phenyl salicylate and phenyl salicylate carbonate/titanium atoms) was about 2.3. The composition A generated herein was used as a reaction catalyst for the next production of a diaryl carbonate.

(Producing Apparatus of Diaryl Carbonate)

A schematic configuration view of a producing apparatus used in example 31 is shown in FIG. 1.

The producing apparatus is equipped with distillation columns 110 and 120 which have a continuous multistage structure, a distillation column 130, and a distillation purification column 140.

These are connected via predetermined lines.

Specifically, lines 1 and 12 are feed lines feeding raw compounds and a titanium-containing composition, or the like. Lines 3 and 9 are recovery lines recovering a product compound and other materials. Lines 2, 4, 5, 6, 7, 8, and 10 are transfer lines. A line 11 is a removal line.

Reference numerals 111, 121, 131, and 141 designate reboilers, and reference numerals 112, 122, 132, and 142 designate condensers. Reference numeral 113 designate a preheater for setting a feed material to a predetermined temperature.

(Production of Diaryl Carbonate)

The distillation column 110 had a continuous multistage structure, and was equipped with a concentration part and a recovery part. The concentration part was filled with sieve trays of 25 stages, and had an inner diameter of 150 mm and a length of 4.8 m. The recovery part was filled with Melapak CY (manufactured by Sulzer Chemtech Ltd., Switzerland), and had an inner diameter of 150 mm and a length of 2.3 m.

In the distillation column 110, bis(3-methylbutyl) carbonate, phenol, and the composition A prepared above were continuously fed at about 1830 g/hr from the feed line 1 through the preheater 113 from the sieve tray of the 25th stage to perform a transesterification reaction. The feed rate of each material mixed liquid was adjusted so that the mass ratio of bis(3-methylbutyl)carbonate to phenol in the mixed liquid was about 1.08, and a titanium atom concentration was about 500 ppm.

The concentration part was provided below the stage continuously feeding the mixed liquid, and the recovery part was provided above the stage.

An amount of heat required for the reaction and distillation was controlled by providing an external heater, or by circulating a liquid in a lower column part through the reboiler 111. The method controlled the temperature of the column bottom of the multistage distillation column 110 to about 230° C., and the pressure of the column top thereof to about 140 kPa.

A reaction solution was continuously removed at about 1700 g/hr through the transfer line 2 from the column bottom of the continuous multistage distillation column 110.

A low boiling component containing 3-methyl-1-butanol as by-product was removed from the column top. The low boiling component was then condensed by the condenser 112, and was recovered by a reflux ratio of 2 from the recovery line 3.

The reaction solution removed from the transfer line 2 as described above was fed to the continuous multistage distillation column 120.

The continuous multistage distillation column 120 is equipped with the reboiler 121, the concentration part of a chimney type distillation column (the inner diameter: 150 mm, the length: about 6 m) of 5 stages, and the recovery part filled with Melapak CY and having an inner diameter of 150 mm and a length of 3.8 m. The feeding position of the reaction solution was set at the upper portion of the concentration part, and the feed rate of the reaction solution was set at about 1700 g/hr.

A temperature of the column bottom of the distillation column 120 was controlled to 200° C., and a pressure of the column top thereof was controlled to about 3 kPa. A disproportionation reaction was performed under these conditions.

A low boiling component containing phenol and bis(3-methylbutyl)carbonate was circulated to the distillation column 110 through the condenser 122, the transfer line 5, and the feed line 1 from the column top of the distillation column 120.

From the column bottom of the distillation column 120, the reaction solution containing diphenyl carbonate was fed to the distillation column 130 through the transfer line 4 to perform distillation separation.

The distillation column 130 was a distillation column filled with Melapak CY and having an inner diameter of 150 mm and a length of 4 m, and was provided with the reboiler 131 and the condenser 132.

A temperature of the column bottom of the distillation column 130 was controlled to about 180° C., and a pressure of the column top thereof was controlled to about 0.5 kPa.

The low boiling component containing diphenyl carbonate was removed from the column top, and was fed to the distillation purification column 140 through the condenser 132 and the transfer line 7.

On the other hand, a high boiling component containing a composition A was circulated to the distillation column 110 through the transfer line 6 and the feed line 1.

The distillation purification column 140 was a distillation column filled with Melapak CY and having an inner diameter of 150 mm and a length of 5 m, and was equipped with the reboiler 141 and the condenser 142.

The reaction solution containing diphenyl carbonate, fed to the distillation purification column 140 through the transfer line 7 from the distillation column 130 was purified in the distillation purification column 140. About 100% by mass of the diphenyl carbonate (diaryl carbonate) was obtained from the recovery line 9 by the purification. The position of the recovery line 9 was set at the lower portion of the distillation column located above the column bottom.

The low boiling component containing 3-methylbutyl phenyl carbonate was removed from the column top of the distillation purification column 140, and was circulated to the distillation column 120 through the recovery line 10 and the transfer line 2.

A rate of a titanium-containing high boiling component removed from the removal line 11 was adjusted to about 7.7 g/hr (the titanium atom concentration: about 1.5% by mass), and the rate of the composition A fed from the feed line 12 was adjusted to about 2.3 g/hr (the titanium atom concentration: about 5% by mass). The feed of the composition A from the feed line 1 was stopped.

Simultaneously, an amount of a liquid circulated to each distillation column was gradually increased so that the rate of diphenyl carbonate recovered from the recovery line 9 was about 1000 g/hr.

After the continuous operation described above was performed for about 12 hours, the operation entered into a steady state.

At that time, in the transfer line 2, the composition of the liquid contained about 15% by mass of phenol, about 67% by mass of bis(3-methylbutyl)carbonate, about 17% by mass of 3-methy butyl phenyl carbonate, about 0.3% by mass of diphenyl carbonate, and about 0.2% by mass of 3-methyl-1-butanol. The flow rate thereof was about 11402 g/hr.

The residence times of the reaction solution in the steady state in the distillation columns 110 and 120 were respectively about 1 hr and about 2.5 hr.

The composition of the liquid in the recovery line 3 contained about 100% by mass of 3-methyl-1-butanol. The flow rate thereof was about 823 g/hr.

In the transfer line 4, the composition of the liquid contained about 0.2% by mass of bis(3-methylbutyl) carbonate, about 11% by mass of 3-methylbutyl phenyl carbonate, and about 84% by mass of diphenyl carbonate. The flow rate thereof was about 1238 g/hr.

In the transfer line 5, the composition of the liquid contained about 0.2% by mass of 3-methyl-1-butanol, about 17% by mass of phenol, and about 83% by mass of bis(3-methylbutyl)carbonate. The flow rate thereof was about 10300 g/hr.

In the transfer line 7, the composition of the liquid contained about 88% by mass of diphenyl carbonate, about 12% by mass of 3-methy butyl phenyl carbonate, and about 0.2% by mass of bis(3-methylbutyl)carbonate. The flow rate thereof was about 1140 g/hr.

When the titanium-containing high boiling component obtained from the removal line 11 was analyzed, the ratio of total moles of phenyl salicylate and 3-methylbutyl salicylate ester to moles of titanium atoms was about 2.6.

After the continuous operation described above was further continued for about 300 hr, the diphenyl carbonate (diaryl carbonate) recovered from the recovery line 9 could be stably produced at about 1000 g/hr.

The rate of the titanium-containing high boiling component removed from the removal line 11 was then adjusted to about 6 g/hr (the titanium atom concentration: about 1.5% by mass), and the rate of the composition A fed from the feed line 12 was adjusted to about 1.8 g/hr (the titanium atom concentration: about 5% by mass). Similarly, the continuous operation was performed for about 300 hr.

Similarly, the diphenyl carbonate (diaryl carbonate) recovered from the recovery line 9 could be stably produced at about 1000 g/hr.

When the titanium-containing high boiling component obtained from the removal line 11 was analyzed, the ratio of total moles of salicylate esters of phenyl salicylate plus 3-methylbutyl salicylate ester to moles of titanium atoms was about 3.0. The ratio of moles of phenyl salicylate carbonate to moles of titanium atoms was about 1.1. Furthermore, the ratio of moles of catechol to moles of titanium atoms was about 0.04.

In the distillation separation in the distillation column 130, the high boiling component removed from the column bottom contained about 62% by mass of a component having a higher boiling point than that of the diphenyl carbonate.

Examples 32 to 35

Diphenyl carbonate (diaryl carbonate) was produced in the same manner as in the example 31 except that dialkyl carbonates of types shown in the following Table 9 were used in place of bis(3-methylbutyl)carbonate, and the molar ratio of total of phenyl salicylate and phenyl salicylate carbonate, and titanium atoms (total of phenyl salicylate and phenyl salicylate carbonate/titanium atoms) in a composition A was changed as shown in the following Table 9 in preparation of the composition A. A flow rate in each transfer line and a pressure in a distillation column were adjusted according to the kind of dialkyl carbonate. The results are shown in Table 9. The results showed that continuous operation could be stably performed for a long time without blocking the distillation column in all examples 31 to 35.

In distillation separation in a distillation column 130, a high boiling component removed from a column bottom contained about 28% by mass, about 30% by mass, about 32% by mass, and about 38% by mass of a component having a higher boiling point than that of the diphenyl carbonate, in order of the examples 32 to 35.

When the titanium-containing high boiling component obtained from a removal line 11 was analyzed, all the examples satisfied the above-mentioned items (iv) to (vi), and could stably produce the diaryl carbonates. The results are shown in Table 10.

Comparative Examples 19 to 22

Preparation of Reaction Catalyst

Titanium-containing compositions were prepared in the same manner as in the example 13 except that polytitanoxane butoxides having different average degrees of polymerization, obtained from the production examples 1 to 4 were used in place of polytitanoxane butoxide (manufactured by E.I. DuPont de Nemours & Company Inc., product name: Tyzor BTP) in preparation of the titanium-containing compositions.

(Production of Diaryl Carbonate)

Diphenyl carbonate (diaryl carbonate) was produced in the same manner as in the example 13 except that the titanium-containing composition prepared above was used as a reaction catalyst for a diaryl carbonate as it is without preparing a composition A from the titanium-containing composition. The results are shown in Tables 11 and 12. When the titanium-containing composition was fed for several hours (3 to 6 hr) in all the comparative examples 19 to 22, the feed line 13 was blocked, and the operation became impossible.

TABLE 9

| | dialkyl carbonate | molar ratio of (phenyl salicylate and phenyl salicylate carbonate)/Ti in composition A | state of distillation column at start of feed | average recovery of diphenyl carbonate [kg/hr] | continuous operation time [hr] |
|---|---|---|---|---|---|
| Example 32 | bis(2-methylpropyloxy) carbonate | 0.4 | no clogging | 1.1 | 500 |
| Example 33 | bis(2-ethylbutyloxy) carbonate | 0.5 | no clogging | 1.0 | 600 |
| Example 34 | di(n-butyl) carbonate | 1.0 | no clogging | 1.0 | 500 |
| Example 35 | bis(n-pentyl) carbonate | 1.5 | no clogging | 0.9 | 500 |

TABLE 10

| | molar ratio of each compound to titanium atoms | | | |
|---|---|---|---|---|
| | phenyl salicylate | salicylate ester carbonate | phenyl salicylate carbonate | catechol |
| Example 32 | 0.1 | 1.1 | 0.06 | 0.2 | 0.02 |
| Example 33 | 0.2 | 1.2 | 0.06 | 0.3 | 0.02 |
| Example 34 | 0.3 | 1.6 | 0.08 | 0.5 | 0.03 |
| Example 35 | 0.4 | 2.1 | 0.10 | 0.7 | 0.03 |

TABLE 11

| | average degree of polymerization | molar ratio of (phenyl salicylate and phenyl salicylate carbonate)/ Ti in composition A | state of distillation column at start of feed |
|---|---|---|---|
| Comparative Example 19 | 2 | 0.002 | Distillation column was blocked during catalyst feed, resulting in no more operation possible |
| Comparative Example 20 | 4 | 0.003 | Distillation column was blocked during catalyst feed, resulting in no more operation possible |
| Comparative Example 21 | 7 | 0.001 | Distillation column was blocked during catalyst feed, |

TABLE 11-continued

| | average degree of polymer- ization | molar ratio of (phenyl salicylate and phenyl salicylate carbonate)/ Ti in composition A | state of distillation column at start of feed |
|---|---|---|---|
| Comparative Example 22 | 10 | 0.002 | resulting in no more operation possible Distillation column was blocked during catalyst feed, resulting in no more operation possible |

TABLE 12

| | average degree of polymer- ization | molar ratio of each compound to titanium atoms | | | |
|---|---|---|---|---|---|
| | | methyl salicylate | phenyl salicylate | salicylate ester carbonate | phenyl salicylate carbonate |
| Comparative Example 19 | 2 | not detected | 0.001 | not detected | not detected |
| Comparative Example 20 | 4 | not detected | 0.002 | not detected | not detected |
| Comparative Example 21 | 7 | not detected | not detected | not detected | not detected |
| Comparative Example 22 | 10 | not detected | 0.001 | not detected | not detected |

Comparative Examples 23 to 26

Preparation of Reaction Catalyst

Titanium-containing compositions were prepared in the same manner as in the example 13 except that polytitanoxane butoxides having different average degrees of polymerization, obtained from the production examples 1 to 4 were used in place of polytitanoxane butoxide (manufactured by E.I. DuPont de Nemours & Company Inc., product name: Tyzor BTP) in preparation of the titanium-containing composition.

(Production of Diaryl Carbonate)

Diphenyl carbonate (diaryl carbonate) was produced in the same manner as in the example 13 except that a temperature as a heating condition in preparing a composition A was changed to 230° C. from 200° C., and the heating time was changed to 200 hr from 72 hr. The results are shown in Tables 13 and 14. A problem of clogging was not caused in feeding the composition A. However, since the amount of production of diphenyl carbonate (diaryl carbonate) was unstable, the continuous operation time was about 8 to 30 hours.

TABLE 13

| | average degree of polymer- ization | molar ratio of (phenyl salicylate and phenyl salicylate carbonate)/ Ti in compo- sition A | state of distil- lation column at start of feed | average recovery of diphenyl carbonate [kg/hr] | continuous operation time [hr] |
|---|---|---|---|---|---|
| Comparative Example 23 | 2 | 5.5 | no clogging | 1.0 | 20 |
| Comparative Example 24 | 4 | 5.0 | no clogging | 0.7 | 15 |
| Comparative Example 25 | 7 | 4.3 | no clogging | 1.3 | 30 |
| Comparative Example 26 | 10 | 4.5 | no clogging | 0.6 | 8 |

TABLE 14

| | | molar ratio of each compound to titanium atoms | | | | |
|---|---|---|---|---|---|---|
| | average degree of polymerization | methyl salicylate | phenyl salicylate | salicylate ester carbonate | phenyl salicylate carbonate | catechol |
| Comparative Example 23 | 2 | 0.5 | 5.5 | 0.4 | 0.7 | 0.03 |
| Comparative Example 24 | 4 | 0.6 | 4.1 | 0.3 | 0.5 | 0.04 |
| Comparative Example 25 | 7 | 0.5 | 4.1 | 0.3 | 0.5 | 0.02 |
| Comparative Example 26 | 10 | 0.7 | 4.1 | 0.3 | 0.4 | 0.03 |

Example 36

Preparation of Titanium-Containing Composition 200 kg of polytitanoxane butoxide (manufactured by E.I. DuPont de Nemours & Company Inc., product name: Tyzor BTP) was charged to a batch type reactor equipped with an agitator, a heater, and a distillation column and having a volume of 1800 L under a nitrogen atmosphere, and 485 kg of previously distilled/purified phenol was then charged thereto.

Next, the mixture in the batch type reactor was heated to 180° C. under a normal pressure by the heater to react the mixture. n-Butanol generated by the reaction was recovered from the column top of the distillation column. Furthermore, the batch type reactor was depressurized to about 53 kPa, and n-butanol was recovered.

The batch type reactor was then returned to a normal pressure. About 450 kg of diphenyl carbonate was charged thereto. The mixture in the reactor was heated to about 190° C. Next, the batch type reactor was depressurized to about 1.3 kPa, and the diphenyl carbonate containing a low boiling component was evaporated to obtain a titanium-containing composition. Diphenyl carbonate was added so that the titanium concentration of the obtained titanium-containing composition was 5% by mass.

(Producing Apparatus of Diaryl Carbonate)

A schematic configuration view of a producing apparatus used in example 36 is shown in FIG. 2.

The producing apparatus is equipped with distillation columns 110 and 120 which have a continuous multistage structure, a distillation column 130, and a distillation purification column 140.

These are connected via predetermined lines.

Specifically, lines 1, 1', 12, and 13 are feed lines feeding raw compounds and a titanium-containing composition, or the like. Lines 3 and 9 are recovery lines recovering a product compound and other materials. Lines 2, 4, 5, 6, 7, 8, and 10 are transfer lines. A line 11 is a removal line.

Reference numerals designate 111, 121, 131, and 141 designate reboilers, and reference numerals 112, 122, 132, and 142 designate condensers. Reference numeral 113 designate a preheater for setting a feed material to a predetermined temperature.

(Preparation of Reaction Catalyst)

In the distillation column 130, as described below, a product having a higher boiling point than that of diphenyl carbonate was produced to prepare a reaction catalyst.

The distillation column 130 was a distillation column filled with Melapak CY and having an inner diameter of 3.4 m and a length of 17 m, and was provided with the reboiler 131 and the condenser 132.

About 5200 kg of the prepared titanium-containing composition (the titanium concentration: about 5% by mass) was fed to the lower portion of the distillation column 130. A temperature of the titanium-containing composition was controlled to about 200° C. This state was held for about 60 hr. When part of the titanium-containing composition was then sampled and analyzed, phenyl salicylate having a higher boiling point than that of the diphenyl carbonate was detected. The molar ratio of phenyl salicylate and titanium atoms (phenyl salicylate/titanium atoms) was about 0.4. The mixture (hereinafter, also described as "composition A") of the high boiling product material generated in the distillation column 130 and the titanium-containing composition was used as a reaction catalyst for the next production of a diaryl carbonate.

(Production of Diaryl Carbonate)

The distillation column 110 had a continuous multistage structure. The distillation column 110 was filled with sieve trays of 80 stages and had an inner diameter of 5 m and a length of 33 m. In the distillation column 110, a mixed liquid (a) containing about 30% by mass of dimethyl carbonate and about 70% by mass of phenol was continuously fed at about 57 ton/hr to the upper portion of the distillation column 110 from the feed line 1 through the preheater 113. On the other hand, a mixed liquid (b) containing about 70% by mass of dimethyl carbonate and about 30% by mass of phenol was continuously fed at about 57 ton/hr to the lower portion of the distillation column 110 from the feed line 1'.

A concentration part was provided below the stage continuously feeding the mixed liquids (a) and (b), and a recovery part was provided above the stage.

An amount of heat required for the reaction and distillation was controlled by providing an external heater, or by circulating a liquid in a lower column part through the reboiler. The method controlled a temperature of the column bottom of the multistage distillation column 110 to about 230° C., and controlled a pressure of the column top thereof to about 0.55 MPa-G.

Next, the prepared reaction catalyst (composition A) was gradually fed to the upper portion of the distillation column 110 from the lower portion of the distillation column 130 using the transfer line 6, and a titanium atom concentration in a reaction solution of the distillation column 110 was adjusted to about 300 ppm. The reaction solution was continuously removed at about 60 ton/hr through the transfer line 2 from the column bottom of the continuous multistage distillation column 110.

A low boiling component containing methanol as by-product was continuously removed from the column top of the distillation column 110.

The reaction solution removed from the transfer line 2 as described above was fed to the continuous multistage distillation column 120.

The continuous multistage distillation column 120 was equipped with the sieve tray type concentration part of 30 stages, the recovery part, the condenser 122, and the reboiler 121. The concentration part had an inner diameter of 5 m and a length of 31 m. The recovery part was filled with Melapak CY. The feeding position of the reaction solution was set at the upper portion of the concentration part, and the feed rate of the reaction solution was set at about 60 ton/hr.

The temperature of the column bottom of the distillation column 120 was controlled to 210° C., and the pressure of the column top thereof was controlled to about 13.3 kPa. A disproportionation reaction was performed under these conditions.

A low boiling component containing phenol and dimethyl carbonate was circulated to the distillation column 110 through the condenser 122, the transfer line 5, and the feed line 1 from the column top of the distillation column 120.

From the column bottom of the distillation column 120, 14 ton/hr of the reaction solution containing diphenyl carbonate was fed to the distillation column 130 through the transfer line 4 to perform distillation separation.

The distillation column 130 was a distillation column filled with Melapak CY and having an inner diameter of 3.4 m and a length of 17 m, and was provided with the reboiler 131 and the condenser 132.

A temperature of the column bottom of the distillation column 130 was controlled to about 190° C., and a pressure of the column top thereof was controlled to about 1.7 kPa.

The low boiling component containing diphenyl carbonate was removed from the column top, and was fed to the distillation purification column 140 through the condenser 132 and the transfer line 7.

On the other hand, a high boiling component containing the reaction catalyst (composition A) was circulated to the distillation column 110 through the transfer line 6 and the feed line 1.

The distillation purification column 140 was a distillation column filled with Melapak CY and having an inner diameter of 2.8 m and a length of 22 m, and was equipped with the reboiler 141 and the condenser 142.

The reaction solution containing diphenyl carbonate fed to the distillation purification column 140 through the transfer line 7 from the distillation column 130 was purified in the distillation purification column 140. 99.8% by mass of diphenyl carbonate (diaryl carbonate) was obtained from the recovery line 9 by the purification. The position of the recovery line 9 was set at the lower portion of the distillation column located above the column bottom.

The low boiling component containing methyl phenyl carbonate was removed from the column top of the distillation purification column 140, and was circulated to the distillation column 120 through the recovery line 10 and the transfer line 2.

After the continuous operation described above was performed for about 24 hours, the operation entered into a steady state.

At that time, in the transfer line 2, the composition of the liquid contained about 55% by mass of phenol, about 26% by mass of dimethyl carbonate, about 17% by mass of methyl phenyl carbonate, about 2% by mass of diphenyl carbonate, and about 0.09% by mass of methanol. The flow rate thereof was about 60 ton/hr.

In the transfer line 4, the composition of the liquid contained about 0.1% by mass of dimethyl carbonate, about 27% by mass of methyl phenyl carbonate, about 3% by mass of phenol, and about 70% by mass of diphenyl carbonate. The flow rate thereof was about 14 ton/hr.

In the transfer line 7, the composition of the liquid contained about 65% by mass of diphenyl carbonate, about 33% by mass of methyl phenyl carbonate, and about 2% by mass of phenol. The flow rate thereof was about 13 ton/hr.

After the continuous operation described above was further continued for about 100 hr, the diphenyl carbonate (diaryl carbonate) recovered from the recovery line 9 could be stably produced at about 7.5 ton/hr.

When the titanium-containing high boiling component obtained from the removal line 11 was analyzed, the ratio of total moles of phenyl salicylate and methyl salicylate ester to moles of titanium atoms was about 1.3.

After the continuous operation described above was further continued for about 500 hr, the diphenyl carbonate (diaryl carbonate) recovered from the recovery line 9 could be stably produced at about 7.6 ton/hr.

The rate of the titanium-containing high boiling component removed from the removal line 11 was then adjusted to about 2.0 kg/hr (the titanium atom concentration: about 1% by mass), and the rate of the reaction catalyst fed from the feed line 12 was adjusted to about 4.0 kg/hr (the titanium atom concentration: about 5% by mass). Similarly, the continuous operation was performed for about 500 hr.

When the titanium-containing high boiling component obtained from the removal line 11 was analyzed, the ratio of total moles of salicylate esters of phenyl salicylate plus methyl salicylate ester to moles of titanium atoms was about 1.9. The ratio of moles of phenyl salicylate carbonate to moles of titanium atoms was about 0.8. Furthermore, the ratio of moles of catechol to moles of titanium atoms was about 0.03.

In the distillation separation in the distillation column 130, the high boiling component removed from the column bottom contained about 40% by mass of a component having a higher boiling point than that of the diphenyl carbonate.

Similarly, the diphenyl carbonate (diaryl carbonate) recovered from the recovery line 9 could be stably produced at about 7.6 ton/hr.

Example 37

Preparation of Titanium-Containing Composition

A titanium-containing composition was prepared in the same manner as in the example 7.

(Producing Apparatus of Diaryl Carbonate)

Figure 3:
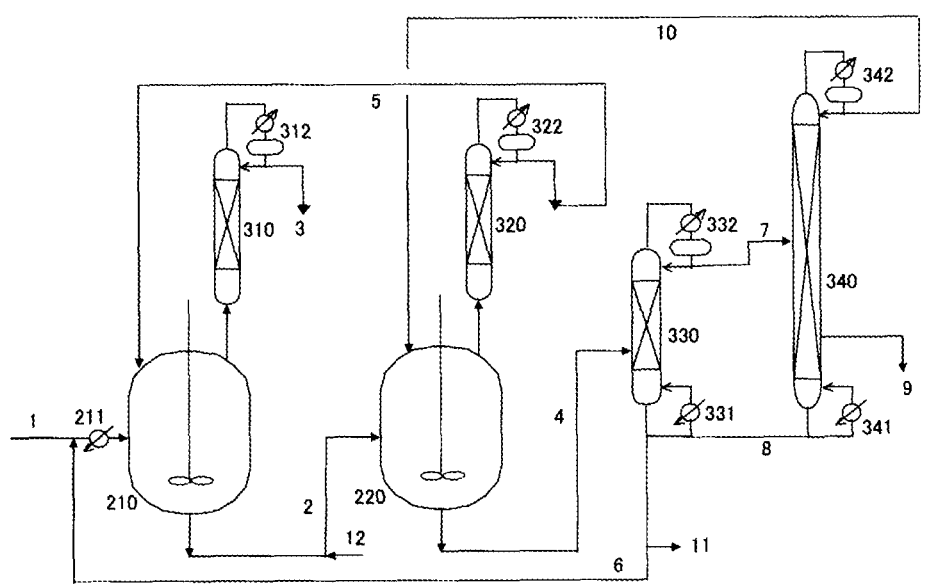
FIG. 3 shows a schematic configuration diagram of one example of the production apparatus for carrying out the method for producing the diaryl carbonate in the present embodiment.

A schematic configuration view of a producing apparatus used in example 37 is shown in FIG. 3.

The producing apparatus is equipped with vessel type reactors 210 and 220, a distillation column 330, and a distillation purification column 340.

These are connected via predetermined lines.

Specifically, lines 1 and 12 are feed lines feeding raw compounds and a titanium-containing composition, or the like. Lines 3 and 9 are recovery lines recovering a product compound and other materials. Lines 2, 4, 5, 6, 7, 8, and 10 are transfer lines. A line 11 is a removal line.

Reference numerals 331, and 341 designate reboilers, and reference numerals 312, 322, 332, and 342 designate condensers. Reference numeral 211 designate a preheater for setting a feed material to a predetermined temperature.

(Preparation of Reaction Catalyst)

In the distillation column 330, as described below, a product having a higher boiling point than that of diphenyl carbonate was produced to prepare a reaction catalyst.

The distillation column 330 was a distillation column filled with Melapak CY and having an inner diameter of 150 mm and a length of 4 m, and was provided with the reboiler 331 and the condenser 332.

About 14 kg of the prepared titanium-containing composition (the titanium concentration: about 5% by mass) was fed to the lower portion of the distillation column 330. A temperature of the titanium-containing composition was controlled to about 200° C. This state was held for about 72 hr. When part of the titanium-containing composition was then sampled and analyzed, phenyl salicylate having a higher boiling point than that of the diphenyl carbonate was detected. The molar ratio of phenyl salicylate and titanium atoms (phenyl salicylate/titanium atoms) was about 0.5. The mixture (hereinafter, also described as "composition A") of the high boiling product material generated in the distillation column 330 and the titanium-containing composition was used as a reaction catalyst for the next production of a diaryl carbonate.

(Production of Diaryl Carbonate)

A mixed liquid containing about 50% by mass of dimethyl carbonate and about 50% by mass of phenol were continuously fed at about 80 kg/hr to the vessel type reactor 210 (volume: 300 L) provided with an agitator from the feed line 1 through the preheater 211.

An amount of heat required for the reaction and distillation was controlled by providing an external heater. The method controlled a temperature of a reaction solution to about 230° C. in the vessel type reactor 210, and controlled the pressure of the column top of a distillation column 310 to about 0.55 MPa-G.

Next, the prepared reaction catalyst (composition A) was gradually fed to the vessel type reactor 210 from the lower portion of the distillation column 330 using the transfer line 6, and a titanium atom concentration in the reaction solution was adjusted to about 1000 ppm to perform a transesterification reaction. The reaction solution containing methyl phenyl carbonate was continuously removed at about 21 kg/hr through the transfer line 2 from the vessel type reactor 210.

A low boiling component containing methanol as by-product was continuously removed from the column top of the distillation column 310. The low boiling component was then condensed by the condenser 312, and was recovered from the recovery line 3.

The reaction solution removed from the transfer line 2 as described above was fed to the vessel type reactor 220.

The vessel type reactor 220 was equipped with an agitator and a distillation column 320 filled with Melapak CY and having an inner diameter of 150 mm and a length of 1.5 m. The feed rate of the reaction solution was set at about 21 kg/hr.

In the vessel type reactor 220, a temperature of the reaction solution was controlled to 210° C., and a pressure of the column top thereof was controlled to about 13.3 kPa. A transesterification reaction or a disproportionation reaction of methyl phenyl carbonate was performed under these conditions, so as to produce diphenyl carbonate.

A low boiling component containing phenol and dimethyl carbonate was circulated to the vessel type reactor 210 through the condenser 322, the transfer line 5, and the feed line 1 from the column top of the distillation column 320.

From the vessel type reactor 220, the reaction solution containing diphenyl carbonate was fed to the distillation column 330 through the transfer line 4 to perform distillation separation.

The distillation column 330 was a distillation column filled with Melapak CY and having an inner diameter of 150 mm and a length of 4 m, and was provided with the reboiler 331 and the condenser 332.

A temperature of the column bottom of the distillation column 330 was controlled to about 190° C., and a pressure of the column top thereof was controlled to about 1.7 kPa.

The low boiling component containing diphenyl carbonate was removed from the column top, and was fed to the distillation purification column 340 through the condenser 332 and the transfer line 7.

On the other hand, a high boiling component containing the reaction catalyst (composition A) was circulated to the distillation column 110 through the transfer line 6 and the feed line 1.

The distillation purification column 340 was a distillation column filled with Melapak CY and having an inner diameter of 150 mm and a length of 5 m, and was equipped with the reboiler 341 and the condenser 342.

The reaction solution containing diphenyl carbonate fed to the distillation purification column 340 through the transfer line 7 from the distillation column 330 was purified in the distillation purification column 340. 99.8% by mass of diphenyl carbonate (diaryl carbonate) was obtained from the recovery line 9 by the purification. The position of the recovery line 9 was set at the lower portion of the distillation column located above the column bottom.

The low boiling component containing methyl phenyl carbonate was removed from the column top of the distillation purification column 340, and was circulated to the vessel type reactor 220 through the recovery line 10.

After the continuous operation described above was performed for about 24 hours, the operation entered into a steady state.

At that time, in the transfer line 2, the composition of the liquid contained about 60% by mass of phenol, about 28% by mass of dimethyl carbonate, about 10% by mass of methyl phenyl carbonate, about 1% by mass of diphenyl carbonate, and about 0.09% by mass of methanol. The flow rate thereof was about 40 kg/hr.

In the transfer line 4, the composition of the liquid contained about 0.1% by mass of dimethyl carbonate, about 37% by mass of methyl phenyl carbonate, about 3% by mass of phenol, and about 60% by mass of diphenyl carbonate. The flow rate thereof was about 6.2 kg/hr.

In the transfer line 7, the composition of the liquid contained about 78% by mass of diphenyl carbonate, about 19% by mass of methyl phenyl carbonate, and about 3% by mass of phenol. The flow rate thereof was about 5 kg/hr.

After the continuous operation described above was further continued for about 100 hr, the diphenyl carbonate (diaryl carbonate) recovered from the recovery line 9 could be stably produced at about 2.7 kg/hr.

When the titanium-containing high boiling component obtained from the removal line 11 was analyzed, the ratio of total moles of phenyl salicylate and methyl salicylate ester to moles of titanium atoms was about 1.2.

After the continuous operation described above was further continued for about 500 hr, the diphenyl carbonate (diaryl carbonate) recovered from the recovery line 9 could be stably produced at about 2.7 kg/hr.

The rate of the titanium-containing high boiling component removed from the removal line 11 was then adjusted to about 5.0 g/hr (the titanium atom concentration: about 2% by mass), and the rate of the reaction catalyst fed from the feed line 12 was adjusted to about 2.0 g/hr (the titanium atom concentration: about 5% by mass). Similarly, the continuous operation was performed for about 500 hr.

When the titanium-containing high boiling component obtained from the removal line 11 was analyzed, the ratio of total moles of salicylate esters of phenyl salicylate plus methyl salicylate ester to moles of titanium atoms was about 1.9. The ratio of moles of phenyl salicylate carbonate to moles of titanium atoms was about 0.8. Furthermore, the ratio of moles of catechol to moles of titanium atoms was about 0.04.

In the distillation separation in the distillation column 330, the high boiling component removed from the column bottom contained about 35% by mass of a component having a higher boiling point than that of the diphenyl carbonate.

Similarly, the diphenyl carbonate (diaryl carbonate) recovered from the recovery line 9 could be stably produced at about 2.7 kg/hr.

Production Example 5

Production of Polytitanoxane Alkoxide 340 kg of tetrabutoxytitanium (manufactured by E.I. DuPont de Nemours & Company Inc., Tyzor TnBT) was introduced to a reactor with an agitator. The reactor was equipped with a cooling coil, a heating jacket, and a distillation column. 150 kg of n-butanol was then introduced thereto, and an internal liquid temperature was adjusted to 0° C.

Hydrous n-butanol having a water concentration set at 3% by mass (% by weight) was adjusted to 0° C. in another reactor with an agitator. The reactor was equipped with a cooling coil, a heating jacket, and a distillation column.

The hydrous n-butanol was added into the reactor under agitation through a line.

The addition time was set at 1.5 hour, and the added amount of water was set at 0.5 molar equivalents (with respect to moles of Ti atoms in the reactor).

A trace moisture meter analyzed a reaction solution with time, and confirmed that the added water was consumed in a hydrolysis reaction and the analyzed value became constant.

The obtained reaction solution was heated under agitation, and n-butanol was evaporated using the distillation column after the reaction solution reached 150° C.

The composition of the evaporated liquid was analyzed by gas chromatography, and it was confirmed that the evaporated amount was mostly lost. The distillation was then completed.

When a transparent and colorless liquid left in the reactor was analyzed and a Ti content and an alkoxy group content were measured, it was found that polytitanoxane butoxide having an average degree of polymerization of 2 was obtained.

Production Examples 6 to 8

Polytitanoxane alkoxides were produced in the same manner as in the above [production example 1] except that the added amount of water was changed as shown in Table 15. After the addition of water was completed, the reaction solution obtained as in the production example 5 was heated under agitation, and n-butanol was evaporated using the distillation column after the reaction solution reached 150° C. The composition of the evaporated liquid was analyzed by gas chromatography, and it was confirmed that the evaporated amount was mostly lost. The distillation was then completed. When a transparent and colorless liquid left in the reactor was analyzed and a Ti content and an alkoxy group content were measured, it was found that polytitanoxane butoxides having different average degrees of polymerization as shown in Table 15 were obtained.

TABLE 15

|  | added amount of water with respect to moles of titanium [molar equivalent] | average degree of polymerization |
|---|---|---|
| production example 6 | 0.76 | 4 |
| production example 7 | 0.86 | 7 |
| production example 8 | 0.89 | 10 |

Examples 38 to 42

Diphenyl carbonate (diaryl carbonate) was produced in the same manner as in the example 36 except that tetrabutoxytitanium (manufactured by E.I. DuPont de Nemours & Company Inc., Tyzor TnBT) and the polytitanoxane alkoxides obtained from the production examples 5 to 8 were used in place of polytitanoxane butoxide (manufactured by E.I. DuPont de Nemours & Company Inc., product name: Tyzor BTP) in preparation of a titanium-containing composition.

In distillation separation in a distillation column 130, a high boiling component removed from a column bottom contained about 41% by mass, about 45% by mass, about 39% by mass, about 50% by mass, and about 45% by mass of a component having a higher boiling point than that of the diphenyl carbonate, in order of examples 38 to 42.

When a titanium-containing high boiling component obtained from a removal line 11 was analyzed, all the examples satisfied the above-mentioned items (iv) to (vi), and could stably produce the diaryl carbonates. The results are shown in Table 16.

TABLE 16

| | titanium-containing compound | molar ratio of each compound to titanium atoms | | | | | average recovery of diphenyl carbonate [ton/hr] |
|---|---|---|---|---|---|---|---|
| | | methyl salicylate | phenyl salicylate | salicylate ester carbonate | phenyl salicylate carbonate | catechol | |
| Example 38 | tetrabutoxytitanium | 0.3 | 2.3 | 0.2 | 0.5 | 0.04 | 7.7 |
| Example 39 | polytitanoxane butoxide (average degree of polymerization: 2) | 0.4 | 2.1 | 0.3 | 0.6 | 0.05 | 7.6 |
| Example 40 | polytitanoxane butoxide (average degree of polymerization: 4) | 0.2 | 2.5 | 0.5 | 0.7 | 0.03 | 7.6 |
| Example 41 | polytitanoxane butoxide (average degree of polymerization: 7) | 0.5 | 2.3 | 0.3 | 0.6 | 0.05 | 7.5 |

TABLE 16-continued

| | | molar ratio of each compound to titanium atoms | | | | | average recovery of |
|---|---|---|---|---|---|---|---|
| | titanium-containing compound | methyl salicylate | phenyl salicylate | salicylate ester carbonate | phenyl salicylate carbonate | catechol | diphenyl carbonate [ton/hr] |
| Example 42 | polytitanoxane butoxide (average degree of polymerization: 10) | 0.5 | 2.4 | 0.3 | 0.7 | 0.05 | 7.5 |

Production Examples 9 to 14

Titanium-containing compositions were prepared in the same manner as in the example 13. Phenyl salicylate (manufactured by Aldrich Chemical) was then added to the titanium-containing composition without preparing a composition A from the titanium-containing composition, and the obtained mixture was heated at about 170° C., so as to produce a uniform liquid. The ratio of the phenyl salicylate to moles of titanium atoms was adjusted as showed in the following Table 17.

TABLE 17

| | ratio of phenyl salicylate to moles of titanium atoms |
|---|---|
| production example 9 | 1.0 |
| production example 10 | 0.5 |
| production example 11 | 1.6 |
| production example 12 | 4.2 |

TABLE 17-continued

| | ratio of phenyl salicylate to moles of titanium atoms |
|---|---|
| production example 13 | 5.0 |
| production example 14 | 10.0 |

Examples 43 to 45

Diphenyl carbonate (diaryl carbonate) was produced in the same manner as in the example 13 except that the titanium-containing compositions obtained from the production examples 9 to 11 were used.

In distillation separation in a distillation column 130, a high boiling component removed from a column bottom contained about 14% by mass, about 10% by mass, and about 23% by mass of a component having a higher boiling point than that of the diphenyl carbonate, in order of examples 43 to 45.

When a titanium-containing high boiling component obtained from a removal line 11 was analyzed, all the examples satisfied the above-mentioned items (iv) to (vi), and could stably produce the diaryl carbonates. The results are shown in Table 18.

TABLE 18

| | | molar ratio of each compound to titanium atoms | | | | | average recovery of |
|---|---|---|---|---|---|---|---|
| | titanium-containing compound | methyl salicylate | phenyl salicylate | salicylate ester carbonate | phenyl salicylate carbonate | catechol | diphenyl carbonate [kg/hr] |
| Example 8 | composition obtained from production example 9 | 0.4 | 2.0 | 0.1 | 0.3 | 0.04 | 4.0 |
| Example 9 | composition obtained from production example 10 | 0.3 | 1.8 | 0.1 | 0.4 | 0.05 | 4.0 |
| Example 10 | composition obtained from production example 11 | 0.3 | 2.4 | 0.1 | 0.4 | 0.04 | 3.9 |

Comparative Examples 27 to 29

Diphenyl carbonate (diaryl carbonate) was produced in the same manner as in the example 13 except that the titanium-containing compositions obtained from the production examples 12 to 14 were used.

A problem of clogging was not caused in feeding the titanium-containing composition. However, since the amount of production of diphenyl carbonate was unstable, the continuous operation time was about 8 to 12 hours. Diphenyl carbonate was hardly produced in the comparative example 29 using the titanium-containing composition obtained from the production example 14. The results are shown in the following Table 19.

Nemours & Company Inc., product name: Tyzor BTP), and polytitanoxane butoxides obtained from the production examples 1 to 4, which were titanium-containing catalyst compositions, were used for a reaction catalyst for a diaryl carbonate. Start-up operation was performed in the same manner as in the example 1 so as to produce the diaryl carbonate.

In distillation separation in a distillation column 130, a high boiling component removed from a column bottom contained about 5% by mass, about 6% by mass, about 5% by mass, about 7% by mass, about 6% by mass, and about 6% by mass of a component having a higher boiling point than that of the diphenyl carbonate, in order of examples 46 to 51.

TABLE 19

| | titanium-containing compound | molar ratio of each compound to titanium atoms | | | | | average recovery of diphenyl carbonate [kg/hr] | continuous operation time [hr] |
|---|---|---|---|---|---|---|---|---|
| | | methyl salicylate | phenyl salicylate | salicylate ester carbonate | phenyl salicylate carbonate | catechol | | |
| Comparative Example 27 | composition obtained from production example 12 | 0.6 | 4.5 | 0.2 | 0.7 | 0.05 | 0.6 | 10 |
| Comparative Example 28 | composition obtained from production example 13 | 0.5 | 5.6 | 0.3 | 0.8 | 0.04 | 0.3 | 12 |
| Comparative Example 29 | composition obtained from production example 14 | 0.8 | 12.0 | 0.3 | 0.9 | 0.05 | 0.08 | 8 |

Examples 46 to 51

Tetrabutoxytitanium (manufactured by E.I. DuPont de Nemours & Company Inc., product name: Tyzor TnBT), polytitanoxane butoxide (manufactured by E.I. DuPont de The results of analyzing a titanium-containing high boiling component obtained from a removal line 11 are shown in the following Table 20. All the examples satisfied the conditions of the above-mentioned items (iv) to (vi), and could stably produce the diaryl carbonates.

TABLE 20

| | titanium-containing compound | molar ratio of each compound to titanium atoms | | | | | average recovery of diphenyl carbonate [kg/hr] |
|---|---|---|---|---|---|---|---|
| | | methyl salicylate | phenyl salicylate | salicylate ester carbonate | phenyl salicylate carbonate | catechol | |
| Example 46 | tetrabutoxytitanium (Tyzor TnBT) | 0.1 | 0.4 | 0.02 | 0.03 | 0.02 | 1.1 |
| Example 47 | polytitanoxane butoxide (Tyzor BTP) | 0.1 | 0.3 | 0.01 | 0.03 | 0.02 | 1.0 |
| Example 48 | polytitanoxane butoxide obtained from production example 1 (average degree of polymerization: 2) | 0.2 | 0.5 | 0.02 | 0.04 | 0.03 | 1.2 |
| Example 49 | polytitanoxane butoxide obtained from production example 2 (average degree of polymerization: 4) | 0.1 | 0.5 | 0.02 | 0.03 | 0.01 | 1.0 |
| Example 50 | polytitanoxane butoxide obtained from production example 3 (average degree of polymerization: 7) | 0.3 | 0.6 | 0.02 | 0.05 | 0.02 | 1.1 |

TABLE 20-continued

| | titanium-containing compound | molar ratio of each compound to titanium atoms | | | | | average recovery of diphenyl carbonate [kg/hr] |
|---|---|---|---|---|---|---|---|
| | | methyl salicylate | phenyl salicylate | salicylate ester carbonate | phenyl salicylate carbonate | catechol | |
| Example 51 | polytitanoxane butoxide obtained from production example 4 (average degree of polymerization: 10) | 0.2 | 0.5 | 0.01 | 0.03 | 0.02 | 1.0 |

Example 52

A diaryl carbonate was produced as described below, using the producing apparatus of the diaryl carbonate shown in FIG. 1 described in the example 1.
(1) Start-Up Operation A continuous multistage distillation column 110 was equipped with a concentration part and a recovery part. The concentration part was filled with sieve trays of 25 stages, and had an inner diameter of 150 mm and a length of 4.8 m. The recovery part was filled with Melapak CY (manufactured by Sulzer Chemtech Ltd., Switzerland), and had an inner diameter of 150 mm and a length of 2.3 m. In the distillation column 110, a mixed liquid (a weight ratio of bis(3-methylbutyl)carbonate to phenol in the mixed liquid was about 1.08, and tin as atoms was adjusted to about 1500 ppm of the total liquid amount) including bis(3-methylbutyl)carbonate, phenol, and monooctyltin phenoxide oxide (synthesized from the reaction of monooctyltin oxide hydroxide (Hokko Chemical Industry Co., Ltd.) and phenol) was continuously fed at about 1800 g/hr from a feed line 1 through the preheater 113 from the sieve tray of the 25th stage to perform a transesterification reaction.

The concentration part was provided below the stage continuously feeding the mixed liquid, and the recovery part was provided above the stage.

An amount of heat required for the reaction and distillation was controlled by providing an external heater, or by circulating and feeding a liquid in a lower column part through a reboiler 111. Thereby, a temperature of the column bottom of the multistage distillation column 110 was controlled to about 230° C., and a pressure of the column top thereof was controlled to about 140 kPa.

A reaction solution was continuously removed at about 1650 g/hr through a transfer line 2 from the column bottom of the continuous multistage distillation column 110.

A low boiling component containing 3-methyl-1-butanol as by-product was removed from the column top. The low boiling component was then condensed by a condenser 112, and was recovered by a reflux ratio of 2 from a recovery line 3.

The reaction solution removed from the transfer line 2 as described above was fed to a continuous multistage distillation column 120.

The continuous multistage distillation column 120 is equipped with a reboiler 121, the concentration part of a chimney type distillation column (the inner diameter: 150 mm, the length: about 6 m) of 5 stages, and a recovery part filled with Melapak CY and having an inner diameter of 150 mm and a length of 3.8 m. The reaction solution was fed at about 1700 g/hr to the upper portion of the concentration part.

A temperature of the column bottom of the distillation column 120 was controlled to 200° C., and a pressure of the column top thereof was controlled to about 3 kPa. A disproportionation reaction was performed under these conditions.

A low boiling component containing phenol and bis(3-methylbutyl)carbonate was circulated to the distillation column 110 through a condenser 122, a transfer line 5, and a feed line 1 from the column top of the distillation column 120.

From the column bottom of the distillation column 120, the reaction solution containing diphenyl carbonate was fed to a distillation column 130 through a transfer line 4 to perform distillation separation.

The distillation column 130 was a distillation column filled with Melapak CY and having an inner diameter of 150 mm and a length of 4 m, and was provided with a reboiler 131 and a condenser 132.

A temperature of the column bottom of the distillation column 130 was controlled to about 180° C., and a pressure of the column top thereof was controlled to about 0.5 kPa.

The low boiling component containing diphenyl carbonate was removed from the column top, and was fed to a distillation purification column 140 through the condenser 132 and a transfer line 7.

On the other hand, a high boiling component containing a catalyst was circulated to the distillation column 110 through a transfer line 6 and a feed line 1.

A distillation purification column 140 was a distillation column filled with Melapak CY and having an inner diameter of 150 mm and a length of 5 m, and was equipped with a reboiler 141 and a condenser 142.

The reaction solution containing diphenyl carbonate, fed to the distillation purification column 140 through the transfer line 7 from the distillation column 130 was purified in the distillation purification column 140. Thereby, about 99% by mass of diphenyl carbonate was obtained from the recovery line 9 located above the column bottom and located at the lower portion of the distillation column.

The low boiling component containing 3-methylbutyl phenyl carbonate was removed from the column top of the distillation purification column 140, and was circulated to the distillation column 120 through a recovery line 10 and a transfer line 2.
(2) Control Operation A rate of a tin-containing high-boiling substance removed from a removal line 11 was adjusted to about 2.3 g/hr (the tin atom concentration: about 5% by mass), and a rate of an octyltin oxidophenoxide-containing phenol liquid fed from a feed line 12 was adjusted to about 2.3 g/hr (the tin atom concentration: about 5% by mass). The feed of the octyltin oxidophenoxide from the feed line 1 was stopped.

Simultaneously, an amount of a liquid circulated to each distillation column was gradually increased so that the rate of diphenyl carbonate recovered from the recovery line 9 was about 1000 g/hr.

After the continuous operation described above was performed for about 12 hours, the operation entered into a steady state.

At that time, in the transfer line 2, the composition of the liquid contained about 15% by mass of phenol, about 67% by mass of bis(3-methylbutyl)carbonate, about 17% by mass of 3-methy butyl phenyl carbonate, about 0.3% by mass of diphenyl carbonate, and about 0.2% by mass of 3-methyl-1-butanol. The flow rate thereof was about 11402 g/hr.

The composition of the liquid in the recovery line 3 contained about 100% by mass of 3-methyl-1-butanol. The flow rate thereof was about 825 g/hr.

In the transfer line 4, the composition of the liquid contained about 0.2% by mass of bis(3-methylbutyl) carbonate, about 11% by mass of 3-methylbutyl phenyl carbonate, and about 84% by mass of diphenyl carbonate. The flow rate thereof was about 1230 g/hr.

In the transfer line 5, the composition of the liquid contained about 0.2% by mass of 3-methyl-1-butanol, about 15% by mass of phenol, and about 84% by mass of bis(3-methylbutyl)carbonate. The flow rate thereof was about 10300 g/hr.

In the transfer line 7, the composition of the liquid contained about 86% by mass of diphenyl carbonate, about 13% by mass of 3-methy butyl phenyl carbonate, and about 0.2% by mass of bis(3-methylbutyl)carbonate. The flow rate thereof was about 1120 g/hr.

Similarly, the diphenyl carbonate recovered from the recovery line 9 could be stably produced at about 1000 g/hr.

Examples 53 to 55

Diaryl carbonates were produced in the same manner as in the example 52 except that triethoxyiron (manufactured by Strem Chemicals, Inc.), tributoxyaluminum (manufactured by Wako Pure Chemical Industries, Ltd.), and tripropoxyzirconium (manufactured by Strem Chemicals, Inc.) were respectively used as a metal-containing catalyst in order in examples 53 to 55.

In distillation separation in a distillation column 130, a high boiling component removed from a column bottom contained about 14% by mass, about 15% by mass, and about 17% by mass of a component having a higher boiling point than that of the diphenyl carbonate, in order of the examples 53 to 55.

When a metal-containing high boiling component obtained from a removal line 11 was analyzed, all the examples satisfied the above-mentioned items (iv) to (vi), and could stably produce the diaryl carbonates. The results are shown in Table 21.

TABLE 21

| | metal-containing catalyst composition | 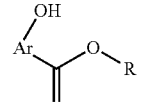 | phenyl salicylate | salicylate ester carbonate | phenyl salicylate carbonate | catechol | average recovery of diphenyl carbonate [kg/hr] |
|---|---|---|---|---|---|---|---|
| Example 53 | triethoxyiron | 0.1 | 1.0 | 0.03 | 0.3 | 0.02 | 1.0 |
| Example 54 | tributoxyaluminum | 0.2 | 1.2 | 0.05 | 0.5 | 0.02 | 0.9 |
| Example 55 | tripropoxyzirconium | 0.1 | 0.9 | 0.03 | 0.4 | 0.03 | 0.9 |

(molar ratio of each compound to titanium atoms)

When the high boiling component obtained from the removal line 11 was analyzed, the ratio of total moles of phenyl salicylate and 3-methylbutyl salicylate ester to moles of tin atoms was about 0.4.

After the continuous operation described above was further continued for about 100 hr, the diphenyl carbonate recovered from the recovery line 9 could be stably produced at about 1000 g/hr.

The rate of the tin-containing high-boiling substance removed from the removal line 11 was then adjusted to about 1.8 g/hr (the tin atom concentration: about 5% by mass), and the rate of the octyltin oxidophenoxide-containing phenol liquid fed from the feed line 12 was adjusted to about 1.8 g/hr (the tin atom concentration: about 5% by weight). Similarly, the continuous operation was performed for about 100 hr.

When the high boiling component obtained from the removal line 11 was analyzed, the ratio of total moles of salicylate esters of phenyl salicylate plus 3-methylbutyl salicylate ester to moles of tin atoms was about 0.7. The ratio of moles of phenyl salicylate carbonate to moles of tin atoms was about 0.05. Furthermore, the ratio of moles of catechol to moles of tin atoms was about 0.02. The ratio of a component having a higher boiling point than that of the diphenyl carbonate in the high boiling component was about 23% by mass.

Comparative Examples 30 to 33

Diaryl carbonates were produced using the producing apparatus shown in FIG. 1.

The diaryl carbonates were produced in the same manner as in the example 52 except that monooctyltin phenoxide oxide, triethoxyiron (manufactured by Strem Chemicals, Inc.), tributoxyaluminum (manufactured by Wako Pure Chemical Industries, Ltd.), and tripropoxyzirconium (manufactured by Strem Chemicals, Inc.) were respectively used as a metal-containing catalyst in comparative examples 30 to 33, and control operation was performed as described below.

(Control Operation)

The same start-up operation as the example 52 was performed to adjust a rate of a metal-containing high-boiling substance removed from a removal line 11 to about 2.4 g/hr (the metal atom concentration: about 5% by mass), and a rate of a metal-containing catalyst composition fed from a feed line 12 to about 2.4 g/hr (the metal atom concentration: about 5% by mass). Simultaneously, an amount of a liquid circulated to each distillation column was gradually increased so that the rate of diphenyl carbonate recovered from a recovery line 9 was about 1000 g/hr. After continuous operation was performed for about 12 hours, the operation entered into a steady state.

Then, a rate of a high boiling component removed from the removal line 11 was gradually adjusted to about 0.4 g/hr (the metal atom concentration: about 5% by mass), and a rate of a metal-containing catalyst composition liquid fed from the feed line 12 was gradually adjusted to about 0.4 g/hr (the metal atom concentration: about 5% by mass). The continuous operation was performed in the same circulated amount of a liquid as that of the example 52.

However, since the diphenyl carbonate recovered from the recovery line 9 was gradually decreased, a material liquid fed from the feed line 1 was adjusted corresponding thereto.

After the continuous operation was performed for about 100 hr, the rate of the diphenyl carbonate recovered from the recovery line 9 in the steady state was about 150 g/hr.

Furthermore, the rate of the tin-containing high-boiling substance removed from the removal line 11 was adjusted to about 0.3 g/hr (the metal atom concentration: about 5% by mass), and the rate of the metal-containing catalyst composition fed from the feed line 12 was adjusted to about 0.3 g/hr (the metal atom concentration: about 5% by mass). Similarly, the continuous operation was performed.

After the continuous operation was performed for about 100 hr, the rate of the diphenyl carbonate recovered from the recovery line 9 in the steady state was 20 g/hr to 100 g/hr. The results of analyzing the high boiling component obtained from the line 11 are shown in Table 22.

TABLE 22

| | | molar ratio of each compound to titanium atoms | | | | | |
|---|---|---|---|---|---|---|---|
| | metal-containing catalyst composition | 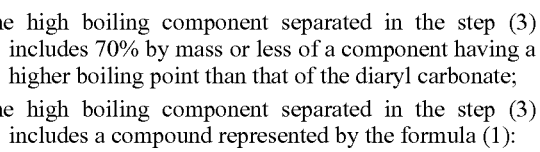 | phenyl salicylate | salicylate ester carbonate | phenyl salicylate carbonate | catechol | average recovery of diphenyl carbonate [kg/hr] |
| Comparative Example 30 | monooctyltin phenoxide oxide | | 0.6 | 4.5 | 0.06 | 0.5 | 0.03 | 0.07 |
| Comparative Example 31 | triethoxyiron | | 0.7 | 4.2 | 0.05 | 0.7 | 0.02 | 0.09 |
| Comparative Example 32 | tributoxyaluminum | | 0.5 | 4.6 | 0.09 | 0.6 | 0.02 | 0.06 |
| Comparative Example 33 | tripropoxyzirconium | | 0.9 | 4.8 | 0.07 | 0.9 | 0.03 | 0.02 |

INDUSTRIAL APPLICABILITY

The producing method of the diaryl carbonate of the present invention has industrial applicability as the technique of producing the diaryl carbonate with stably high productivity.

DESCRIPTION OF REFERENCE NUMERALS

1, 1', 12, 13 FEED LINE
3, 9 RECOVERY LINE
2, 4, 5, 6, 7, 8, 10 TRANSFER LINE
11 REMOVAL LINE
110, 120, 130, 310, 320, 330 DISTILLATION COLUMN
140, 340 DISTILLATION PURIFICATION COLUMN
111, 121, 131, 141, 331, 341 REBOILER
112, 122, 132, 142, 312, 322, 332, 342 CONDENSER
113, 114, 211 PREHEATER
210, 220 VESSEL TYPE REACTOR

What is claimed is:

1. A method for producing a diaryl carbonate, using a metal-containing catalyst composition as a reaction catalyst, comprising:

a step (1) of subjecting a dialkyl carbonate and an aromatic monohydroxy compound to a transesterification reaction so as to obtain an alkylaryl carbonate, and removing an alcohol as by-product from a reaction system;

a step (2) of subjecting the alkylaryl carbonate obtained in the step (1) to a transesterification or disproportionation reaction so as to obtain a reaction product including the diaryl carbonate;

a step (3) of distilling the reaction product obtained in the step (2) to separate the reaction product into a low boiling component including the diaryl carbonate and a high boiling component including the reaction catalyst; and a step (4) of recycling the high boiling component separated in the step (3) into the steps (1) and/or (2), wherein:

the high boiling component separated in the step (3) includes 70% by mass or less of a component having a higher boiling point than that of the diaryl carbonate;

the high boiling component separated in the step (3) includes a compound represented by the formula (1):

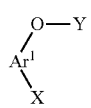  (1)

wherein $Ar^1$ represents an unsubstituted or substituted arylene group having 6 to 20 carbon atoms, X and Y—O are located at an ortho position to each other, X represents a hydroxy group or a substituent given by the formula (2) or (3), and Y represents hydrogen or a substituent given by the formula (3), the formulas (2) and (3) being as follows:

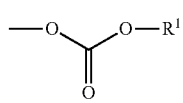  (2)

-continued

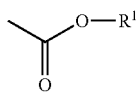
(3)

wherein R¹ represents a linear or branched aliphatic group having 1 to 12 carbon atoms, an alicyclic aliphatic group having 5 to 12 carbon atoms, or an unsubstituted or substituted aryl group having 6 to 20 carbon atoms; and
the high boiling component recycled in the step (4) includes compounds given by (i) to (iii):
(i) a compound of the formula (1) where X represents the formula (2) or (3), and Y represents the formula (3);
(ii) a compound of the formula (1) where X represents a hydroxy group, and Y represents the formula (3), and/or a compound of the formula (1) where X represents the formula (3), and Y represents hydrogen;
(iii) a compound of the formula (1) where X represents a hydroxy group, and Y represents hydrogen;
the compounds of (i) to (iii) satisfying conditions given by (iv) to (vi), respectively:
(iv) total moles of the compounds of (i)/moles of metal atoms is 0.005 to 20;
(v) total moles of the compounds of (ii)/moles of metal atoms is 0.005 to 4; and
(vi) moles of the compound of (iii)/moles of metal atoms is less than 2.

2. The method for producing the diaryl carbonate according to claim 1, wherein the metal-containing catalyst composition is a titanium-containing catalyst composition.

3. The method for producing the diaryl carbonate according to claim 2, wherein the titanium-containing catalyst composition is a titanium-containing composition formed of a diaryl carbonate and an aryloxytitanium composition, and titanium constituting the aryloxytitanium composition has a content of 0.1 to 20% by mass based on 100% by mass of the titanium-containing composition.

4. The method for producing the diaryl carbonate according to claim 3, wherein the titanium constituting the aryloxytitanium composition is tetravalent.

5. The method for producing the diaryl carbonate according to claim 3, wherein the aryloxytitanium composition has 1 or more and 4 or less aryloxy groups per titanium atom.

6. The method for producing the diaryl carbonate according to claim 3, wherein the aryloxytitanium composition is phenoxytitanium.

7. The method for producing the diaryl carbonate according to claim 1, wherein a reaction solvent is used in the steps (1) and/or (2), and the metal-containing catalyst composition is soluble in the reaction solvent or forms a homogeneous phase with the reaction solvent.

8. The method for producing the diaryl carbonate according to claim 1, wherein at least one of the compounds of formula (1) is selected from a group of compounds represented by the following formulas (4) to (8):

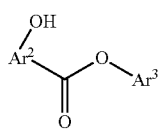
(4)

wherein Ar² represents an unsubstituted or substituted arylene group having 6 to 20 carbon atoms, Ar³ represents an unsubstituted or substituted aryl group having 6 to 20 carbon atoms, and two substituents on Ar² are located at an ortho position to each other;

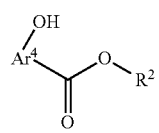
(5)

wherein Ar⁴ represents an unsubstituted or substituted arylene group having 6 to 20 carbon atoms, R² represents a linear or branched aliphatic group having 1 to 12 carbon atoms, or an alicyclic aliphatic group having 5 to 12 carbon atoms, and two substituents on Ar⁴ are located at an ortho position to each other;

(6)

wherein Ar⁵ represents an unsubstituted or substituted arylene group having 6 to 20 carbon atoms, and two hydroxy groups on Ar⁵ are located at an ortho position to each other;

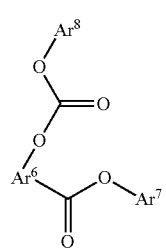
(7)

wherein Ar⁶ represents an unsubstituted or substituted arylene group having 6 to 20 carbon atoms, Ar⁷ and Ar⁸ each independently represent an unsubstituted or substituted aryl group having 6 to 20 carbon atoms, and two substituents on Ar⁶ are located at an ortho position to each other; and

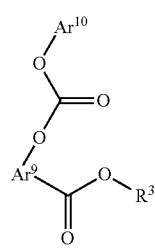
(8)

wherein Ar⁹ represents an unsubstituted or substituted arylene group having 6 to 20 carbon atoms, Ar¹⁰ represents an unsubstituted or substituted aryl group having 6 to 20 carbon atoms, $R^3$ represents a linear or branched aliphatic group having 1 to 12 carbon atoms, or an alicyclic aliphatic group having 5 to 12 carbon atoms, and two substituents on $Ar^9$ are located at an ortho position to each other.

9. The method for producing the diaryl carbonate according to claim 1, wherein the steps (1) and/or (2) is performed in the presence of a composition A comprising a diaryl carbonate, an aryloxytitanium composition, and a compound represented by the following formulas (X) and/or (Y), and the composition A has a ratio of total moles of the compounds represented by the following formulas (X) and (Y) to moles of titanium atoms (a total of the compounds represented by the formulas (X) and (Y)/titanium atoms) from 0.005 to 4, the formulas (X) and (Y) being:

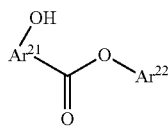

(X)

wherein $Ar^{21}$ represents an unsubstituted or substituted arylene group having 6 to 20 carbon atoms, $Ar^{22}$ represents an unsubstituted or substituted aryl group having 6 to 20 carbon atoms, and two substituents on $Ar^{21}$ are located at an ortho position to each other; and

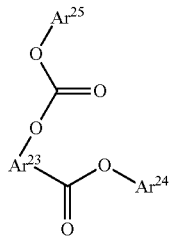

(Y)

wherein $Ar^{23}$ represents an unsubstituted or substituted arylene group having 6 to 20 carbon atoms, $Ar^{24}$ and $Ar^{25}$ each independently represent an unsubstituted or substituted aryl group having 6 to 20 carbon atoms, and two substituents on $Ar^{23}$ are located at an ortho position to each other.

10. The method for producing the diaryl carbonate according to claim 9, wherein in the steps (1) and/or (2), obtaining the alkylaryl carbonate and/or production of the diaryl carbonate is started by feeding the composition A.

11. The method for producing the diaryl carbonate according to claim 1, further comprising sampling the high boiling component recycled in the step (4), adding a monodentate or polydentate ligand capable of coordination to the metal atoms, to the sampled high boiling component at 1 equivalent or more with respect to titanium atoms therein so as to prepare an analysis sample, and analyzing the analysis sample to quantify the compounds given by (i) to (iii) included in the high boiling component.

12. The method for producing the diaryl carbonate according to claim 11, further comprising performing control so that the compounds given by (i) to (iii) included in the high boiling component recycled in the step (4) not extend beyond the conditions of (iv) to (vi), respectively, after the step of quantifying the compounds given by (i) to (iii) according to claim 10.

13. The method for producing the diaryl carbonate according to claim 1, further comprising sampling the high boiling component recycled in the step (4), adding at least one additive to the sampled high boiling component at 1 equivalent or more with respect to the metal atoms therein so as to prepare an analysis sample, the additive being selected from the group consisting of water, polyhydroxy compounds, nitrogen-containing heterocyclic compounds, sulfur-containing heterocyclic compounds, fluorine-substituted alcohols, and fluorine-substituted organic acids, and analyzing the analysis sample by gas or liquid chromatography so as to quantify the compounds given by (i) to (iii) included in the high boiling component.

14. The method for producing the diaryl carbonate according to claim 1, wherein the dialkyl carbonate used in the step (1) is a compound represented by the formula (9):

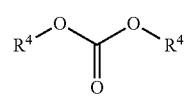

(9)

wherein $R^4$ represents a linear or branched aliphatic group having 1 to 12 carbon atoms, or an alicyclic aliphatic group having 5 to 12 carbon atoms, the aromatic monohydroxy compound used in the step (1) is a compound represented by the formula (10):

(10)

wherein $Ar^{11}$ represents an unsubstituted or substituted aryl group having 6 to 20 carbon atoms, the alkylaryl carbonate obtained in the step (1) is a compound represented by the formula (11):

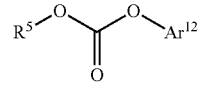

(11)

wherein $R^5$ represents a linear or branched aliphatic group having 1 to 12 carbon atoms, or an alicyclic aliphatic group having 5 to 12 carbon atoms, and $Ar^{12}$ represents an unsubstituted or substituted aryl group having 6 to 20 carbon atoms, and the diaryl carbonate obtained in the step (2) is a compound represented by the formula (12):

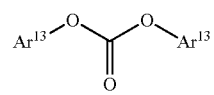

(12)

wherein $Ar^{13}$ represents an unsubstituted or substituted aryl group having 6 to 20 carbon atoms.

15. The method for producing the diaryl carbonate according to claim 14, wherein $R^4$ in the formula (9) is an aliphatic alkyl group having 1 to 8 carbon atoms.

16. The method for producing the diaryl carbonate according to claim 1, wherein the reactions in the steps (1) and (2) are performed using a reaction apparatus comprising at least one selected from the group consisting of an agitation tank, an agitation tank with multistage impellers, a packed column, a distillation column, a multistage distillation column, a continuous multistage distillation column, a reactor comprising an internal support, and a forced circulation reactor.

17. The method for producing the diaryl carbonate according to claim 16, wherein in the step (1), the dialkyl carbonate and the aromatic monohydroxy compound are continuously fed to the reaction apparatus, and in the step (2), the reaction product obtained is continuously removed from the reaction apparatus.

18. The method for producing the diaryl carbonate according to claim 1, wherein the metal atoms in the metal-containing catalyst composition in the step (1) or (2) have a content of 0.0001 to 20% by mass.

19. The method for producing the diaryl carbonate according to claim 1, wherein the steps (1) and (2) have a reaction temperature of 150 to 300° C., and a reaction time of 0.05 to 50 hr.

20. The method for producing the diaryl carbonate according to claim 1, wherein the distillation in the step (3) is performed by a distillation column, the distillation column has a temperature of 150 to 300° C. at a column bottom, and the distillation column provides a residence time of 0.02 to 100 hr at a column bottom.

21. The method for producing the diaryl carbonate according to claim 1, wherein the diaryl carbonate is diphenyl carbonate.

\* \* \* \* \*